(12) United States Patent
Sorensen et al.

(10) Patent No.: US 8,536,196 B2
(45) Date of Patent: Sep. 17, 2013

(54) SUBSTITUTED 1,3-DIOXANES USEFUL AS PPAR MODULATORS

(75) Inventors: Alexandra Santana Sorensen, Holte (DK); Jean-Philippe Meyer, Strasbourg (FR); Peteris Alberts, Helsingborg (SE); Prathama S. Mainkar, Hyderabad (IN); Melya Hughes Crameri, Los Altos, CA (US); Thierry Bonnaud, Cambridge (GB); Joanne Kelleher, Dublin (IE); David Pearson, Royston (GB)

(73) Assignee: Evolva SA, Allschwil (CH)

( * ) Notice: Subject to any disclaimer, the term of this patent is extended or adjusted under 35 U.S.C. 154(b) by 421 days.

(21) Appl. No.: 12/523,843

(22) PCT Filed: Jan. 18, 2008

(86) PCT No.: PCT/US2008/051521
§ 371 (c)(1),
(2), (4) Date: Feb. 17, 2010

(87) PCT Pub. No.: WO2008/089463
PCT Pub. Date: Jul. 24, 2008

(65) Prior Publication Data
US 2010/0168169 A1    Jul. 1, 2010

Related U.S. Application Data

(60) Provisional application No. 60/989,805, filed on Nov. 21, 2007, provisional application No. 60/989,806, filed on Nov. 21, 2007, provisional application No. 60/989,808, filed on Nov. 21, 2007.

(51) Int. Cl.
*A61K 31/42*    (2006.01)

(52) U.S. Cl.
USPC ........... 514/326; 514/452; 514/462; 514/463; 546/19; 546/207; 549/369; 549/370; 549/374; 549/375

(58) Field of Classification Search
USPC ................. 549/369, 370, 374, 375; 546/19, 546/207; 514/326, 452, 462, 463
See application file for complete search history.

(56) References Cited

U.S. PATENT DOCUMENTS

| 4,567,197 | A | 1/1986 | Brewster et al. |
|---|---|---|---|
| 4,723,037 | A | 2/1988 | Harris |
| 4,745,198 | A | 5/1988 | Brewster et al. |
| 4,775,685 | A | 10/1988 | Brewster et al. |
| 4,895,962 | A | 1/1990 | Brewster et al. |
| 4,908,380 | A | 3/1990 | Brewster et al. |
| 5,128,359 | A | 7/1992 | Bru-Magniez et al. |
| 5,166,377 | A | 11/1992 | Brewster et al. |
| 5,248,780 | A | 9/1993 | Brewster et al. |
| 5,312,818 | A | 5/1994 | Rubin et al. |
| 5,462,726 | A | 10/1995 | Lodge |
| 5,801,195 | A | 9/1998 | Muller et al. |
| 5,981,586 | A | 11/1999 | Pershadsingh |
| 6,277,884 | B1 | 8/2001 | de Tejada |
| 6,284,790 | B1 | 9/2001 | Gupte |
| 6,291,496 | B1 | 9/2001 | Dannenberg et al. |
| 6,436,997 | B1 | 8/2002 | de Tejada |
| 6,509,348 | B1 | 1/2003 | Ogletree |
| 6,951,882 | B2 | 10/2005 | Carruthers et al. |
| 2003/0109543 | A1 | 6/2003 | Ogletree |
| 2010/0087517 | A1 | 4/2010 | Alberts |

FOREIGN PATENT DOCUMENTS

| DE | 4225488 | 2/1994 |
|---|---|---|
| EP | 0094239 | 11/1982 |
| EP | 0201352 | 11/1986 |
| EP | 0337739 | 10/1989 |
| EP | 0365328 | 4/1990 |
| EP | 1028113 | 8/2000 |
| EP | 1267171 | 12/2002 |
| EP | 0266980 | 8/2010 |
| WO | 95/01177 | 1/1995 |
| WO | 96/41013 | 12/1996 |
| WO | 97/10813 | 3/1997 |
| WO | 97/25042 | 7/1997 |
| WO | 97/28149 | 8/1997 |
| WO | 98/43081 | 10/1998 |
| WO | 99/50664 | 10/1999 |
| WO | 99/62509 | 12/1999 |
| WO | 00/30683 | 6/2000 |
| WO | 01/32167 | 5/2001 |
| WO | 01/89519 | 11/2001 |
| WO | 01/95895 | 12/2001 |

| WO | 2004/060282 | 7/2004 |
| WO | 2005/040128 | 5/2005 |
| WO | 2005/077943 | 8/2005 |
| WO | 2007/021460 | 2/2007 |
| WO | 2007/138485 | 12/2007 |
| WO | 2008/089461 | 7/2008 |
| WO | 2008/089462 | 7/2008 |
| WO | 2008/089463 | 7/2008 |
| WO | 2008/089464 | 7/2008 |
| WO | 2009/089098 | 7/2009 |

OTHER PUBLICATIONS

PCT International Search Report and Written Opinion, PCT/US2008/051521, May 21, 2008, 10 pages.

Fitzpatrick, Francis A., et al., "Influence of Thromboxane Synthetase Inhibitors on Virus Replication in Human Lung Fibroblasts in Vitro," Biochemical and Biophysical Research Communications, Oct. 1983, vol. 116, No. 1, pp. 264-271.

Foster, M.R., et al., "Effect of GR32191 and Other Thromboxane Receptor Blocking Drugs on Human Platelet Deposition onto De-Endothelialized Arteries," Thrombosis Research, 1992, vol. 65, No. 6, pp. 769-784.

Ackerley et al., "A Novel Approach to Dual-Acting Thromboxane Receptor Antagonist/Synthase Inhibitors Based on the Link of 1,3-Dioxane-Thromboxane Receptor Antagonists and -Thromboxane Synthase Inhibitors," J. Med. Chem., 38:1608-1628 (1995).

Adams et al., "Activators of Peroxisome Proliferator-activated Receptor γ Have Depot-specific Effects on Human Preadipocyte Differentiation," J. Clin. Invest, 100(12):3149-3153 (Dec. 1997).

Al-Salman et al., "Hepatocellular Injury in a Patient Receiving Rosiglitazone," Ann. Intern Med., 132:121-124 (Jan. 18, 2000).

Anzick et la., "AIB1, a Steroid Receptor Coactivator Amplified in Breast and Ovarian Cancer," Science, 277:965-968 (1997).

Beauregard et al., "Peroxisome Proliferator-Activated Receptor Agonists Inhibit Interleukin-1β-Mediated Nitric Oxide Production in Cultured Lacrimal Gland Acinar Cells," J. Ocular Pharm. and Therapeutics, 19:579-587 (Nov. 6, 2003).

Berge et al., "Pharmaceutical Salts," Journal of Pharmaceutical Sciences, 66(1):1-19 (Jan. 1977).

Bonazzi et al., "Regulation of Cyclooxygenase-2 by Hypoxia and Peroxisome Proliferators in the Corneal Epithelium," J. Biol. Chem., 275(4):2837-2844 (Jan. 28, 2000).

Börsch-Haubold et al., "Direct Inhibition of Cyclooxygenase-1 and -2 by the Kinase Inhibitors SB 203580 and PD 98059," J. Biol. Chem., 273(44):28766-28772 (Oct. 30, 1998).

Boukamp et al., "Normal Keratinization in a Spontaneously Immortalized Aneuploid Human Keratinocyte Cell Line," J. Cell Biol., 273(44):28766-28772 (1988).

Brown et al., "Improved synthetic routes to the novel thromboxaine receptor antagonist ICI 192605: activity of synthetic 1,3-dioxane intermediates," J. Pharm. Pharmacol., 42:53-55 (1990).

Brown et al., "X-Ray Crystal Structure of a Ligand at the Thromboxane A2/Prostaglandin H2 Receptor Site: (4Z)-6[(2RS,4RS,5SR)-2-92-Chlorophenyl)-4-(2-hydroxyphenyl)-1,3-dioxan-5-yl]hex-4-enoic Acid," J. Chem. Soc. Perkin Trans., 2158-2160 (1990).

Brown et al., "Design of Dual-Acting Thromboxane Antagonist-Synthase Inhibitors by a Mutual Prodrug Approach," Bioorganic & Medicinal Chemistry Letters, 6(3):273-278 (1996).

Brown et al., "ICI 180080, a novel selective thromboxane receptor antagonist: synthesis and relative activity," J. Pharm. Pharmacol., 38:706-708 (1986).

Bueno et al., "L-carnitine and propionyl-L-carnitine improve endothelial dysfunction in spontaneously hypertensive rats: Different participation of NO and COX-products," Life Sciences, 77:2082-2097 (2005).

Carroll et al., "A thrombelastograph whole blood assay for clinical monitoring of NSAID-insensitive transcellular platelet activation by arachidonic acid," J. Lab. Clin. Med. 146(1):30-35 (Jul. 2005).

Castillo et al., "An adipogenic cofactor bound by the differentiation domain of PPARγ," The EMBO Journal, 18(13):3676-3687 (1999).

Casy et al., "HPLC and 1H-NMR study of chiral recognition in some thromboxane antagonists induced by β-cyclodextrin," J. Pharm. & Biomed. Analysis, 9(10-12):787-792 (1991).

Chakravarti et al., "Role of CBP/P300 in nuclear receptor signalling," Nature, 383:99-103 (Sep. 5, 1996).

Chen et al., "A transcriptional co-repressor that interacts with nuclear hormone receptors," Nature, 377:454-457 (Oct. 5, 1995).

Cheng-Lai et al., "Rosiglitazone—an Agent from the Thiazolidinedione Class for the Treatment of Type 2 Diabetes," Heart Disease, 2:326-333 (2000).

Crankshaw, Denis, "Effects of the isoprostane, 8-3pi-prostaglandin F2α, on the contractility of the human myometrium in vitro," European Journal of Pharmacology, 285:151-158 (1995).

Daray et al., "Pharmacological characterization of prostanoid receptors mediating vasoconstriction in human umbilical vein," British Journal of Pharmacology, 139:1409-1416 (2003).

de Graaf et al., "Molecular modeling of the second extracellular loop of G-protein coupled receptors and its implication on structure-based virtual screening," Proteins, 71:599-620 (2008).

Ding et al., "Lipoxygenase and cyclooxygenase metabolism: new insights in treatment and chemoprevention of pancreatic cancer," Molecular Cancer, 2:1-12 (Jan. 7, 2003) http://www.molecular-cancer.com/content/2/1/10.

Dowell et al., "Identification of Nuclear Receptor Corepressor as a Peroxisome Proliferator-activated Receptor α Interacting Protein," J. Biol. Chem., 274(22):15901-15907 (May 28, 1999).

Dowell et al., "p300 Functions as a Coactivator for the Peroxisome Proliferator-activated Receptor α," J. Biol. Chem., 272(52):33435-33443, (Dec. 26, 1997).

Duez et al., "PPARs in inflammation, atherosclerosis and thrombosis," Journal of Cardiovascular Risk, 8(4):185-186 (Aug. 2001).

Elbrecht et al., "Molecular Cloning, Expression and Characterization of Human Peroxisome Proliferator Activated Receptors γ1 and γ2," Biochemical and Biophysical Research Communications, 224:431-437 (1996).

Ettmayer et al., "Lessons Learned from Marketed and Investigational Prodrugs," J. Med. Chem., 47(10):2393-2404 (May 6, 2004).

Faull et al., "Dual-Acting Thromboxane Receptor Antagonist/Synthase Inhibitors: Synthesis and Biological Properties of [2-Subsituted-4-(3-pyridyl)-1,3-dioxan-5-yl]alkenoic Acids," J. Med. Chem., 38:686-694 (1995).

International Search Report for WO 2008/089463 mailed on Jun. 27, 2008.

International Search Report for WO 2008/089464 mailed on Jun. 27, 2008.

Brewster et al., "(5Z)-7-(2,2-Dimethyl-4-phenyl-1,3-dioxan-cis-5-yl)heptenoic Acid: A Specific Thromboxane A2 Receptor Antagonist," J. Med. Chem., 30:67-70 (1987).

Brewster et al., "The Synthesis of a Novel Thromboxane Receptor Antagonist 4(Z)-6-(2-O-Cholorophenyl-4-O-Hydroxyphenyl-1,3,Dioxan-CIS-5-YL) Hexenoic Acid ICI 192605," Prostaglandins, 36(2):173-178 (Aug. 1988).

CID9978509, PubChem Public Chemical Database, 2 pages, Oct. 25, 2006.

Sorensen et al., U.S. Appl. No. 12/523,844, filed Jul. 20, 2009.

Sorensen et al., U.S. Appl. No. 12/523,848, filed Jul. 7, 2010.

Kristiansen et al., U.S. Appl. No. 12/161,317, filed Jul. 17, 2008.

Forman et al., "Hepatic Failure in a Patient Taking Rosiglitazone," Ann. Intern Med. 132:118-121 (Jan. 18, 2000).

Gale et al., "Lessons from the glitazones: a story of drug development," Lancet, 357:1870-1875 (Jun. 9, 2001).

Gao et al., "Hydrogen peroxide induces a greater contraction in mesenteric arteries of spontaneously hypertensive rats through thromboxane A2 production," British Journal of Pharmacology, 134:1639-1646 (2001).

Glass et al., "The coregulator exchange in transcriptional functions of nuclear receptors," Genes & Development, 14:121-141 (2000).

Hall, Steven E., "Thromboxane A2 Receptor Antagonists," Medicinal Research Reviews, 11(5):503-579 (1991).

Haskins et al., "Thiazolidinedione toxicity to isolated hepatocytes revealed by coherent multiprobe fluorescence microscopy and correlated with multiparameter flow cytometry of peripheral leukocytes," Arch Toxicol., 75:425-438 (2001).

Hedberg et al., Characterization of [5,6-3H]SQ 29,548 as a High Affinity Radioligand, Binding to Thromboxane A2/Prostaglandin H2-Receptors in Human Platelets, J. Pharm. & Exp. Ther., 245(3):786-792 (1988).

Heinlein et al., "Identification of ARA70 as a Ligand-enhanced Coactivator for the Peroxisome Proliferator-activated Receptor γ," J. Biol. Chem., 274(23):16147-16152 (Jun. 4, 1999).

Helledie et al., "Lipid-binding proteins modulate ligand-dependent transactivation by peroxisome proliferator-activated receptors and localize to the nucleus as well as the cytoplasm," Journal of Lipid Research, 41:1740-1751 (2000).

Hutchinson et al., "Effects of eicosanoids on parameters in isolated rat hepatocytes and isolated rate hepatocyte couplets: protective effects of eiocsanoid receptor antagonists," J. Lipid Mediators Cell Signalling, 15:249-254 (1997).

Iizuka et al., "Highly Selective Inhibitors of Thromboxane Synthetase. 1. Imidazole Derivatives," J. Med. Chem., 24:1139-1148 (1981).

Janssen et al., "Vasoconstrictor actions of isoprostanes via tyrosine kinase and Rho kinase in human and canine pulmonary vascular smooth muscles," British Journal of Pharmacology, 132:127-134 (2001).

Jourdan et al., "Evidence for a dilator function of 8-iso prostaglandin F2α in rat pulmonary artery," British Journal of Pharmacology, 120:1280-1285 (1997).

Kaplan et al., "PPARs, insulin resistance and type 2 diabetes," J. Cardiovascular Risk, 8:211-217 (2001).

Kawikova et al., "Bradykinin-induced release of thromboxane B2 into bronchoalveolar lavage fluid of guinea pigs: relationship to airflow obstruction," Eur. Journal of Pharmacology, 280:293-299 (1995).

Kawikova et al., "U46619 (a Thromboxane A2 Mimetic) Induces Airflow Obstruction and Airway Plasma Extravasation in the Guinea Pig: The Role of Histamine, Cyclooxygenase Metabolites, Leukotrienes and PAF," J. Pharm. & Exp. Therapeutics, 278(1):268-276 (1996).

Kodera et al., "Ligand type-specific Interactions of Peroxisome Proliferator-activated Receptor γ with Transcriptional Coactivators," J. Biol. Chem., 275(43):33201-33204 (2000).

Kopelovich et al., "Peroxisome Proliferator-activated Receptor Modulators As Potential Chemopreventive Agents," Molecular Cancer Therapeutics, 1:357-363 (Mar. 2002).

Landreth et al., "Anti-inflammatory actions of peroxisome proliferator-activated receptor gamma agonists in Alzheimer's disease," Neurobiology of Aging, 22:937-944 (2001).

Lanz et al., "A Steroid Receptor Coactivator, SRA, Functions as an RNA and is Present in an SRC-1 Complex," Cell, 97:17-27 (Apr. 2, 1999).

Lavinsky et al., "Diverse signaling pathways modulate nuclear receptor recruitment of N-CoR and SMRT complexes," PNAS USA, 95:2920-2925 (Mar. 1998).

Lebovitz, Harold E., "Differentiating members of the thiazolidinedione class: a focus on safety," Diabetes/Metabolism Research and Reviews, 18:S23-S29 (2002).

Lehmann et al., "An Antidiabetic Thiazolidinedione Is a High Affinity Ligand for Peroxisome Proliferator-activated Receptor γ (PPARγ)," J. Biol. Chem., 270(22):12953-12956 (Jun. 2, 1995).

Nagai et al., "Factor V Leiden mutation is associated with enhanced arterial thrombotic tendency in lean but not in obese mice," Thromb Haemost, 98:858-863 (2007).

Onate et al., "Sequence and Characterization of a Coactivator for the Steroid Hormone Receptor Superfamily," Science, 270:1354-1357 (Nov. 24, 1995).

Patscheke et al., "Investigations on a Selective Non-Prostanoic Thromboxane Antagonist, BM 13.177, In Human Platelets," Thrombosis Research, 33:277-288 (1984).

Pineda Torra, Ines et al., "Peroxisome proliferator-activated receptor alpha in metabolic disease, inflammation, atherosclerosis and aging," Current Opin. in Lipidology, 10:151-159 (1999).

Puigserver et al., "A Cold-Inducible Coactivator of Nuclear Receptors Linked to Adaptive Thermogenesis," Cell, 92:829-839 (Mar. 20, 1993).

Rachez et al., "Ligand-dependent transcription activation by nuclear receptors requires the DRIP complex," Nature, 398:824-828 (Apr. 29, 1999).

Rhee et al., "Active Conformation of Thromboxane A2 and Thromboxane A2 Receptor Antagonists," J. Pharm. Soc. 41(6):765-772 (1997) English Abstract Only.

Rumi et al., "Can PPARγ Ligands Be Used in Cancer Therapy?" Curr. Med. Chem—Anti-Cancer Agents, 4:465-477 (2004).

Saussy Jr. et al., "Identification of a Putative Thromboxane A2/PRostaglandin H2 Receptor in Human Platelet Membranes," J. Biol. Chem., 261(7):3025-3029 (1996).

Scheen, A. J., "Thiazolidinediones and Liver Toxicity," Diabetes Metab (Paris), 27:305-313 (2001).

Senchyna et al., "Characterizatin of the Prostanoid TP Receptor Population in Human Nonpregnant Myometrium," J. Pharm. and Exp. Therapeutics, 279(1):262-270 (1996).

Shaw et al., "Combined administration of 5-HT2 and thromboxane A2 antagonists: effects on platelet aggregation and isolated cardiac muscle," British Journal of Pharmacology, 121:875-882 (1997).

Shaw et al., "Erratum," British Journal of Pharmacology, 120:1186 (1997).

Shaw et al., "Erratum," British Journal of Pharmacology, 118:1326 (1996).

Shaw et al., "Suppression of reperfusion-induced arrhythmias with combined administration of 5-HT2 and thromboxane A2 antagonists," British Journal of Pharmacology, 117:817-822 (1996).

Smith et al., "Peroxisomes in Dermatology. Part I," J. Cutan. Med. Surg., 231-243 (2001).

Soon Tan et al., "Peroxisome proliferator-activated receptor-β as a target for wound healing drugs," Expert Opin. Ther. Targets 8(1):39-48 (2004).

Treuter et al., "A Regulatory Role for RIP140 in Nuclear Receptor Activation," Mol. Endocrinol., 12:864-881 (1998).

Wermuth et al., "Molecular Variations Based on Isosteric Replacements," The Practice of Medicinal Chemistry, Academic Press, pp. 233-237 (1996).

Xie, G. et al., "5-Hydroxytryptyamine-induced plasma extravasation in the rat knee joint is mediated by multiple prostaglandins," Inflammation Research, 52:32-38 (2003).

Yamamoto, Y. et al., "Cytotoxicity and apoptosis produced by troglitazone in human hepatoma cells," Life Sciences, 70:471-482 (2001).

Zhu et al., "Isolation and Characterization of PBP, a Protein That Interacts with Peroxisome Proliferator-activated Receptor," 272(41):25500-25506 (Oct. 10, 1997).

Zhu et al., "Isolation and Characterization of Peroxisome Proliferator-activated Receptor (PPAR) Interacting Protein (PRIP) as a Coactivator for PPAR," J. Biol. Chem., 275(18):13510-13516 (2000).

Allen, Graham D., "Modfit: a pharmacokinetics computer program," Biopharmaceutics & Drug Disposition, 11:477-498 (1990).

International Search Report for WO 2007/138485 mailed on Feb. 12, 2008.

International Search Report for WO 2008/089461 mailed on May 21, 2008.

International Search Report for WO 2008/089462 mailed on Jul. 2, 2008.

*Primary Examiner* — Andrew D Kosar
*Assistant Examiner* — Raymond Covinton
(74) *Attorney, Agent, or Firm* — McDonnell Boehnen Hulbert & Berghoff LLP

(57) ABSTRACT

Specifically useful stereoisomers of 1,3-dioxane derivatives are described and their use in the treatment of a disease or condition dependent on PPAR modulation, such as diabetes, cancer, inflammation, neurodegenerative disorders and infections as well as their use in the treatment of a disease related to TP, such as cardiovascular diseases.
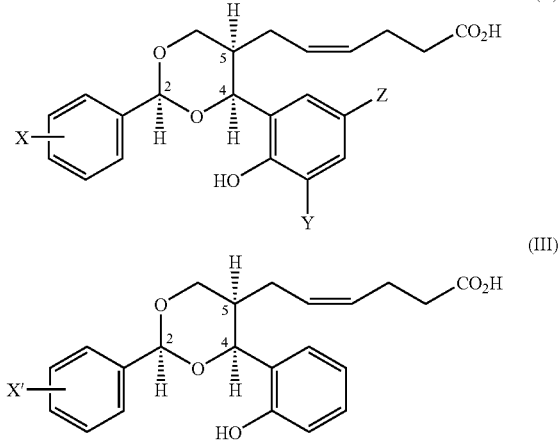
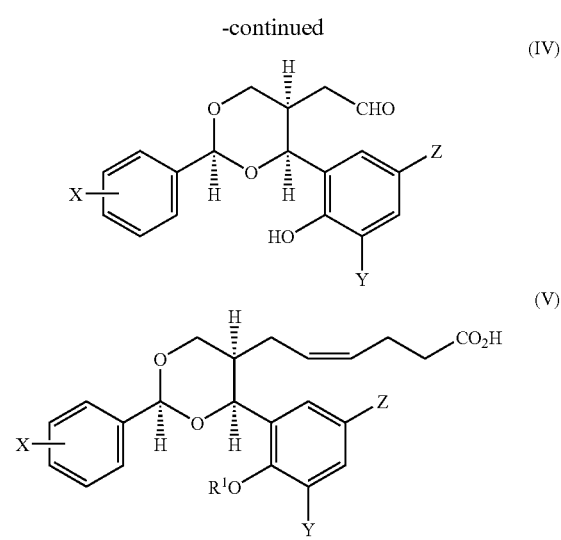
19 Claims, 16 Drawing Sheets

II

III

IV

V

VI

VII

VIII

JK-356-3-1

SUBSTITUTED 1,3-DIOXANES USEFUL AS PPAR MODULATORS

CROSS-REFERENCE TO RELATED APPLICATIONS

This application is the National Stage of and claims priority to International Application No. PCT/US2008/051521, filed Jan. 18, 2008, and claims benefit of PCT Application No. PCT/IB2007/002542, filed Jan. 18, 2007, U.S. provisional Application No. 60/989,808, filed on Nov. 21, 2007, U.S. provisional Application No. 60/989,806, filed on Nov. 21, 2007, and U.S. provisional Application No. 60/989,805, filed on Nov. 21, 2007, all of which are incorporated by reference in their entirety.

FIELD OF INVENTION

The present invention is directed to a specific group of 2,4-diphenyl-1,3-dioxanes capable of modulating PPAR activity (also referred herein to as "PPAR modulators"). The substituted 1,3-dioxanes of the invention are useful in the treatment of a disease or condition dependent on PPAR modulation, such as diabetes, cancer, inflammation, neurodegenerative disorders and infections. The dioxanes of the invention are also useful in modulating, in particular antagonizing, the activity of the thromboxane receptor (thromboxane prostanoid receptor, i.e. the TP receptor) and/or inhibiting thromboxane synthase. The thromboxane receptor, the thromboxane A2 receptor or prostaglandin H2 receptor are each referred to herein as "TP receptor" in accordance with the convention set forth in the IUPHAR compendium of receptor characterization and classification 1998, page 239, and The Sigma-RBI Handbook 5th edition, Prostanoid receptors, 2006, pages 138-140. The preferred compounds of the invention are also referred to as PPAR modulators, TP receptor antagonists and thromboxane synthase (TS) inhibitors.

BACKGROUND OF INVENTION

Peroxisome proliferator-activated receptors (PPAR) are nuclear hormone receptors. PPAR receptors activate transcription by binding to elements of DNA sequences, known as peroxisome proliferator response elements (PPRE), in the form of a heterodimer with retinoid X receptors (known as RXRs). Three sub-types of human PPAR have been identified and described: PPAR-alpha, PPAR-gamma and PPAR-delta (or NUCI). PPAR-alpha is mainly expressed in the liver, while PPAR-delta is ubiquitous. PPAR-gamma is involved in regulating the differentiation of adipocytes, where it is highly expressed. It also has a key role in systemic lipid homeostasis. A number of compounds that modulate the activity of PPARs have been identified including thiazolidinediones, which have been employed in the treatment of diabetes.

The DNA sequences of the PPAR-gamma subtypes are described in Elbrecht et al., BBRC 224; 431-437 (1996). Peroxisome proliferators including fibrates and fatty acids activate the transcriptional activity of PPARs.

Numerous examples are provided in the literature illustrating that PPARs are closely involved in a wide array of diseases or pathological conditions which are associated with cells expressing these nuclear receptors. More specifically, PPARs are useful as drug target in methods for reducing blood glucose, cholesterol and triglyceride levels and are accordingly explored for the treatment and/or prophylaxis of insulin resistance, dyslipidemia, and other disorders related to Syndrome X (also designated "the metabolic syndrome) (WO 97/25042, WO 97/10813, WO 97/28149; see also Kaplan et al., 2001, J Cardiovasc Risk, 8, 211-7) including obesity and atherosclerosis (Duez et al., 2001, J. Cardiovasc. Risk, 8, 185-186), coronary artery disease and certain other cardiovascular disorders. Further, PPARs have been shown to be potential targets for the treatment of certain inflammatory diseases such as cutaneous disorders (see Smith et al., 2001, J. Cutan. Med. Surg., 5, 231-43), gastrointestinal diseases (WO 98/43081) or renal diseases including glomerulonephritis, glomerulosclerosis, nephrotic syndrome and hypertensive nephrosclerosis. Similarly PPARs are useful for improving cognitive functions in neurologic diseases (Landreth and Heneka, 2001, Neurobiol Aging, 22, 937-44) or in dementia, for treating psoriasis, polycystic ovarian syndrome (PCOS) or for preventing and treating bone loss, e.g. osteoporosis (see for example U.S. Pat. Nos. 5,981,586 or 6,291,496).

Thus, PPARs are exciting targets for the development of therapeutic compounds. Although, the responses observed in the context of the various methods for treating and/or preventing diseases or pathological conditions are encouraging for example, the thiazolidinedione, TZD, class of medications (e.g., rosiglitazone or pioglitazone) unambiguously plays a critical role in improving insulin sensitivity in patients with type 2 diabetes (see Cheng lai and Levine, 2000, Heart Dis., 2, 326-333), they are not fully satisfactory treatments because of the occurrence of numerous serious undesirable side effects (for example, weigh gain, hypertension, cardiac hypertrophy, haemodilution, liver toxicity and oedema; see Haskins et al., 2001, Arch Toxicol., 75, 425-438; Yamamoto et al., 2001, Life Sci., 70, 471-482; Scheen, 2001, Diabetes Metab., 27, 305-313; Gale, 2001, Lancet, 357, 1870-1875; Forman et al., 2000, Ann. Intern. Med., 132, 118-121 and A1 Salman et al., 2000, Ann. Intern. Med., 132, 121-124). Consequently, it is desirable to identify novel improved products and/or novel methods which enable the treatment and/or the prevention of diseases or pathological conditions associated with cell types that express PPAR nuclear receptors. More specifically, most of the side effects observed with TZD derivatives are attributable to the full-agonist properties of said compounds and thus it is desirable to identify new compounds that are not necessarily full-agonists.

The thromboxane receptor is involved in blood platelet aggregation and has been implicated in vasoconstriction, as well as in bronchial and tracheal smooth muscle constriction. European patent application, publication No. 94239; European patent application, Publication No. 0 266 980 and U.S. Pat. No. 4,895,962 name certain 4-phenyl-1,3-dioxan-5-ylalkenoic acid derivatives and describe their potential utility as thromboxane receptor antagonists. Additional compounds for modulating thromboxane receptors and/or peroxisome-activated receptors (PPAR) and for the treatment and prevention of diseases associated with them are needed.

SUMMARY OF THE INVENTION

The present invention relates to compounds capable of modulating the activity of one or more of PPAR (in particular PPAR gamma), the TP receptor and thromboxane synthase (TS), preferably of all three. In addition the invention relates to various uses of these compounds in the treatment of a number of clinical conditions specified herein below.

In one aspect the invention relates to compounds of formula X

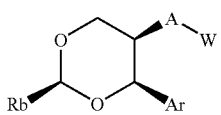

Formula X wherein

A is a branched or linear carbon chain of 3 to 7 carbons, optionally containing 1 or 2 double bonds; and W is COOH, C(O)NH—OH, $NH_2$, $SO_3H$, $OSO_3H$, an aromatic group (optionally substituted with COOH, OH or $NH_2$) or —C(O)—Rd, wherein Rd is —NH—$C_{1-6}$-alkyl (branched or linear, preferably linear), —O—$C_{1-6}$-alkyl (branched or linear, preferably linear), a saccharide or —OH; and Ar is a phenyl, or a 5 or 6 membered heterocyclic aromatic group optionally substituted with O—Rc, wherein Rc is $C_{1-6}$-alkyl (branched or linear, preferably linear), —C(O)—$C_{1-6}$-alkyl (branched or linear, preferably linear), —CH(O), a saccharide or H; and Rb is 2-6C alkenyl, 1-8C alkyl optionally substituted with up to three halogeno substiuents, saccharide, pentafluorophenyl, aryl or aryl(1-4C)alkyl, the latter two of which may optionally have up to five substituents selected from halogeno, (1-6C)alkyl, branched or linear (1-6C)alkoxy, (1-4C) alkylenedioxy, trifluoromethyl, cyano, nitro, hydroxyl, (2-6C)alkanoyloxy, (1-6C)alkylthio, (1-6C)alkanesulphonyl, (1-6C)alkanoylamino and oxapolymethylene of 2 to 4 carbon atoms.

In addition the invention relates to compounds of formula XI:

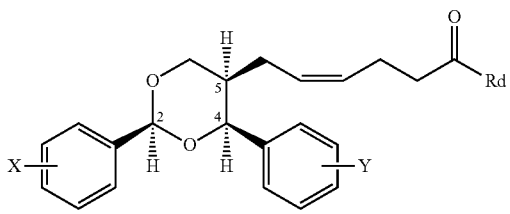

Formula XI wherein

X is selected from the group consisting of fluoro, chloro, bromo, trifluoromethyl, substiuted phenyl, cyano, methoxy, nitro, hydroxyl and —H; and Y is selected from the group consisting of fluoro, chloro, bromo, trifluoromethyl, substiuted phenyl, cyano, methoxy, nitro, hydroxyl, —C(O)-sacharide and —H; and Rd is —NH—$C_{1-6}$-alkyl (branched or linear, preferably linear), —O—$C_{1-6}$-alkyl (branched or linear, preferably linear), a saccharide or —OH.

The invention furthermore relates to compounds of formula XIII:

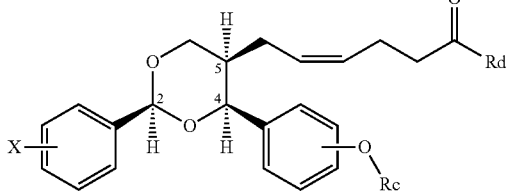

Formula XIII wherein X is selected from fluoro, chloro, bromo, trifluoromethyl, optionally substituted phenyl, cyano, methoxy and nitro; and Rc is $C_{1-6}$-alkyl (branched or linear, preferably linear), —C(O)—$C_{1-6}$-alkyl (branched or linear, preferably linear), —CH(O), a saccharide or —H; and Rd is —NH—$C_{1-6}$-alkyl (branched or linear, preferably linear), —O—$C_{1-6}$-alkyl (branched or linear, preferably linear), glycosyl or —OH.

These compounds may for example be useful in the treatment or prevention of a clinical condition selected from the group consisting of the metabolic syndrome, obesity, insulin resistance, pre-diabetes, diabetes, dyslipidemia, autoimmune disease such as multiple sclerosis, psoriasis, atopic dermatitis, asthma and ulcerative colitis, cancer such as liposarcoma, neuroblastoma, bladder, breast, colon, lung, pancreas and prostate; inflammation, infections, AIDS and wound healing.

In addition these compound may for example be useful in the treatment or prevention of a clinical condition is selected from the group consisting of myocardial infarction, thrombosis, thrombotic disorders, pulmonary hypertension, atherosclerosis, diabetic nephropathy, retinopathy, peripheral arterial disease, lower limb circulation, pulmonary embolism, thrombus formation, stent-triggered thrombus formation, stent induced restenosis, hyperplasia, stent-triggered hyperplasia, septic shock, preeclampsia, asthma, rhinitis, allergic rhinitis, tumour angiogenesis and metastasis.

DETAILED DESCRIPTION OF THE INVENTION

Definitions

Figure 1:
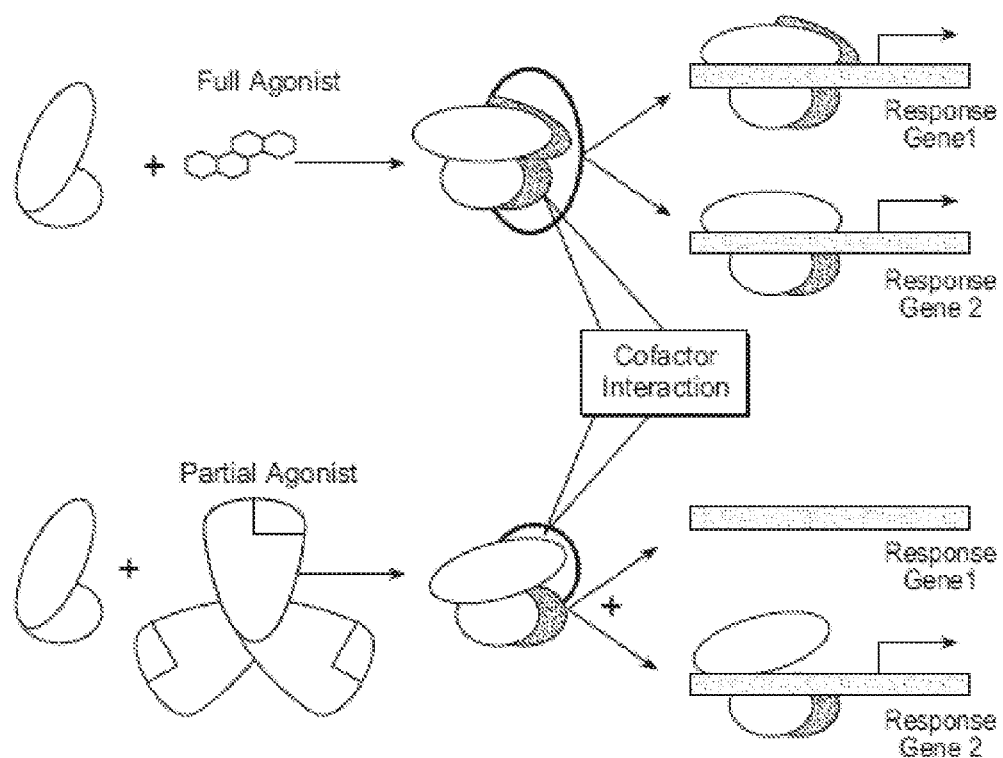
FIG. 1 illustrates a model of PPAR activation by a full agonist and a partial agonist, respectively.

In general the terms used herein will take their standard definitions that one of ordinary skill in the pharmaceutical, biological and chemical arts would employ in understanding the invention. The following terms have the meanings given, and other terms may be provided in the specifications.

Alkyl: The term "alkyl" refers to a monovalent, saturated aliphatic hydrocarbon radical having the indicated number of carbon atoms, generally one to twenty two. For example, a "1-8C alkyl" or an "alkyl of 1-8 carbons" or "Alk 1-8" would refer to any alkyl group containing one to eight carbons in the structure. Alkyl may be a straight chain (i.e. linear) or a branched chain. Lower alkyl refers to an alkyl of 1-6 carbons. Representative examples of lower alkyl radicals include methyl, ethyl, n-propyl, n-butyl, n-pentyl, n-hexyl, isopropyl, isobutyl, isopentyl, amyl, sec-butyl, tert-butyl, sec-amyl, tert-pentyl, 2-ethylbutyl, 2,3-dimethylbutyl, and the like. Higher alkyl refers to alkyls of seven carbons and above. These include n-heptyl, noctyl, n-nonyl, n-decyl, n-dodecyl, n-tetradecyl, n-hexadecyl, n-octadecyl, n-eicosyl, and the like, along with branched variations thereof. A linear carbon chain of 3 to 7 carbons would refer to the chain length, not including any carbons residing on a branch. The radical may be optionally substituted.

Alkenyl: The term "alkenyl" refers to a monovalent, aliphatic hydrocarbon radical having at least one carbon-carbon double bond and having the indicated number of carbon atoms. For example, a "$C_{2-6}$ alkenyl" or an "alkenyl of 1-6 carbons," or "alkenyl 1-6" would refer to an alkenyl group containing one to six carbon atoms in the structure. Alkenyl may be a straight chain (i.e., linear) or a branched chain. Lower alkenyl refers to an alkenyl of 1-6 carbons. Representative examples of lower alkenyl radicals include ethenyl, 1-propenyl, 1-butenyl, 1-pentenyl, 1-hexenyl, isopropenyl, isobutenyl, and the like. Higher alkenyl refers to alkenyls of seven carbons and above. These include 1-heptenyl, 1-octenyl, 1-nonenyl, 1-decenyl, 1-dodecenyl, 1-tetradecenyl, 1-hexadecenyl, 1-octadecenyl, 1-eicosenyl, and the like, along with branched variations thereof. The radical may be optionally substituted.

Alkoxy: The term "alkoxy" refers to a monovalent radical of the formula RO—, where R is an alkyl as defined herein. Lower alkoxy refers to an alkoxy of 1-6 carbon atoms or (1-6)alkoxy. Representative lower alkoxy radicals include methoxy, ethoxy, n-propoxy, n-butoxy, npentyloxy, n-hexyloxy, isopropoxy, isobutoxy, isopentyloxy, amyloxy, sec-butoxy, tert-butoxy, tert-pentyloxy, and the like. The radical may be optionally substituted Aryl: The term "aryl" as used herein denotes a monovalent aromatic carbocyclic radical containing 5 to 15 carbon atoms consisting of one individual ring, or one or more fused rings in which at least one ring is aromatic in nature, which can optionally be substituted with one or more, preferably one or three substituents independently selected from hydroxy, thio, cyano, alkyl, alkoxy, lower haloalkoxy, alkylthio, oxo, halogen, haloalkyl, hydroxyalkyl, nitro, alkoxycarbonyl, amino, alkylamino, dialkylamino, aminoalkyl, alkylaminoalkyl, and dialkylaminoalkyl, thioalkyl, alkylsulfonyl, arylsulfinyl, alkylaminosulfonyl, arylaminosulfonyl, alkylsulfonylamino, arylsulfonylamino, carbamoyl, alkylcarbamoyl and dialkylcarbamoyl, arylcarbamoyl, alkylcarbonylamino, arylcarbonylamino, unless otherwise indicated. Alternatively two adjacent atoms of the aryl ring may be substituted with a methylenedioxy or ethylenedioxy group. Thus a bicyclic aryl substituents may be fused to a heterocyclyl or heteroaryl ring; however, the point of attachment of bicyclic aryl substituent is on the carbocyclic aromatic ring. Examples of aryl radicals include, phenyl, naphthyl, benzyl, biphenyl, furanyl, pyridinyl, indanyl, anthraquinolyl, tetrahydronaphthyl, 3,4-methylenedioxyphenyl, 1,2,3,4-tetrahydroquinolin-7-yl, 1,2,3,4-tetrahydroisoquinoline-7-yl, a 1,3 dioxolane radical, a benzoic acid radical, a furan-2-carboxylic acid radical, a 2-(isoxazol-5-yl)acetic acid radical, a 3-hydroxy-2-methylpyridine-4-carboxylic acid radical and the like.

Halo: A "halo" substitutent is a monovalent halogen radical chosen from chloro, bromo, iodo, and fluoro. A "halogenated" compound is one substituted with one or more halo substituent.

Phenyl: A "phenyl" is a radical formed by removal of a hydrogen from a benzene ring. The phenyl may be optionally substituted.

Phenoxy: A "phenoxy" group is a radical of the formula RO—, wherein the R is a phenyl radical.

Benzyl: A "benzyl" group is a radical of the formula R—$CH_2$—, wherein the R is a phenyl radical.

Benzyloxy: A "benzyloxy" group is a radical of the formula RO—, wherein R is a benzyl radical.

Heterocycle: A "heterocycle" or "heterocyclic entity" is a monovalent radical of a 5- or 6-member closed ring containing carbon and at least one other element, generally nitrogen, oxygen, or sulfur and may be fully saturated, partially saturated, or unsaturated (i.e., aromatic in nature). Generally the heterocycle will contain no more than two hetero atoms. Representative examples of unsaturated 5-membered heterocycles with only one hetero atom include 2- or 3-pyrrolyl, 2- or 3-furanyl, and 2- or 3-thiopenyl. Corresponding partially saturated or fully saturated radicals include 3-pyrrolin-2-yl, 2- or 3-pyrrolindinyl, 2- or 3-tetrahydrofuranyl, and 2- or 3-tetrahydrothiophenyl. Representative unsaturated 5-membered heterocyclic radicals having two hetero atoms include imidazolyl, oxazolyl, thiazolyl, pyrazolyl, and the like. The corresponding fully saturated and partially saturated radicals are also included. Representative examples of unsaturated 6-membered heterocycles with only one hetero atom include 2-, 3-, or 4-pyridinyl, 2H-pyranyl, and 4H-pryanyl. Corresponding partially saturated or fully saturated radicals include 2-, 3-, or 4-piperidinyl, 2-, 3-, or 4-tetrahydropyranyl and the like. Representative unsaturated 6-membered heterocyclic radicals having two hetero atoms include 3- or 4-pyridazinyl, 2-, 4-, or 5-pyrimidinyl, 2-pyrazinyl, morpholino, and the like. The corresponding fully saturated and partially saturated radicals are also included, e.g. 2-piperazine. The heterocyclic radical is bonded through an available carbon atom or hetero atom in the heterocyclic ring directly to the entity or through a linker such as an alkylene such as methylene or ethylene. The heterocycle may be optionally substituted in the same way as aryl groups.

Optionally substituted: If a radical is referred to as "optionally substituted," it means that the radical is unsubstituted or at least one-H of the radical is removed and another substituent inserted in its place. The radical may be optionally substituted with substituents at positions that do not significantly interfere with the preparation of compounds falling within the scope of this invention and that do not significantly adversely affect the biological activity of the compounds. The radical is optionally substituted with one, two, three, four or five substituents independently selected from the group consisting of halo, lower alkoxy, hydroxyl, cyano, nitro, amino, halo lower alkyl, halo lower alkoxy, hydroxycarbonyl, lower alkoxycarbonyl, lower alkylcarbonyloxy, and lower alkylcarbonylamino, or as referred to hereinabove.

The term "hydroxycarbonyl" is a monovolent radical having the formula —C(O)OH.

The term "lower alkoxycarbonyl" is a monovalent radical with the formula —C(O)OAlk, where Alk is lower alkyl.

The term "lower alkylcarboxyloxy" is a monovalent radical with the formula —OC(O)Alk, where Alk is lower alkyl.

As used herein, the terms "a sugar" or "a saccharide" are used interchangeably and mean a monosaccharide, a disaccharide or a polysaccharide. Suitable monosaccharides include pentose, hexose, or heptose residues. Non-limiting examples of pentoses include arabinose, ribose, ribulose, xylose, lyxose, and xylulose. Non-limiting examples of hexoses include glucose, galactose, fructose, fucose, mannose, allose, altrose, talose, idose, psicose, sorbose, rhamnose and tagatose. Non-limiting examples of heptoses include mannoheptulose and sedoheptulose. A sugar moiety may be linked to the compound at any position of the sugar ring which can form an amide or ester bond. Preferred saccharides are beta-glycosyl saccharides.

PPAR modulation is defined by reference to the natural situation, i.e. the basal level of PPAR dependent transcription of target genes in the absence of ligands, wherein modulation of PPAR activity is reflected by a decrease or increase in said basal level of transcription in the presence of a compound capable of modulating PPAR activity. Generally, an increase of said transcription is associated with an enhancement of PPAR activity and relates to compounds named activators or agonists. Conversely, a decrease of said transcription is associated with an inhibition of PPAR activity and relates to compounds named inhibitors or antagonists. Partial agonists are compounds that result in PPAR dependent transcription of a subset of target genes while having no effect on other PPAR target genes. Partial agonists may be viewed from a biochemical or a physiological viewpoint. The biochemical view of a partial agonist is a compound that can compete out a full agonist and has a lower level of transactivation relative to a full agonist. The physiological view of a partial agonist relates to the activation of different subsets of genes (even full activation of some target genes and no activation of other PPAR target genes). This results in only some of the physiological effects of a full agonist, which is highly desirable.

A "therapeutically effective amount" of compound means the amount that, when administered to a subject in need thereof, will produce the desired result over time for the condition being treated. For example, the desired effect can be PPAR modulation and the biological activity associated therewith.

The compounds useful in this invention are depicted by various formulae in this application. By viewing the formulae, it will be apparent that the compounds often will have one or more chiral centers, i.e., a carbon to which four different groups are attached, and these can exist as enantiomers and diastereoisomers. In addition, because of the presence in some cases of double bonds, a compound will have hindered rotation. The compound thus exhibits geometric isomerism, i.e. two forms can differ from each other in the way the atoms are oriented in space. With regard to double bonds, stereoisomers exist which are referred to as diastereomers. Diastereomers (or diastereoisomers) are stereoisomers that are not enanti-omers (mirror images of each other). In naming the compounds in this application, the Chemical Abstracts Service system is used in which the two groups attached to each end of the double bond are provided a priority number as is done in naming enantiomers in the R, S system. When two groups of the higher priority number are on the same side, the molecule is the Z isomer. (German-zusammen, together). The molecule is E when on opposite sides (German-entgegen, opposite). It should be understood that the formulae are intended to encompass all of the possible enantiomers and diastereomers, whether alone or in mixture. Formulae indicating a specific stereochemistry should be understood as covering only the specific stereoisomer shown.

Compounds Useful in the Invention

The invention is based in part on the identification of compounds that are capable of modulating the activity of at least one PPAR subtype, for example PPAR gamma or PPAR beta/delta. These compounds are useful to treat conditions or diseases in mammals, such as humans, mediated by the function of such PPARs. In another embodiment, the compounds of the invention are capable of modulating the activity of the TP receptor, in particular antagonizing TP receptor activity. Compounds of the invention exhibiting both PPAR modulation and TP receptor modulation are referred to as "PPAR/TP receptor modulators". In a further embodiment, the compounds of the invention are capable of inhibiting thromboxane synthase (TS). Compounds exhibiting two or three of these activities are particularly desirable for some applications, for example and without limitation, treating cardiovascular complications in diabetic patients.

The compounds that are useful in this invention are 1,3-dioxane derivatives or a pharmaceutically acceptable salt thereof, wherein the derivative is represented by formula I:

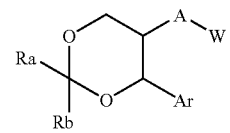

wherein

A is a branched or linear carbon chain of 2 to 7, or 3 to 7 carbons, each optionally containing 1 or 2 double bonds (each can be cis or trans)

W is COOH, OH, $NH_2$, $SO_3H$, $OSO_3H$, an aromatic group such as, but not limited to, phenyl, 1- or 2-naphthyl, pyridine, furan, 2-methylpyridine, optionally substituted with COOH, OH or $NH_2$, for example; or a 1,3 dioxolane group linked through the 2 position Ar is a phenyl, or a 5 or 6 membered heterocyclic aromatic group, such as, but not limited to, 2-pyridine, 3-pyridine, thiophene, furan, 1-naphthyl, 2-naphthyl, biphenyl and (4-methoxyphenoxy)-phenyl, the phenyl and naphthyl moieties optionally substituted with OH or OMe, in the ortho, meta and/or para position, but preferably if substituted, mono substituted in the ortho position with OH or OMe and, Ra and Rb are independently hydrogen, 2-6C alkenyl, 1-8C alkyl optionally with up to three halogeno substituents, pentafluorophenyl, aryl or aryl(1-4C)alkyl, the latter two of which may optionally have up to five substituents selected from halogeno, (1-6C)alkyl, branched or linear (1-6C) alkoxy, (1-4C)alkylenedioxy, trifluoromethyl, cyano, nitro, hydroxyl, (2-6C)alkanoyloxy, (1-6C)alkylthio, (1-6C)alkanesulphonyl, (1-6C)alkanoylamino and oxapolymethylene of 2 to 4 carbon atoms, or Ra and Rb together form polymethylene of 2 to 7 carbon atoms, optionally having one or two (1-4C)alkyl substituents.

In some embodiments, A is a linear carbon chain of 3 to 7 carbons, and W is COOH. Such a carbon chain may include a double bond between $C_2$-$C_3$ or $C_3$-$C_4$, for example.

In one embodiment Ra is H and Rb is an aromatic moiety such as phenyl, benzyl, 2- or 3- or 4-pyridine, furan, biphenyl, 1- or 2-naphthyl, bearing up to five different substituents selected from the group consisting of halogen, OH, O-alkyl, amino, N-monoalkyl, N-dialkyl (branched or linear), nitro and thioalkyl (branched or linear).

In some embodiments, the derivative is a 2,4-diphenyl-1,3-dioxane derivative or a pharmaceutically acceptable salt thereof, wherein the derivative is represented by formula II:

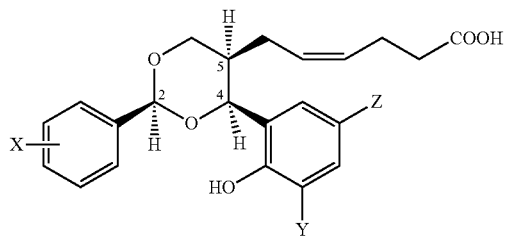

wherein X is selected from fluoro, chloro, bromo, trifluoromethyl, optionally substituted phenyl, cyano, methoxy and nitro, or the phenyl-X group can be an optionally substituted chromen derivative; and Y and Z are individually hydrogen or halogeno.

Typically, the groups at positions 2, 4 and 5 of the dioxane ring in the derivative represented by formula I will have cis-relative stereochemistry.

Other specific substitutions of the phenyl moeity bearing X which are of particular interest include, for example wherein X is 2-fluoro-, 2-chloro-, 2-bromo-, 2-cyano-, 2-trifluoromethyl-, 3-fluoro-, 3-chloro-, 3-cyano-, 3-nitro-, 3-methoxy-, 4-chloro-, 4-cyano-, 4-nitro- and 4-methoxy-phenyl.

A preferred substitution for Y is hydrogen or fluoro and for Z is hydrogen.

A preferred group of compounds useful in the invention comprises those compounds of formula III (set out hereinafter)

Formula III

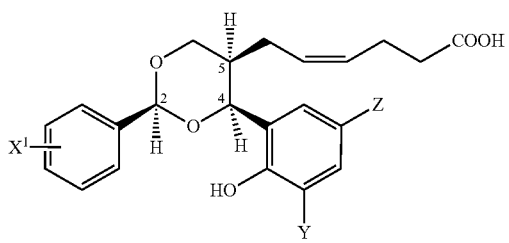

wherein $X^1$ is selected from 2-chloro, 3-chloro, 2-cyano, 4-cyano, 3-nitro and 4-nitro; and the groups at positions 2, 4 and 5 of the dioxane ring have cis-relative stereochemistry; together with the pharmaceutically acceptable salts thereof. The compounds of formula III thus include both of the enantiomer below:

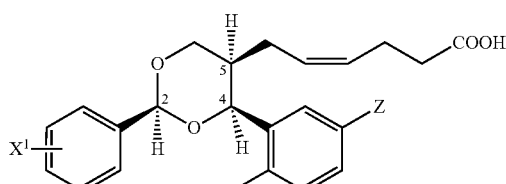

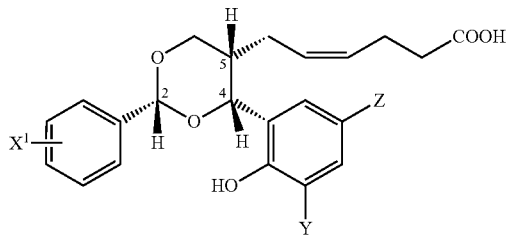

The invention also provides compounds of formula I, where A, W and Ar are defined as above and wherein Ra is H and Rb is an aryl group or a heterocycle, such as where one carbon atom of the aryl moiety is replaced by one oxygen or nitrogen atom. Such aryl and heterocycle groups can be optionally substituted with three different substituents selected from the group consisting of halogen, OH, O-alkyl (branched or linear), O-aryl, amino or N-monoalkyl or N-dialkyl (branched or linear) or N-monoaryl or N-diaryl, nitro, thioalkyl (branched or linear) or oxo (e.g SN13 in Table II). Compounds of formula I where Ra is H and Rb is a heterocycle or a phenyl group substituted with O-aryl are of particular interest, especially when Ar is phenyl substituted in the o-position by OH or OMe, W is COOH and A is a five carbon linear chain with one double bond. Illustrative examples of such compounds include compounds of formula I, where Ra is H and Rb is (4-methoxyphenoxy)-phenyl linked to the dioxane ring through the 2 or ortho position of the phenyl, such as (Z)-6-(2-[4-methoxyphenoxy-o-phenyl]-4-o-hydroxyphenyl-1,3-dioxan-cis-5-yl)hex-4-enoic acid]; or Rb is 6-chloro-4H-chromen-4-one (for example, linked to the dioxane ring through the 3 position of the chromene moiety), such as (Z)-6-(2-3-[6-chloro-4H-chromen-4-one 6-chloro-4-oxo-4H-chromen-3-yl]-4-(2-hydroxyphenyl-1,3-dioxan-cis-5-yl)hex-4-enoic acid or Rb is biphenyl, linked to the dioxane ring through the 2 or ortho position of biphenyl. Thus the invention provides the compounds referred to in this embodiment and their pharmaceutically relevant salts, alone and in combination with a pharmaceutical carrier and optionally with a further therapeutically active ingredient.

It will be appreciated that the compounds of formula I and formula II possess asymmetric carbon atoms and may exist and be isolated in racemic and optically active forms. The invention includes both the racemic forms and any optically active form (or mixtures thereof) which is capable of modulating PPAR activity, antagonizing TP receptor activity and/or inhibiting TS, and their respective uses, it being well known in the art how to assess biological properties using one or more of the assays referred to herein after.

Unless otherwise clear from the context, the chemical formulae referred to herein may be shown in a particular configuration, but this does not necessarily correspond to the absolute configuration.

Particular pharmaceutically acceptable salts of acids of formula I or II are, for example, alkali metal and alkaline earth metal salts such as lithium, sodium potassium, magnesium and calcium salts, aluminium and ammonium salts, and salts with organic amines and quaternary bases forming physiologically acceptable cations such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide, tert-butylamine and benzyltrimethylammonium hydroxide.

The most preferred compounds according to the invention are PPAR modulators, TP receptor antagonist or TS inhibitors, or compounds exhibiting two or more of these activities. Preferred compounds described by formula IX, will therefore exhibit one or more of these activities, wherein Formula IX is

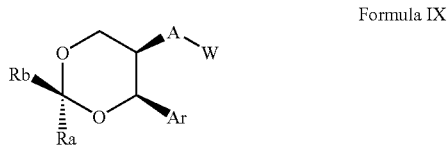

Formula IX and wherein substituents Ra, Rb, A, W and Ar are as defined herein above in relation to compounds of formula I, or any of the aforementioned. The specific stereochemistry of the compounds of formula IX is important and is as indicated in said formula.

More preferred compounds of formula IX include those wherein Ra is H and are PPAR modulators, TP receptor antagonists or TS inhibitors, or compounds exhibiting two or more of these activities. Thus, preferred compounds are of formula X:

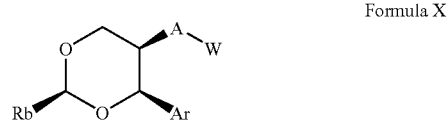

Formula X wherein substituents Rb, A, W and Ar are as defined herein above in relation to compounds of formula I. The specific stereochemistry of the compounds of formula X is important and is as indicated in said formula.

Preferred PPAR modulators, TP receptor antagonists and/or TS inhibitors are compounds of formula X with the following substituents:

Rb is preferably phenyl, which optionally is substituted with up to five substituents, preferably 4, more preferably 3, even more preferably 2, yet more preferably 1 substituent(s) selected from the group consisting of halogeno, (1-6C)alkyl, branched or linear (1-6C)alkoxy, (1-4C)alkylenedioxy, trifluoromethyl, cyano, nitro, hydroxyl, (2-6C)alkanoyloxy, (1-6C)alkylthio, (1-6C)alkanesulphonyl, (1-6C)alkanoylamino and oxapolymethylene of 2 to 4 carbon atoms. More preferably Rb is phenyl substituted with one substituent selected from the group consisting of fluoro, chloro, bromo, trifluoromethyl, substiuted phenyl, cyano, methoxy and nitro, preferably from the group consisting of fluoro, chloro, bromo and trifluoromethyl. Preferably, said phenyl is substituted at the ortho position.

Ar is preferably phenyl optionally substituted with up to five substituents, preferably 4, more preferably 3, even more preferably 2, yet more preferably 1 substituent(s) selected from the group consisting of halogeno, (1-6C)alkyl, branched or linear (1-6C)alkoxy, (1-4C)alkylenedioxy, trifluoromethyl, cyano, nitro, hydroxyl, (2-6C)alkanoyloxy, (1-6C)alkylthio, (1-6C)alkanesulphonyl, (1-6C)alkanoylamino and oxapolymethylene of 2 to 4 carbon atoms, more preferably from the group consisting of OH, (1-6C)alkoxy and halogeno. Even more preferably Ar is phenyl substituted with —OH or —OMe, in the ortho, meta and/or para position, but preferably mono substituted in the ortho position with OH or OMe.

A is a linear carbon chain of 3 to 7 carbons, preferably of 5 to 6 carbons, more preferably of 5 carbons containing 1 double bond, which preferably is a cis double bond. For carbon chains of 5 to 6 carbons said double bond is preferably positioned in the 2 position (i.e., between C2 and C3, counted from the dioxane ring).

In one embodiment preferred compounds according to the invention are PPAR modulators, TP receptor antagonists, TS inhibitors or compounds with 2 or 3 such activities having formula X, wherein A is a branched or linear carbon chain of 3 to 7 carbons, optionally containing 1 or 2 double bonds (each can be cis or trans), preferably A is a linear carbon chain of 5 to 6 carbons containing 1 double bond, which preferably is a cis double bond, even more preferably A is a linear carbon chain of 5 carbons containing one cis double bond, and W is COOH, C(O)NH—OH, $NH_2$, $SO_3H$, $OSO_3H$, an aromatic group such as, but not limited to, phenyl, 1- or 2-naphthyl, pyridine, furan, 2-methylpyridine, optionally substituted with COOH, OH or $NH_2$, for example; a 1,3 dioxolane group linked through the 2 position or —C(O)-Rd, wherein Rd is —NH—$C_{1-6}$-alkyl (branched or linear, preferably linear), —O—$C_{1-6}$-alkyl (branched or linear, preferably linear), a saccharide (preferably a mono- or disaccharide, more preferably, a monosaccharide, even more preferably glycosyl) or —OH, preferably W is —C(O)—Rd, wherein Rd is —OH, glycosyl or —O—$CH_3$, more preferably —OH or —O—$CH_3$, and Ar is a phenyl, or a 5 or 6 membered heterocyclic aromatic group, such as, but not limited to, 2-pyridine, 3-pyridine, thiophene, furan, 1-naphthyl, 2-naphthyl, biphenyl and (4-methoxyphenoxy)-phenyl, the phenyl and naphthyl moieties optionally substituted with O—Rc, in the ortho, meta and/or para position, but preferably if substituted, mono substituted in the ortho position with O—Rc, wherein Rc is $C_{1-6}$-alkyl (branched or linear, preferably linear), —C(O)—$C_{1-6}$-alkyl (branched or linear, preferably linear), —CH(O), a saccharide (preferably a mono- or disaccharide, more preferably, a monosaccharide, even more preferably glycosyl) or —H, preferably Ar is phenyl substituted at in the ortho position with —O—Rc, wherein Rc is methoxy, —C(O)—$CH_3$, or —H, and Rb is 2-6C alkenyl, 1-8C alkyl optionally substituted with up to three halogeno substiuents, saccharide, pentafluorophenyl, aryl or aryl(1-4C)alkyl, the latter two of which may optionally have up to five substituents selected from halogeno, (1-6C)alkyl, branched or linear (1-6C)alkoxy, (1-4C)alkylenedioxy, trifluoromethyl, cyano, nitro, hydroxyl, (2-6C)alkanoyloxy, (1-6C)alkylthio, (1-6C)alkanesulphonyl, (1-6C)alkanoylamino and oxapolymethylene of 2 to 4 carbon atoms, preferably Rb is phenyl substituted with halogeno, even more preferably with chloro, preferably in the ortho position.

Preferred PPAR modulators, TP receptor antagonists and/or TS inhibitors according to the present invention are compounds of formula XI:

Formula XI

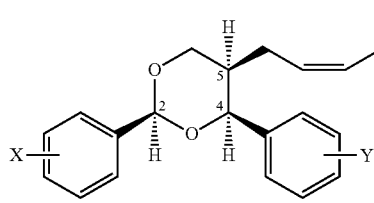

wherein X may be selected from the group consisting of fluoro, chloro, bromo, trifluoromethyl, substituted phenyl, cyano, methoxy, nitro, hydroxyl and —H, preferably X is selected from the group consisting of halogeno, more preferably X is chloro, wherein X may be in the ortho, meta and/or para position, preferably the ortho position, and wherein Y may be selected from the group consisting of fluoro, chloro, bromo, trifluoromethyl, substituted phenyl, cyano, methoxy, nitro, hydroxyl, —C(O)-saccharide (preferably a mono- or disaccharide, more preferably, a monosaccharide, even more preferably glycosyl) and —H, preferably Y is selected from the group consisting of $C_{1-6}$ alkyl-OH, —OH, —O—$C_{1-6}$-alkyl (branched or linear, preferably linear), —OC(O)—$C_{1-6}$-alkyl (branched or linear, preferably linear) and —O—CH(O), more preferably Y is selected from the group consisting of —OH, methoxy and —O—C(O)—$CH_3$, wherein Y may be in the ortho, meta and/or para position, preferably the ortho position, and Rd is —NH—$C_{1-6}$-alkyl (branched or linear, preferably linear), —O—$C_{1-6}$-alkyl (branched or linear, preferably linear), a saccharide (preferably a mono- or disaccharide, more preferably, a monosaccharide, even more preferably glycosyl) or —OH, preferably Rd is —OH or —O—$CH_3$.

In one preferred embodiment PPAR modulators, TP receptor antagonists and/or TS inhibitors of the invention are compounds of Formula XI, wherein Rd is —OH. These compounds have the general formula XII:

Formula XII

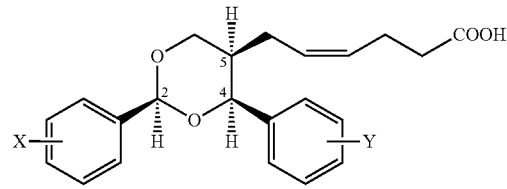

wherein X and Y is as indicated herein above for compounds of Formula XI. The specific stereochemistry of the compounds of formula XII is important and is as indicated in said formula.

Very preferred PPAR modulators, TP receptor antagonists and/or TS inhibitors according to the present invention are compounds of formula XIII:

Formula XIII

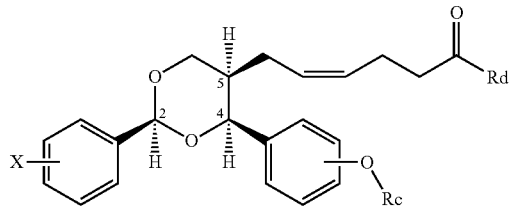

wherein X is as specified herein above for compounds of formula II, preferably X is halogeno, more preferably X is chloro, wherein X may be in the ortho, meta and/or para position, preferably the ortho position, and Rc is $C_{1-6}$-alkyl (branched or linear, preferably linear), —C(O)—$C_{1-6}$-alkyl (branched or linear, preferably linear), —CH(O), a saccharide (preferably a mono- or disaccharide, more preferably, a monosaccharide, even more preferably glycosyl) or —H, preferably Rc is methoxy, —C(O)—$CH_3$ or —H, and Rd is —NH—$C_{1-6}$-alkyl (branched or linear, preferably linear), —O—$C_{1-6}$-alkyl (branched or linear, preferably linear), glycosyl or —OH, preferably Rd is —OH, glycosyl or —O—$CH_3$, more preferably Rd is —H or —O—$CH_3$.

The specific stereochemistry of the compounds of formula XIII is important and is as indicated in said formula.

To illustrate, (Z)-6-(2-(2-chlorophenyl)-4-(2-hydroxyphenyl)-1,3-dioxan-5-yl(hex-4-enoic acid) has double bond diastereoisomers, cis and trans. Both enantiomers tested in the Examples below have the double bond in the cis configuration. Each of the 3 groups around the dioxan can be in a cis or trans position relatively to each other and gives a total of 8 possible combinations, only 2 where all 3 groups are in the cis position, i.e the substituent can be all up or all down.

(Z)-6-((2R,4R,5S)-2-(2-chlorophenyl)-4-(2-hydroxyphenyl)-1,3-dioxan-5-yl(hex-4-enoic acid has the 3 groups all down

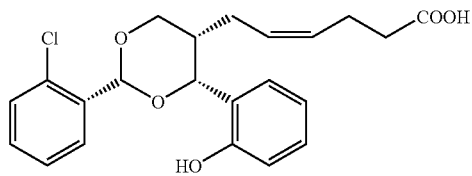

(Z)-6-((2S,4S,5R)-2-(2-chlorophenyl)-4-(2-hydroxyphenyl)-1,3-dioxan-5-yl)hex-4-enoic acid has the 3 groups all up, which has a dramatic effect on its biological activities:

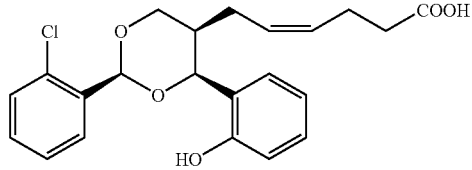 [SMILES: O=C(O)CC/C=C\C[C@@H]1CO[C@H](c2ccccc2Cl)O[C@@H]1c1ccccc1O]

In a very preferred embodiment the —O—Rc group is positioned in the ortho-position. In this embodiment preferred PPAR modulators, TP receptor antagonists and/or TS inhibitors are compounds of formula XIV:

Formula XIV

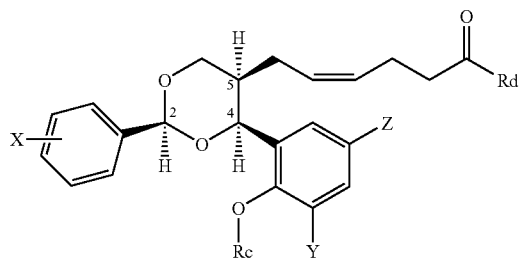

wherein X, Z and Y is as specified herein above for compounds of formula II, preferably X is halogeno, more preferably X is chloro, wherein X may be in the ortho, meta and/or para position, preferably the ortho position, and preferably Z and Y are both —H, and Rc is $C_{1-6}$-alkyl (branched or linear, preferably linear), —C(O)—$C_{1-6}$-alkyl (branched or linear, preferably linear), —CH(O), a saccharide (preferably a mono- or disaccharide, more preferably, a monosaccharide, even more preferably glycosyl) or —H, preferably Rc is methoxy, —C(O)—$CH_3$ or —H, and Rd is —NH—$C_{1-6}$-alkyl (branched or linear, preferably linear), —O—$C_{1-6}$-alkyl (branched or linear, preferably linear), a saccharide (preferably a mono- or disaccharide, more preferably, a monosaccharide, even more preferably glycosyl) or —OH, preferably Rd is —OH, glycosyl or —O—$CH_3$, more preferably Rd is —H or —O—$CH_3$.

The specific stereochemistry of the compounds of formula XIV is important and is as indicated in said formula.

Very preferred compounds of the invention may be selected from the group consisting of (Z)-6-((2S,4S,5R)-2-(2-chlorophenyl)-4-(2-hydroxyphenyl)-1,3-dioxan-5-yl)hex-4-enoic acid, (Z)-6-((2S,4S,5R)-2-(2-chlorophenyl)-4-(2-methoxyphenyl)-1,3-dioxan-5-yl)hex-4-enoic acid, (Z)-6-((2S,4S,5R)-2-(2-chlorophenyl)-4-(2-acetoxyphenyl)-1,3-dioxan-5-yl(hex-4-enenoic acid and Methyl-(Z)-6-((2S,4S,5R)-2-(2-chlorophenyl)-4-(2-hydroxyphenyl)-1,3-dioxan-5-yl)hex-4-enoate.

Accordingly, one preferred compound is a compound of the following structure:

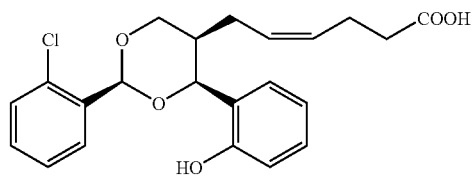 [SMILES: O=C(O)CC/C=C\C[C@@H]1CO[C@H](c2ccccc2Cl)O[C@@H]1c1ccccc1O]

Another preferred compound is a compound of the following structure:

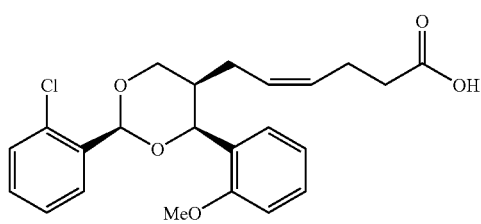 [SMILES: COc1ccccc1[C@H]1O[C@@H](c2ccccc2Cl)OC[C@H]1C/C=C\CCC(=O)O]

Another preferred compound is a compound of the following structure:

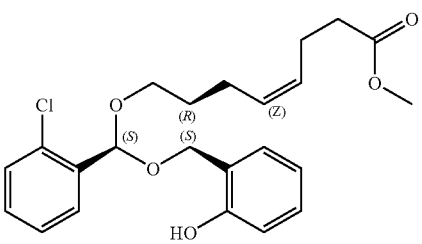

(Z)-methyl 6-((2S,4S,5R)-2-(2-chlorophenyl)-4-(2-hydroxypl-enyl)-1,3-dioxan-5-yl)hex-4-enoate Another preferred compound is a compound of the following structure:

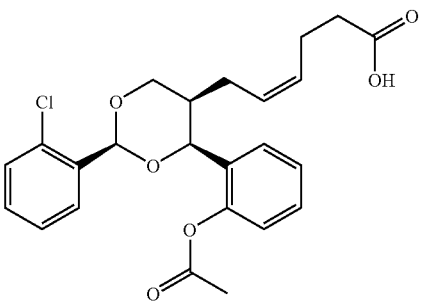

(Z)-6-((2S,4S,5R)-4-(2-acetoxyphenyl)-2-(2-chlorophenyl)-1,3-dioxan-5-yl)hex-4-enoic acid Useful PPAR modulators, TP receptor antagonists and/or TS inhibitors according to the invention can be prepared and administered as prodrugs of any of the aforementioned compounds. Those of skill in the art will appreciate that the compounds of the invention described herein may include functional groups that can be masked with progroups to create prodrugs. Such prodrugs are usually, but need not be, pharmacologically inactive until converted into their active drug form. In the prodrugs of the invention, any available functional moiety may be masked with a progroup to yield a prodrug. Myriad progroups suitable for masking such functional groups to yield promoieties that are cleavable under the desired conditions of use are known in the art.

As used herein, the term "prodrug" means a substance that is transformed in vivo to yield a substance of the present invention. The transformation may occur by various mechanisms, such as through hydrolysis in blood. For example, when a compound of the present invention contains a carboxylic acid functional group, a prodrug can comprise an ester formed by the replacement of the hydrogen atom of the acid group with a group including, but not limited to, groups such as for example ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N (alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl, carbamoyl-($C_1$-$C_2$)alkyl, N,N-di($C_1$-$C_2$)alkylcarbamoyl-($C_1$-$C_2$)alkyl and piperidino-, pyrrolidino- or morpholino ($C_2$-$C_3$)alkyl. The prodrug may also be a compound wherein an —COOH group has reacted with a saccharide to form an ester, the saccharide preferably being a mono- or disaccharide, more preferably, a monosaccharide, even more preferably glucose.

Some of the compounds of the invention that have a functional group that can be derivatized, such as the phenolic functional groups, the carboxylic functional group, the thiol functional group, and the like, can be used for the synthesis of prodrugs. Exemplary prodrugs of the compounds of the invention include:

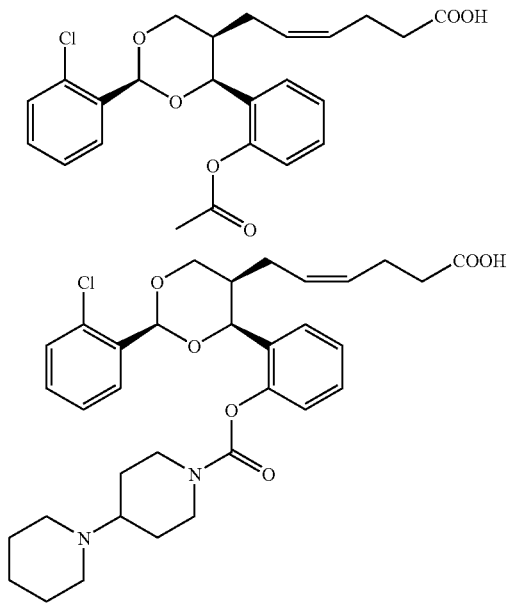

In this way, prodrugs specifically tailored for selected modes of administration can be obtained. The progroup can also be designed to impart the prodrug with other properties, such as, for example, improved passive intestinal absorption, improved transport-mediated intestinal absorption, protection against fast metabolism (slow-release prodrugs), tissue-selective delivery, passive enrichment in target tissues, targeting-specific transporters, etc. Groups capable of imparting prodrugs with these characteristics are well-known, and are described, for example, in Ettmayer et al. (2004) J. Med. Chem. 47: 2393-2404. All of the various groups described in these references can be utilized in the prodrugs described herein. In particular, the phenol group can be converted to phosphate esters, alkyl esters, or derivatized using polyethylene glycol (PEG), alkyloxycarbonyloxymethyl (AOCOM), or as a sterically hindered alkoxycarbonyloxymethyl, as illustrated below.

PHENOLIC PRODRUGS

PHOSPHATE ESTERS

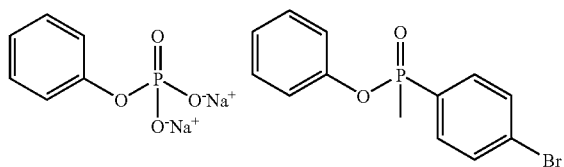

ALKYL ESTERS

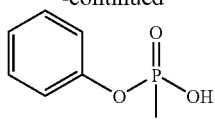

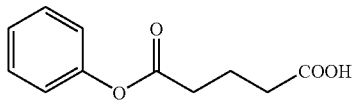

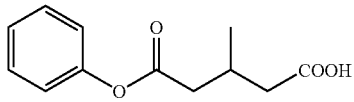

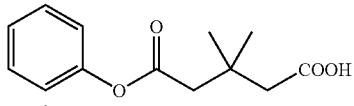

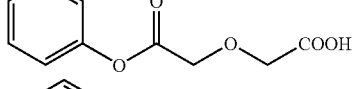

PEG DERIVATIVES

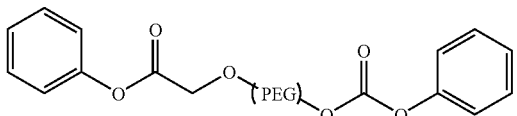

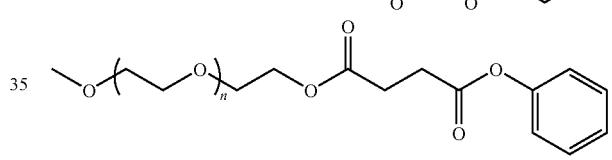

ALKYLOXYCARBONYKLOXYMETHYL (AOCOM) DERIVATIVES

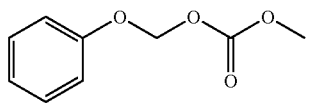

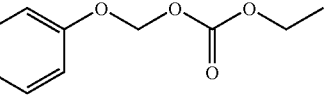

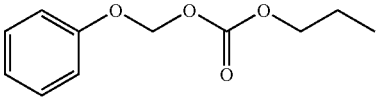

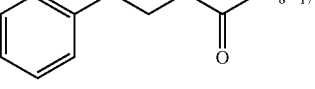

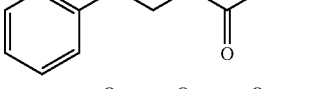

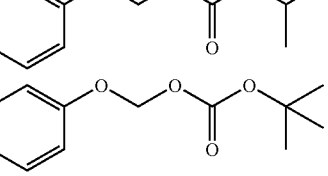

-continued
STERICALLY HINDERED ALKOXYCARBONYLOXYMETHYL DERIVATIVES

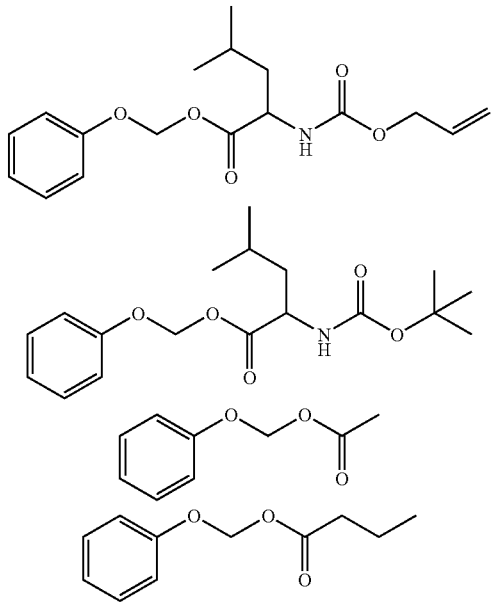

Useful PPAR modulators, TP receptor antagonists and/or TS inhibitors according to the invention also include solvates of any of the aforementioned compounds.

As used herein, the term "solvate" means any compound of the invention or a salt thereof that further includes a stoichiometric or non-stoichiometric amount of a solvent bound by non-covalent intermolecular forces. Preferred solvents are volatile, non-toxic, and/or acceptable for administration to humans in trace amounts. The solvated forms, including hydrated forms, are equivalent to unsolvated forms and are encompassed within the scope of the present invention.

As described herein above preferred PPAR modulators, TP receptor antagonists and/or TS inhibitors according to the invention have a specific stereochemistry as described above. It is preferred that any composition of the invention comprises a substantially enantiomeric pure compound. Accordingly, it is preferred that the PPAR modulators, TP receptor antagonists and/or TS inhibitors of the invention has an optical purity of at least 80%, more preferably at least 90%, even more preferably at least 95%, yet more preferably at least 98%, even more preferably at least 99%, yet more preferably at least 99.5%, yet more preferably at least 99.8%, for example at least 99.9%, such as essentially 100%, for example 100% optical purity.

The compounds of formula I, formula II, formula IX, formula X, formula XI, formula XII, formula XIII and formula XIV may be manufactured by conventional procedures of organic chemistry well known in the art for the manufacture of structurally analogous compounds. Such procedures are provided for example in EP 0 094 239 pages 4-10, which are hereby specifically incorporated by reference, and by the procedures described in the Examples section and by the following processes in which X, Y and Z have any of the meanings defined herein above:

(A) An aldehyde of the formula IV is reacted with a Wittiig reagent of the formula $R^1_3 P{=}CH(CH_2)_2 CO_2^- M^+$ wherein $R^1$ is (1-6C)alkyl or aryl (especially phenyl) and W is a cation, for example an alkali metal cation such as the lithium, sodium or potassium cation. In some embodiments the aldehyde will be reacted with a Wittig reagent of the formula be modified to $P{=}CH(CH_2)_n COO^- M^+$ where n=0 to 4.

The process in general produces the required compounds of formula II in which the substituents adjacent to the double bond have predominantly cis-relative stereochemistry i.e. the "Z" isomer. However the process also produces analogous compounds having trans-relative stereochemistry which may be removed by a conventional procedure such as chromatography or crystallisation, if desired.

The synthetic process is conveniently performed in a suitable solvent or diluent, for example an aromatic solvent such as, toluene or chlorobenzene, an ether such as 1,2-dimethoxyethane, t-butyl methyl ether, dibutyl ether or tetrahydrofuran, in dimethyl sulphoxide or tetramethylene sulphone, or in a mixture of one or more such solvents or diluents. The process is generally performed at a temperature in the range, for example, of −80° C. to 40° C., but is conveniently performed at or near room temperature, for example in the range 0 to 35° C.

(B) A phenol derivative of the formula V wherein $R^1$ is a protecting group, for example (1-6C) alkyl (such as methyl or ethyl), acyl (such as acetyl, benzoyl, methanesulphonyl or ptoluenesulphonyl), allyl, tetrahydropyran-2-yl, trimethylsilyl, and is deprotected.

The deprotection conditions used depend on the nature of the protecting group $R^1$. Thus, for example, when it is methyl or ethyl the deprotection may be carried out by heating with sodium thioalkoxide(hydride and alkanethiol) in a suitable solvent (such as N,N-dimethylformamide or N,N-dimethyl-3,4,5,6-tetrahydro-2(1H)-pyrimidinone) at a temperature in the range, for example, of 50 to 160° C. Alternatively, an ethyl or methyl protecting group may be removed by reaction with lithium diphenylphosphide in a suitable solvent (such as tetrahydrofuran or methyl t-butyl ether) at a temperature in the range, for example, of 0 to 60° C. When the protecting group is acyl it may be removed, for example, by hydrolysis in the presence of a base (such as sodium or potassium hydroxide) in a suitable aqueous solvent [such as an aqueous (1-4C) alkanol] at a temperature in the range, for example, of 0 to 60° C. When the protecting group is allyl or tetrahydropyran-2-yl, it may be removed, for example, by treatment with strong acid such as trifluoroacetic acid and when it is trimethylsilyl, it may be removed, for example, by reaction with aqueous tetrabutylammonium fluoride or sodium fluoride using a conventional procedure.

(C) An erythro-diol derivative of the formula V wherein one of $Q^1$ and $Q^2$ is hydrogen and the other is hydrogen or a group of the formula —CRaRb.OH (wherein Ra and Rb are the same or different (1-4C) alkyl) is reacted with a benzaldehyde derivative of the formula VII or an acetal, hemiacetal or hydrate thereof.

The benzaldehyde VII [or its hydrate, or its acetal or hemiacetal with a (1-4C)alkanol (such as methanol or ethanol)] may conveniently be present in an excess.

The reaction is generally performed in the presence of an acid catalyst such as hydrogen chloride, hydrogen bromide, sulphuric acid, phosphoric acid, methanesulphonic acid, camphorsulfonic acid, citric acid, pyridinium p-toluenesulfonic acid (PPTS) or p-toluenesulphonic acid, conveniently in the presence of a suitable solvent or diluent, such as toluene, xylene or an ether, for example tetrahydrofuran, dibutyl ether, methyl t-butyl ether or 1,2-dimethoxyethane or haloalkane such as dichloromethane (DCM), and at temperature in the range, for example, of 0 to 80° C.

Those starting materials of formula VI wherein $Q^1$ and $Q^2$ are both hydrogen may be obtained, for example, by mild, acid catalysed, hydrolysis or alcoholysis of the dioxane ring of a compound of formula VIII wherein Ra and Rb are both alkyl such as methyl or ethyl, obtained by an analogous procedure to process (A) herein. The hydrolysis or alcoholysis will normally be carried out at a temperature in range of 10 to 80° C. using an aqueous mineral acid such as hydrochloric acid in an alkanol (such as ethanol or 2-propanol) or an ether (such as tetrahydrofuran) as solvent.

The starting materials of formula VI wherein one of $Q^1$ and $Q^2$ is hydrogen and the other is a group of the formula —CRaRb.OH are intermediates in the above-mentioned formation of the starting materials of formula VI wherein $Q^1$ and $Q^2$ are both hydrogen. However, said intermediates are not normally isolated or characterised. Therefore, a useful modification of process (C) comprises reacting a compound of formula VIII wherein one of Ra and Rb is hydrogen, methyl or ethyl and the other is methyl or ethyl with an excess of a compound of the formula VII (or a hydrate, acetal or hemiacetal thereof) in the presence of an acid catalyst (such as one of those given above), conveniently at a temperature in the range, for example, of 10 to 80° C., and optionally in the presence of a suitable solvent or diluent (such as one of those given above).

The starting materials for use in the above processes may be made by general procedures of organic chemistry, known for the preparation of structurally related compounds. Thus, the aldehydes of formula IV may be obtained, for example, by the method shown in Scheme I. The protected phenol derivatives of formula V may be made, for example, by using an analogous procedure to process (A) above using an aldehyde analogous to that of formula IV, but wherein the phenol group has been protected with the group $R^1$, such an aldehyde being made, for example, by carrying out the procedures of Scheme I omitting the deprotection step (ii). Those of the starting materials of formula VIII which are novel may be obtained using analogous procedures to those described in European patent application, publication No. 94239.

The necessary Wittig reagents may be obtained by conventional procedures, for example by treating the corresponding phosphonium halides with a strong base such as sodium hydride, lithium diisopropylamide, potassium t-butoxide, LiHMDS or butyllithium. They are generally formed in situ just prior to carrying out the condensation process (A) above.

It will be understood that the compounds of formula I and II may also be obtained by other conventional procedures well known in the art, for example by base catalysed hydrolysis of the corresponding esters, amides or nitriles.

When a salt of a compound of formula I or II is required, it is obtained by reaction with the appropriate base affording a physiologically acceptable cation, or by any other conventional procedure.

Further, when an optically active form of a compound of formula I or II is required or when preparing a compound of any of formulas IX, X, XI, XII, XIII or XIV, which are all specific optically active forms, one of the aforesaid processes may be carried out using an optically active starting material. Alternatively, the racemic form of a compound of formula II or a racemic mixture of a compound of any of formulas IX, X, XI, XII, XIII or XIV and its enantiomer(s), may be reacted with an optically active form of a suitable organic base, followed by conventional separation of the diastereoisomeric mixture of salts thus obtained, for example by fractional crystallisation from a suitable solvent, for example a (1-4C) alkanol, whereafter the optically active form of said compound of formula I or II may be liberated by treatment with acid using a conventional procedure for example using an aqueous mineral acid such as dilute hydrochloric acid.

In addition, Example 29 illustrates how a racemic mixture of compounds of Formula I and II may be isolated by chiral chromatography. In particular, Example 29 describes how enantiomers can be isolated from a racemic mixture. This method may easily be adapted in the preparation of particular enantiomers of the other compounds of the invention.

As stated earlier, the compounds described herein are modulators of PPAR activity. Thus, in addition to the structural characteristics outlined above, preferred compounds to be used with the methods according to the present invention are also PPAR agonists, PPAR antagonist or PPAR partial agonists, preferably PPAR partial agonists. Methods for determining functionalities as PPAR agonist/antagonist/partial agonist are described herein below in the section "Functionalities of compounds"

Functionalities of Compounds

Preferred compounds of the invention are any of the compounds described herein above that are PPAR modulators, in particular PPARgamma selective modulators (full or partial agonists or antagonists, preferably agonists), TP receptor antagonists or TS inhibitors, or compounds exhibiting two or more of these properties. Although not wishing to be bound by theory, the present inventors believe compounds that are TP receptor antagonists and TS inhibitors are particularly desirable as this leads to increased PGI2 levels which inhibits platelet aggregation and acts as a potent vasodilator.

Agonists and antagonists are characterized by their binding affinities, dictating potency/$EC_{50}$/$IC_{50}$ values, and by the level of activity, which is attained in the presence of saturating levels of the compounds, i.e. efficacy. A partial agonist/partial antagonist is also characterized by its binding affinity, and efficacy. Thus, a partial agonist/partial antagonist of PPAR is unable to fully activate the cognate PPAR and can in a competitive manner displace a full agonist from the receptor and thereby diminish the level of transactivation. Full and partial agonists of PPAR furthermore may recruit different complements of cofactors, and the nature of the cofactors recruited to a given PPAR subtype may profoundly influence the pattern of genes activated by a given agonist.

The ligand-binding pockets of the PPARs are large compared with other nuclear receptors, and this may in part explain the large variety of compounds that are able to bind to and activate the PPARs. There is a considerable overlap in ligand recognition between the three PPAR subtypes, and strictly speaking, no subtype specific ligand has yet been identified. However, several natural and synthetic ligands exhibit a great degree of selectivity, and the most selective ligands today differ by more than 3 orders of magnitude with regard to the concentration needed to activate the individual PPAR subtypes. In analogy with agonists for the steroid nuclear receptors, the term selective PPAR modulators (SP-PARMs) has been introduced (herein also referred to as "Partial agonists or antagonists"). This class of ligand comprises partial agonists/antagonists that upon binding to the PPAR(s) introduce different conformations leading to recruitment of different sets of coactivators. In principle, a SPPARM would be able to activate only a subset of PPAR target genes thereby possibly promoting specific expression of a desirable set of genes. A model of PPAR activation by a full agonist and a partial agonist is given in FIG. 1. Preferred compounds according to the present invention are partial PPAR agonists.

PPAR modulating activity can be easily determined by any number of methods known in the art or adaptations thereof. For example, PPAR modulating activity may be determined by an in vitro transactivation assay. A non-limiting example of a useful transactivation assay for determining PPAR-gamma modulating activity is described in example 22 herein below and a non-limiting example of a useful transactivation assay for determining PPARdelta modulating activity is described in example 23. Example 22 below illustrates a method where compounds are added to cells transfected with a construct encoding a PPAR-GAL4 (DNA binding domain) fusion protein and a construct encoding a GAL4 dependent reporter construct. It will be apparent to one of ordinary skill in the art that any number of possible constructs can be used, such as using different DNA binding domains to activate transcription or different reporter genes (for example, fluorescent proteins, beta-galactosidase, peroxidase, luciferase, or the like). It will also be apparent to one of ordinary skill in the art that depending on which PPAR activity it is desirable to determine, the construct preferably encodes said PPAR or a ligand binding domain thereof. Upon activation of PPAR (i.e., in the presence of a PPAR agonist or partial agonist), PPAR transactivates the reporter construct, optionally in a quantitative manner.

PPAR modulators may also be identified using a reporter gene comprising a first nucleic acid operably under control of a second nucleic acid comprising at least one PPRE. The first nucleic acid preferably encodes a reporter protein, such as a fluorescent protein, beta-galactosidase, peroxidase, luciferase, or the like. Said reporter construct should be inserted into a cell expressing one or more PPARs, such as PPARgamma and/or delta. PPAR agonists can thus be identified as compounds capable of activating transcription of the first nucleic acid.

According to a specific embodiment of the invention, the preferred compounds are PPAR and/or PPAR LBD agonists or partial agonists. The term "PPAR LBD" refers to the ligand binding domain of PPAR. According to a preferred embodiment, the compounds and compositions of the present invention are PPARgamma and/or PPARgamma LBD agonists. By "agonist" is meant a compound or composition which when combined with an intracellular receptor stimulates or increases a reaction typical for the receptor, e.g., transcription activation activity. In one embodiment, said agonist is a PPARgamma agonist, i.e., a PPAR ligand which potentiates, stimulates, induces or otherwise enhances the transcriptional activity of a PPARgamma receptor, e.g., such as by mimicking a natural physiological ligand for the receptor.

Said PPAR modulating activity may be determined using the transactivation assays described herein above. Suitable standard agonists include rosiglitazone for PPARgamma and (4-[3-(2-Propyl-3-hydroxy-4-acetyl)phenoxy]propyloxyphenoxy)acetic acid (L165041, commercially available) for PPARdelta. Potential agonists that exhibit less than 50% transactivation than a standard agonist may still be useful, in particular for the development of new compounds or active derivatives or as an indicator of the presence of a partial agonist.

According to a preferred embodiment, the compounds and compositions of the present invention are PPAR and/or PPAR LBD partial agonists, and more particularly, the compounds and compositions of the present invention are PPARgamma and/or PPARgamma LBD partial agonists. A drug that produces less than the possible maximal effect (i.e. the maximal effect produced by a full agonist, or reference molecule) is called a partial agonist.

For example, the partial agonist property of the compounds and compositions of the present invention can be defined by reference to rosiglitazone (Avandia™, Glaxo-SmithKline) which is a full agonist. This is in particular the case for PPARgamma partial agonists. The partial PPAR agonists, in particular PPARgamma agonists, of the invention will provide similar or better efficacy to a patient undergoing a desired treatment but will have fewer undesirable side effects which would be detrimental to the patient. For example, SN1 (DPD) induces the same level of glucose uptake at 10 mM as Avandia at 1 mM but fewer side effects are expected as a consequence of lower adipocyte differentiation.

The partial agonist property of the compounds and compositions of the present invention may also be defined by reference to L165041 (commercially available). This is in particular the case for PPARdelta partial agonists. For example, one such transactivation assay, is the transactivation assay described in example 23.

In one embodiment it is preferred that the compounds of the invention are selective for activation of PPAR. In such an embodiment it is preferred that the compound does not significantly activate RxR and/or RxR LBD transactivation, preferably RxR transcription is less than 2 times background levels, such as less than 1.5 times background levels, for example approximately equal to or less than background level. RxR transactivation may be determined by an RxR transactivation assay, for example as described in example 25. Background level is transactivation in the absence of an added ligand.

In one embodiment of the invention, the compounds are PPAR antagonists. By "antagonist" is meant a compound, which when combined with PPAR interferes or decreases a reaction typical for said PPAR, e.g., transcription activation. As a general definition, "PPAR antagonist" designates a PPAR ligand which can inhibit the activity of a corresponding PPAR agonist. More generally, these agonist/antagonist/partial agonist activities may be measured by assays widely known to one skilled in the art, such as, for example, those which are disclosed in WO99/50664 or WO96/41013.

In a very preferred embodiment of the invention the PPAR modulator has an $IC_{50}$ in relation to PPAR binding of at the most 25 µM, preferably of at the most 20 µM, even more preferably of at the most 10 µM, for example at the most 5 µM. Within this embodiment of the invention the preferred PPAR is PPARγ and very preferred PPAR modulators are PPARγ modulators, which have an $IC_{50}$ in relation to PPARγ binding of at the most 25 µM, preferably of at the most 20 µM, even more preferably of at the most 15 µM, for example at the most 12 µM. $IC_{50}$ may be determined by any suitable method known by the skilled person.

The compounds and compositions of the invention are further characterized by their biological activities when administered to a patient having a condition or disease that is affected by modulation of PPAR activity. Preferred compounds according to the present invention are compounds capable of lowering one or more of the following biological entities in a patient in need thereof: glucose, triglycerides, fatty acids, cholesterol, bile acid, and the like, with better or equivalent efficacy and potency, but with lower toxicity and/or occurrence of fewer undesirable side effects compared to known molecules in the art (e.g., thiazolidinediones). In particular, said compounds preferably lead to less induction of adipocyte differentiation and weight gain. Such compounds may in particular be any of the compounds described in section C herein above. Useful methods for determining adipocyte differentiation are described in example 26 herein below. More specifically, they present beneficial activities towards insulin resistance (diminished effectiveness of insulin to lower plasma glucose levels) and/or adipogenesis. It has been shown that many compounds that activate PPARgamma (e.g. thiazolidinediones) further induce adipocyte differentiation (i.e., exhibit an adipogenic, or lipogenic, effect) and thus result in body weight increase in treated patients. Therefore, it is highly desirable that the next generation of such compounds show reduced activity and preferably are devoid of such activity. These activities can be appreciated using methods widely used in the art. More specifically, these activities are appreciated with reference to a molecule which has already been identified in the art, such as rosiglitazone. According to a preferred embodiment of the invention, preferred compounds display at least about 50%, preferably at least about 60%, more preferably at least about 70%, and even more preferably at least 80%, of the rosiglitazone property regarding insulin resistance, which, for example, may be determined by determining glucose levels in patients suffering from insulin resistance. Ideally, it will be 100% or more. According to another preferred embodiment of the present invention, preferred compounds display less than about 80%, preferably less than about 50%, more preferably less than about 40%, and even more preferably less than about 30%, of the rosiglitazone property towards adipocyte differentiation. Ideally this will be less than 20% of the rosiglitazone property towards adipocyte differentiation. Adipocyte differentation may, for example, be determined as described herein below in example 26. In a very preferred embodiment, the preferred compounds have both above-mentioned properties. Alternatively, the compounds are capable of inducing PPAR activity as determined in a transactivation assay to an extent which is at least 50% that of rosiglitazone and display the above-mentioned property towards adipocyte differentiation.

In a very preferred embodiment of the present invention the PPAR modulator is capable of lowering one or more, such as 2 3, or 4 properties selected from the group consisting of the following biological entities in an individual: serum glucose, glycosylated haemoglobin (HbA1C), fructosamine, insulin, free fatty acids (FFA), triglycerides (TG), low high density lipoprotein (HDL) and total cholesterol. Even more preferably the PPAR modulator is capable of lowering one or more, preferably at least 2, more preferably all 3 of the following biological entities in an individual: serum glucose, glycosylated haemoglobin (HbA1C) and free fatty acids (FFA).

In particular, preferred PPAR modulators are those wherein administration of the PPAR modulator to an individual in a dosage in the range of 0.1 to 100 mg/kg/day such as in the range of 0.5 to 70 mg/kg/day, for example in the range of 0.5 to 7.5 mg/kg/day, such as 5 mg/kg/day results in a decrease in serum glucose of at least 10%, such as at least 15%, for example at least 20%, such as at least 24% after within the range of 7 to 365 days, such as in the range of 7 to 180 days, for example in the range of 7 to 90 days, such as in the range of 7 to 30 days, for example within 14 days of administration.

In addition, preferred PPAR modulators are those wherein administration of said PPAR modulator to an individual in a dosage in the range of 0.1 to 100 mg/kg/day, such as in the range of 0.5 to 70 mg/kg/day, for example in the range of 0.5 to 7.5 mg/kg/day, such as 5 mg/kg/day results in a decrease in HbA1C of at least 0.2%, such as at least 0.5%, for example at least 1%, such as at least 2% after within the range of 7 to 365 days, such as in the range of 7 to 180 days, for example in the range of 7 to 90 days, such as in the range of 7 to 30 days, for example within 14 days of administration. The reference range in healthy patients for $Hb_{A1c}$ values is about 4%-5.9% and values below 6.5%-7% are desirable upon administration of the PPAR modulator to patients in need of treatment.

In addition, preferred PPAR modulators are PPAR modulators wherein administration of said PPAR modulator to an individual in a dosage in the range of 0.1 to 100 mg/kg/day, such as in the range of 0.5 to 70 mg/kg/day, for example in the range of 0.5 to 7.5 mg/kg/day, such as 5 mg/kg/day results in a decrease in FFA of at least 10%, such as at least 15%, for example at least 20%, such as at least 22% after within the range of 7 to 365 days, such as in the range of 7 to 180 days, for example in the range of 7 to 90 days, such as in the range of 7 to 30 days, for example within 14 days of administration. The reference range in healthy patients for FFA values is about 0.28-0.89 mmol/Liter and a lowering/normalisation of values towards this range is desirable upon administration of the PPAR modulator to patients in need of treatment.

In addition, preferred PPAR modulators are PPAR modulators wherein administration of said PPAR modulator to an individual in a dosage in the range of 0.1 to 100 mg/kg, such as in the range of 0.5 to 70 mg/kg, for example in the range of 0.5 to 7.5 mg/kg, such as 5 mg/kg does not cause a significant increase in body weight within the range of 7 to 365 days, such as in the range of 7 to 180 days, for example in the range of 7 to 90 days, such as in the range of 7 to 30 days, for example within 14 days in said individual. By "significant increase in body weight" is meant a change in body weight which is more than 1%, such as more than 2%, for example more than 3%, such as more than 4%, for example more than 5%, such as more than 6%, such as more than 7% increase in body weight.

In addition, preferred PPAR modulators are PPAR modulators wherein administration of said PPAR modulator in a dosage in the range of 0.1 to 100 mg/kg, such as in the range of 0.5 to 70 mg/kg, for example in the range of 0.5 to 7.5 mg/kg, such as 5 mg/kg does not result in a significant change in food intake per day in said individual. By "significant change in average food intake" is meant a change which is more than 10%, such as more than 12%, for example more than 14%, such as more than 16% in the daily food intake as determined by weight.

In addition, preferred PPAR modulators are PPAR modulators wherein administration of said PPAR modulator to an individual in a dosage in the range of 0.1 to 100 mg/kg, such as in the range of 0.5 to 70 mg/kg, for example in the range of 0.5 to 7.5 mg/kg, such as 5 mg/kg does not result in a significant increase in one or more, preferably at least 2, such as at least 3, for example all 4 of the following biological entities: Hematocrit, aspartate aminotransferase (AST), alanine aminotransferase (ALT) and alkaline phosphatases (ALP) in said individual. By "significant increase" is meant an increase of more than 30%, for example of more than 20%, such as of more than 10%, for example of more than 5%. The reference range in healthy patients for hematocrit is 0.41-0.50 (unitless), for AST is 10-30 U/L, 10-40 U/L, and 30-120 U/L for ALP and a lowering/normalisation of these values towards these ranges is desirable upon administration of the PPAR modulator to patients in need of treatment.

All aforementioned individuals in this section may be any individual, such as an individual in need of administration of a PPAR modulator, for example a human being suffering from one or more of the PPAR related clinical conditions mentioned herein elsewhere. However, the individual may also be a laboratory test animal, for example a mouse. All aforementioned decreases and increases in this section are in general determined in relation to the values obtained in similar individuals to which said PPAR modulator has not been administered. A non-limiting example of suitable methods for determining aforementioned decreases and increases in biological entities are described herein below in Example 32.

The in vivo occurrence of undesirable side effects such as haemodilution, oedema, adipocyte differentiation, or obesity may be influenced by the cofactor recruitment profile of said compounds, for example using methods described in EP1267171. Thus, in one embodiment of the invention, preferred compounds are compounds which are predicted to have low in vivo occurrence of undesirable side effects.

It is widely acknowledged that nuclear receptors, such as PPARgamma, achieve transcriptional activation or repression by binding to cognate sequences in the promoter regions of target genes and by recruiting numerous cofactor complexes whose activities range from chromatin remodeling, histone and cofactor modification, to basic transcription machinery recruitment (Glass, & Rosenfeld, 2000, Genes Dev., 14, 121-141). These cofactors may to a large extent determine the specificity of the action of nuclear receptors and integrate their action in a network of stimuli whose proper orchestration leads to a specific cellular response. Hence, the determination of the multiple partnerships in which each nuclear receptor is engaged, as a function of time and cell type, will lead to a better understanding of the activity of nuclear receptors in transcriptional regulation. For instance, it is known that for certain hormones, such as estrogen, the response to the hormone is determined almost to the same extent by the presence of the respective nuclear hormone receptor, as by the presence of the cofactors, which interact with the receptor. Various PPAR cofactors have been identified. Some cofactors such as p300/CBP (Dowell et al., 1997, J. Biol. Chem. 272, 33435-33433), SRC-1 (Onate et al., 1995, Science 270, 1354-1357), TIF2 (GRIP-2; Chakravarti et al., 1996, Nature, 383, 99-103), SRA (Lanz et al., 1999, Cell, 97, 17-27), AIB-1 (Anzick et al., 1997, Science, 277, 965-968), TRAP220/DRIP205 (i.e. PBP; Zhu et al., 1997, J. Biol. Chem. 272, 25500-25506; Rachez et al., 1999, Nature, 398, 824-828), PGC-1 (Puigserver et al., 1998, Cell 92, 829-839), PRIP (Zhu et al., 2000, J Biol Chem 275, 13510-13516), PGC-2 (Castillo et al., 1999, Embo J, 18, 3676-3687), ARA70 (Heinlein et al., 1999, J Biol Chem 274, 16147-16152), RIP140 (Treuter et al., 1998, Mol Endocrinol 12, 864-881), enhance their transcriptional activity, whereas SMRT (Lavinsky et al., 1998, Proc. Natl. Acad. Sci. USA 95, 2920-2925) and N-CoR (Dowell et al., J Biol Chem 274, 15901-15907) repress it. Additionally, it has been shown that members of the PPARgamma cofactor family (e.g. the 160-kDa protein (SRC-1/TIF2/AIB-1), CBP/p300 or TRAP220/DRIP205) interact directly with PPARgamma and potentiate nuclear receptor transactivation function in a ligand-dependent fashion leading to biological action or side effects that can differ according to the ligand used (Adams et al., 1997, J. Clin. Invest., 100, 3149-3153). Kodera et al, (2000, J Biol. Chem., 275, 33201-33204) have examined whether interactions between PPARgamma and known cofactors were induced to the same extent by different classes of PPARgamma ligands (natural and synthetic) and concluded that the overall structure of PPARgamma and cofactors complexes may be different according to the ligands involved, resulting in the activation of a particular set of target gene promoters that exert different biological actions.

PPAR partial agonists will in general have a particular coactivator recruitment profile, thus compounds with particular coactivator recruitment profiles are preferred. Thus, according to special embodiments, the compounds and compositions of the present invention are furthermore characterized by a restricted cofactor(s) recruitment pattern. In preferred embodiments, said pattern results in distinct effects on the regulation of the transcriptional activity of said nuclear receptors allowing a very finely tuned regulation which results in the activation of specific metabolic processes as well as the elimination of unwanted side effects. In more specific embodiments, the compounds and compositions of the present invention are furthermore able to inhibit the interaction of PPAR receptor, more preferably PPAR receptor LBD with cofactor TIF2. According to another embodiment, the compounds and compositions of the invention are additionally able to enhance the interaction of PPAR receptor, more preferably PPAR receptor LBD, with cofactor SRC-1. Preferably, said PPAR receptor is PPARgamma receptor.

Methods for measuring inhibition and/or enhancement of cofactor recruitment by ligands are detailed in EP1267171.

In a preferred embodiment, the compounds of the invention when bound to PPARgamma will allow recruitment of SRC1 to the LBD with an $EC_{50}$ which is at least one log greater than the one for TIF2, with at least 2 log being preferred.

In one embodiment of the invention, preferred compounds due to their agonistic, particularly partial agonistic, or antagonistic property towards natural physiological ligands of the PPAR receptors, especially those of the PPARgamma receptor, are capable of serving as pharmaceuticals for controlling the biological effects of PPAR mediated transcriptional control and the attendant physiological effects produced thereby. More specifically, they can modulate a cellular physiology to reduce an associated pathology or provide or enhance prophylaxis.

In yet another embodiment of the invention, preferred compounds are compounds which are agonists (or preferably partial agonists) of more than one PPAR, for example of both PPARgamma and PPARdelta. Such agonists may be identified by transactivation assays for PPARgamma and PPARdelta, respectively, for example as described herein. Non-limiting methods for determining PPARgamma and PPARdelta activity are described herein below in examples 27 and 28, respectively.

In one embodiment of the invention the preferred compounds of the invention are capable of binding the thromboxane receptor (TP), such as capable of binding Thromboxane receptor in human recombinant HEK-293 cells. In particular, the compounds of the invention are capable of binding the thromboxane receptor with an $IC_{50}$ of less than 100 nM, more preferably less than 50 nM, even more preferably less than 30 nM, for example less than 20 nM, such as less than 10 nM, for example less than 5 nM, for example less than 1 nM are preferred. In addition, compounds of the invention capable of binding the thromboxane receptor with a Ki of less than 100 nM, more preferably less than 50 nM, even more preferably less than 20 nM, such as less than 10 nM, for example less than 5 nM, for example less than 1 nM are preferred. Preferably aforementioned $IC_{50}$ and Ki are determined as described herein below in Example 35.

Preferred TP receptor modulators are TP receptor antagonists. The physiological function of TP receptors include the control of platelet aggregatrion, vasoconstriction and bronchoconstriction (see The IUPHAR compendium of receptor characterization and classification 1998, page 239, and The Sigma-RBI Handbook 5th edition, Prostanoid receptors, 2006, pages 138-140). Thus, the preferred PPAR/TP modulators according to the invention, which are antagonists of TP receptors are useful in treatment of a clinical condition characterised by one or more of increased platelet aggregation, increased vasoconstriction and increased bronchoconstriction, myocardial infarction, thrombosis, thrombotic disorders, pulmonary hypertension, atherosclerosis, IgA nephropathies, hepatorenal syndrome, diabetic nephropathy, retinopathy, diabetic retinopathy, peripheral arterial disease, lower limb circulation, pulmonary embolism, thrombus formation, hyperplasia, septic shock, preeclampsia, asthma, allergic rhinitis, tumour angiogenesis and metastasis, stent-triggered thrombus formation, stent induced restenosis and stent-triggered hyperplasia.

In a further embodiment, the compounds of the invention are inhibitors (ie reduce) of Thromboxane Synthase (TS) activity. Thromboxane is involved in control of platelet aggregation, vasoconstriction and bronchoconstriction and thus inhibition of Thromboxane Synthase may also be useful in treatment of a clinical condition characterised by one or more of increased platelet aggregation, increased vasoconstriction and increased bronchoconstriction. Thromboxane Synthase activity may be determined by any useful method known to the skilled person. One useful method is described herein below in Example 34. Very preferred compounds of the invention are capable of inhibiting Thromboxane synthase by at least 30%, preferably at least 40%, such as at least 50% at a concentration of 10 µM using the human platelet thromboxane synthase assay described herein below in Example 34. Also, very preferred compounds of the invention are capable of inhibiting Thromboxane synthase with an $IC_{50}$ of at the most 10,000 nM, preferably at the most 9000 nM, yet more preferably at the most 8000 nM, yet more preferably at the most 7500 nM, for example at the most 7100 nM using the human platelet thromboxane synthase assay as described herein below in Example 34.

Preferred compounds of the invention are capable of inhibiting platelet aggregation. In particular, compounds capable of inhibiting platelet aggregation (that is, in conditions of increased platelet aggregation the compound would normalize platelet aggregation) by at least 20%, preferably at least 40%, more preferably at least 50%, yet more preferably at least 80%, for example at least 90%, such as at least 94%, for example at least 95%, such as at least 97%, for example approximately 100%, such as 100% at a concentration of in the range of 0.01 to 100 µM, preferably in the range of 1 to 30 µM, for example approximately 1 µM, such as approximately 8 µM, for example approximately 16 µM, such as approximately 30 µM, for example about 1 µM or about 8 µM are preferred. Preferably platelet aggregation is determined as described in Example 34.

Preferred compounds of the invention are capable of increasing occlusion time, i.e. the time after which an artery is occluded (0% blood flow) after induction of thrombosis, which may for example be in contact with a thrombosis promoting agent, e.g. $FeCl_3$. Thus, upon administration of a compound of the invention, the occlusion time before an artery is occluded is increased compared to the occlusion time if no compound has been administrated. Even more preferably, the compound according to the present invention is capable of increasing occlusion time in the murine thrombosis model described in Example 33 herein below. Preferred compounds of the invention are capable of increasing occlusion time to an average of at least 7, preferably at least 8, more preferably at least 9, even more preferably at least 10 min. after administration of 100 mg/kg.

In particularly preferred embodiments, the preferred compounds of the invention exhibit more than one of the properties described herein above.

Clinical Conditions

The present invention relates to methods of treatment of clinical conditions comprising administration of above-mentioned compounds (preferably any of the PPAR/TP receptor, TS modulators mentioned above, preferably any of the compounds of formula IX, X, XI, XII, XIII or XIV, such as (Z)-6-((2S,4S,5R)-2-(2-chlorophenyl)-4-(2-hydroxyphenyl)-1,3-dioxan-5-yl)hex-4-enoic acid), as well as uses of said compounds, and the salts and solvates of the compounds for preparation of a medicament for treatment of a clinical condition.

The PPAR modulators described herein above, such as (Z)-6-((2S,4S,5R)-2-(2-chlorophenyl)-4-(2-hydroxyphenyl)-1,3-dioxan-5-yl(hex-4-enoic acid) may be employed in weight control. Thus, the clinical condition may in one embodiment be an eating disorder such as anorexia nervosa (also abbreviated "anorexia" herein) or bulimia. The compounds disclosed herein above (preferably any of the PPAR modulators described above, such as (Z)-6-((2S,4S,5R)-2-(2-chlorophenyl)-4-(2-hydroxyphenyl)-1,3-dioxan-5-yl(hex-4-enoic acid) may also be employed in methods for increasing or decreasing body weight, in particular for decreasing body weight. The clinical condition may thus be obesity. Adiposity is an excessive build-up of fatty tissue. Recent investigations have shown that PPAR in particular PPARgamma plays a central role in gene expression and differentiation of adipocytes. PPARgamma subtypes are involved in the activation of adipocyte differentiation, but play a less important role in the stimulation of peroxisome proliferation in the liver. Activation of PPARgamma typically contributes to adipocyte differentiation by activating the adipocyte-specific gene expression (Lehmann, Moore, Smith-Oliver, Wilkison, Willson, Kliewer, J. Biol. Chem., 270:12953-12956, 1995). Thus, a PPAR agonist can be used to gain fatty tissue. PPAR partial agonists may be selected for properties useful in treating excessive build-up of fatty tissue.

In one preferred embodiment, the invention relates to methods for treating insulin resistance by administering any of the compounds described herein above (preferably any of the PPAR modulators described above, such as (Z)-6-((2S, 4S,5R)-2-(2-chlorophenyl)-4-(2-hydroxyphenyl)-1,3-dioxan-5-yl)hex-4-enoic acid) to an individual in need thereof. The invention also relates to use of any of said compounds (preferably any of the PPAR modulators described above, such as (Z)-6-((2S,4S,5R)-2-(2-chlorophenyl)-4-(2-hydroxyphenyl)-1,3-dioxan-5-yl)hex-4-enoic acid) for preparation of a medicament for the treatment of insulin resistance. In addition, the invention relates to methods for increasing insulin sensitivity by administration of said compounds (preferably any of the PPAR modulators described above, such as (Z)-6-((2S,4S,5R)-2-(2-chlorophenyl)-4-(2-hydroxyphenyl)-1,3-dioxan-5-yl)hex-4-enoic acid), as well as to use of said compounds for the preparation of a medicament for increasing insulin sensitivity. Acute and transient disorders in insulin sensitivity, such as those that may occur following trauma, surgery, or myocardial infarction, may be treated as taught herein.

Insulin resistance is involved in a number of clinical conditions. Insulin resistance is manifested by the diminished ability of insulin to exert its biological action across a broad range of concentrations. During early stages of insulin resistance, the body secretes abnormally high amounts of insulin to compensate for this defect. Even though blood insulin levels are chronically high, the impaired metabolic response of active muscle cells to insulin makes them unable to take up glucose effectively. It is now increasingly being recognized that insulin resistance and resulting hyperinsulinemia may contribute to several clinical conditions, for example to the metabolic syndrome (also designated syndrome X). The metabolic syndrome is characterized by a first insulin-resistant stage which causes hyperinsulinemia, dyslipidemia and reduced glucose tolerance. Patients with the metabolic syndrome have been shown to be at an increased risk of developing cardiovascular disease and/or type II diabetes.

A patient is said to suffer from the metabolic syndrome when at least three of the following criteria applies:

Central/abdominal obesity as measured by waist circumference (greater than 102 cm in men and greater than 94 cm in women)

Fasting triglycerides greater than or equal to 150 mg/dL (1.69 mmol/L)

HDL cholesterol [Men—Less than 40 mg/dL (1.04 mmol/L); Women—Less than 50 mg/dL (1.29 mmol/L)]

Blood pressure greater than or equal to 130/85 mm Hg

Fasting glucose greater than or equal to 110 mg/dL (6.1 mmol/L)

Insulin resistance also has a negative effect on lipid production, contributing to increasing VLDL (very low-density lipoprotein), LDL (low-density lipoprotein), and triglyceride levels in the bloodstream and decreasing HDL (high-density lipoprotein). This can lead to fatty plaque deposits in the arteries which, over time, can lead to atherosclerosis. Thus, the clinical condition according to the present invention may be hyperlipidemia, such as familial hyperlipidemia. Preferably, hyperlipidemia is characterised by hypercholesterolemia and/or hypertriglyceridemia. The clinical condition may also include dyslipidemia and diabetic dyslipidemia. The compounds included herein (preferably any of the PPAR modulators described above, such as (Z)-6-((2S,4S,5R)-2-(2-chlorophenyl)-4-(2-hydroxyphenyl)-1,3-dioxan-5-yl)hex-4-enoic acid) may also be utilized to lower serum triglyceride levels or raise the plasma level of HDL.

Insulin resistance may lead to excessive insulin and glucose levels in the blood. Excess insulin may increase sodium retention by the kidneys, thus the methods of the invention may be employed for decreasing sodium retention by the kidneys. Elevated glucose levels may damage blood vessels and kidneys. Thus, the methods of the invention may be employed to prevent damage to blood vessels and kidneys.

In another embodiment of the invention, the clinical condition is an inflammatory disorder mediated by PPARgamma. By the term "mediated by PPARgamma," it should be understood that PPARgamma plays a role in the manifestation of the condition. For example, PPARgamma is considered not to play a role in inflammation associated with neutrophil activation, such as acute inflammations. Although not wishing to be bound by theory, agonists of PPARgamma may be effective anti-inflammatory drugs by directly associating with and inhibiting NFκB-mediated transcription and thus modulating various inflammatory reactions, such as, for example, the enzyme paths of inducible nitrous oxide synthase (NOS) and cyclooxygenase-2 (COX-2) (Pineda-Torra, I. et al., 1999, Curr. Opinion in Lipidology, 10, 151-9).

The inflammatory disorder may be acute or chronic, such as ocular inflammation (J Biol. Chem. 2000 Jan. 28; 275(4): 2837-44) or dry eye disease (J Ocul Pharmacol Ther. 2003 December; 19(6):579-87), for example. Illustrative examples of chronic inflammatory disorder include inflammatory bowel disease, ulcerative colitis, or Crohn's disease. The chronic inflammatory disorder may also be arthritis, notably rheumatoid arthritis and polyarthritis. The chronic inflammatory disorder could also be an inflammatory skin disease, notably acne vulgaris, atopic dermatitis, cutaneous disorders with barrier dysfunction, cutaneous effects of aging or psoriasis, in particular psoriasis. The chronic inflammatory disorder may also be an inflammatory neurodegenerative disease, such as multiple sclerosis or Alzheimer's disease. The clinical condition may also be gastrointestinal diseases and renal diseases, including glomerulonephritis, glomerulosclerosis, nephritic syndrome, and hypertensive nephrosclerosis.

In another embodiment of the invention the clinical condition is a cancer responsive to activation of PPARgamma. Thus, the clinical condition may for example be a disorder characterized by aberrant cell growth of PPAR-responsive cells such as hyperplastic or neoplastic disorders arising in adipose tissue, such as adipose cell tumors, e.g., lipomas, fibrolipomas, lipoblastomas, lipomatosis, hibernomas, hemangiomas, and/or liposarcomas. Furthermore, certain cancers of prostate, stomach, lung and pancreas have been demonstrated to be responsive to treatment with PPARgamma agonists. In particular, certain liposarcomas, prostate cancers, multiple myelomas, and pancreatic cancers have been shown to be responsive to activation of PPARgamma, whereas at least some colorectal and breast cancers are not responsive (Rumi et al., 2004, Curr. Med. Chem. Anti-Canc Agents, 4:465-77). Other studies have demonstrated that other breast and colon cancers are responsive to PPAR agonists, as well as neuroblastoma and bladder cancers. The use of PPAR ligands for treatment of cancers was reviewed by Levy Kopelovich, 2002, Molecular Cancer Therapeutics, 357.

However, even though certain types of cancer may be responsive to activation with PPARgamma, all cancers of a given type may not be responsive. In particular, loss-of-function mutations of PPARgamma frequently occur in cancer and such cancers will in general not be responsive. Thus it is preferred that the cancer expresses functional PPARgamma.

The clinical condition may also be an infection, such as a viral infection, notably AIDS or infection by HIV or infection by the hepatitis C virus. In addition, the PPAR ligands of the invention may be useful for improving cognitive functions in neurologic diseases or in dementia or for treating polycystic ovarian syndrome or for preventing and treating bone loss, e.g., osteoporosis.

The clinical condition may also be a liver disease, notably infection by the hepatitis C virus, or fatty liver, liver inflammation, liver lesions, liver cirrhosis, non-alcoholic steatohepatitis, or post-hepatic cancer, whether or not associated with a hepatitis C virus infection, but preferably responsive to PPAR modulation.

The clinical condition may also be Marfan syndrome.

Although much of the description has related to PPARgamma, the compounds and methods of the invention are not limited to the modulation of PPARgamma. Indeed, it will be apparent to the artisan that other PPAR subtypes play an important role in disease. In addition it is apparent to the skilled artisan that also the thromboxane receptor plays an important role in PPAR associated diseases. For example, PPARdelta has been associated with lipid metabolism disorders and wound healing, in particular epidermal wound healing (Soon Tan et al., 2004, Expert Opinion in Molecular Targets, 39). Thus, the clinical condition may also be wound healing, including epidermal wound healing.

Insulin sensitizers, e.g., glitazones, have been used to treat insulin resistance, but while enhancing insulin sensitivity, they also increase rather than decrease body weight. Obesity and physical inactivity aggravate insulin resistance. Glitazones, (thiazolidinediones or TZDs) act by improving insulin sensitivity in adipose tissue, liver, and muscle. Treatments with said agents have been tested in several animal models of diabetes and resulted in complete correaction of the elevated plasma levels of glucose, triglycerides, and nonesterified free fatty acids without any occurrence of hypoglycemic reactions (Cheng Lai and Levine, 2000, Heart Dis., 2, 326-333). Examples of these thiazolidinediones are rosiglitazone, pioglitazone and troglitazone. However, while offering attractive therapeutic effects, these compounds suffer from numerous serious undesirable side effects including hemodilution (including oedema), liver toxicity, body weight increase (including body fat increase from increased adipocyte differentiation, plasma volume increase, and cardiac hypertrophy), modest but significant LDL-cholesterol increase and anemia (for a review, see Lebovitz, 2002, Diabetes Metab. Res. Rev, 18, Suppl 2, S23-9). Indeed a number of available treatments for diabetes are associated with weight gain, a problem of high significance for the long-term management of the disease. Hence, there is much need for alternative, more effective therapeutic agents that can be used in the management of obesity, diabetes and the commonly associated disorders such as cardiovascular and hepatic disease.

Thus, in one embodiment, the invention relates to simultaneous treatment and/or prevention of obesity and diabetes by administering the compounds of the invention (preferably any of the PPAR modulators described above, such as (Z)-6-((2S,4S,5R)-2-(2-chlorophenyl)-4-(2-hydroxyphenyl)-1,3-dioxan-5-yl)hex-4-enoic acid) to an individual:
  i. suffering from obesity and diabetes, or
  ii. at risk of acquiring diabetes, and of getting obese, or
  iii. suffering from obesity and at risk of acquiring diabetes, or
  iv. suffering from diabetes and at risk of getting obese.

The invention also relates to use of the compounds of the invention (preferably any of the PPAR modulators described above, such as (Z)-6-((2S,4S,5R)-2-(2-chlorophenyl)-4-(2-hydroxyphenyl)-1,3-dioxan-5-yl)hex-4-enoic acid), and the salts and solvates of the compounds for preparation of a medicament for the simultaneous treatment and/or prevention of obesity and diabetes. The compounds may be any of the compounds described hereinabove, preferably any of the PPAR modulators described above, more preferably any of the compounds of formulas IX, X, XI, XII, XIII or XIV, such as (Z)-6-((2S,4S,5R)-2-(2-chlorophenyl)-4-(2-hydroxyphenyl)-1,3-dioxan-5-yl(hex-4-enoic acid. Within this embodiment, diabetes is preferably diabetes type II. Said individual at risk of acquiring diabetes may, for example, be an individual suffering from the metabolic syndrome described herein above. Said individual at risk of getting obese, may, for example, be an individual under medical treatment with an anti-diabetic compound having the side-effect of weight gain.

The invention also relates to use of any of the compounds described above, more preferably any of the compounds of formula IX, such as formula X, for example formula XI, such as formula XII, for example formula XIII, such as formula XIV, such as (Z)-6-((2S,4S,5R)-2-(2-chlorophenyl)-4-(2-hydroxyphenyl)-1,3-dioxan-5-yl(hex-4-enoic acid, and the salts and solvates of the compounds for the preparation of a medicament for treatment or prevention, preferably treatment of a clinical condition associated with thromboxane in an individual in need thereof. The clinical condition may be a clinical condition characterized by increased platelet aggregation, vasoconstriction and/or bronchioconstriction. The clinical condition may, for example, be selected from the group consisting of myocardial infarction, thrombosis, thrombotic disorders, stent triggered thrombus formation, stent induced restenosis, stent-triggered hyperplasia, pulmonary hypertension, atherosclerosis, familial hypercholesterolemia, Kawasaki disease, ventricular septal defects, IgA nephropathies, hepatorenal syndrome, hepatic fibrosis, diabetic nephropathy, retinopathy, diabetic retinopathy, peripheral arterial disease, lower limb circulation, pulmonary embolism, thrombus formation, hyperplasia, septic shock, preeclampsia, asthma, rhinitis, allergic rhinitis, tumour angiogenesis and metastasis. The clinical condition related to thromboxane (TP) may also be selected from the group consisting of myocardial infarction, angina, unstable angina, stroke, transient cerebral vascular ischemia, migraine, atheroschlerosis, microangiopathy, hypertension, blood clotting defects, warfarin sparing situations (e.g., prior to surgery), pulmonary embolism, bronchial asthma, bronchitis, chronic bronchitis, pneumonia, dyspnoea and emphysema. In one preferred embodiment the clinical condition is selected from the group consisting of thrombosis, pulmonary hypertension, diabetic nephropathy, retardation of renal damage (in particular in diabetic patients), retinopathy, peripheral arterial disease, lower limb circulation, thrombus formation, stent triggered thrombus formation, stent induced restenosis, stent-triggered hyperplasia, hyperplasia, septic shock, preeclampsia, rhinitis, allergic rhinitis, tumour angiogenesis and metastasis, preferably from the group consisting of thrombosis, pulmonary hypertension, diabetic nephropathy, retinopathy, peripheral arterial disease, lower limb circulation, thrombus formation and hyperplasia. Individuals resistant to aspirin, clopidrogel, warfarin and other similar medicaments acting by different mechanisms are particularly benefited by treatment with the compounds described herein. Furthermore, the individual may be any individual suffering from or at risk of contracting any of the aforementioned clinical conditions associated with TP, preferably the individual is a human being suffering from or at risk of contracting any of the aforementioned clinical conditions associated with TP, even more preferably said individual is a human being suffering from diabetes in addition to suffering from or being at risk of contracting any of the aforementioned clinical conditions associated with TP.

In one embodiment the invention relates to treatment of thrombosis in an individual, who has already thrombosis, suffered one or more thrombotic events, or is suffering from one or more thrombotic events, said method comprising administration of any of the compounds described above, more preferably any of the compounds of formulas IX, X, XI, XII, XIII or XIV, such as (Z)-6-((2S,4S,5R)-2-(2-chlorophenyl)-4-(2-hydroxyphenyl)-1,3-dioxan-5-yl(hex-4-enoic acid to said individual.

The invention also relates to use of any of the specific compounds described above (preferably any of the compounds described above, more preferably any of the compounds of formulas IX, X, XI, XII, XIII or XIV, such as (Z)-6-((2S,4S,5R)-2-(2-chlorophenyl)-4-(2-hydroxyphenyl)-1,3-dioxan-5-yl)hex-4-enoic acid) for the preparation of a medicament for treatment or prevention of a clinical condition. The clinical condition may be selected from the group consisting of the metabolic syndrome, dyslipidemia, obesity, diabetes mellitus, insulin resistance or any of the conditions related to insulin resistance described above, hypertension, cardiovascular disease, coronary artery restenosis, autoimmune diseases (such as asthmas, multiple sclerosis, psoriasis, topical dermatitis, and ulcerative colitis), cancer, inflammation, wound healing, lipid metabolism disorders, liver disease (such as infection by the hepatitis C virus, or fatty liver, liver inflammation, liver lesions, liver cirrhosis or post-hepatic cancer whether or not associated with a hepatitis C virus infection), gastrointestinal or renal disease (such as glomerulonephritis, glomerulosclerosis, nephritic syndrome, or hypertensive nephrosclerosis), infection (in particular viral infection), cognitive function disorders (such as neurologic disorders or dementia), polycystic ovarian syndrome, bone loss (such as osteoporosis) and AIDS.

Cancer may be any cancer, for example any of the following: carcinomas, sarcomas, osteosarcoma, leukemias, and lymphomas; tumor angiogenesis and metastasis; skeletal dysplasia; hepatic disorders; and hematopoietic and/or myeloproliferative disorders. Exemplary disorders include, but are not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, or retinoblastoma. Preferably, the cancer is one of the above-mentioned cancers responsive to activation of PPARgamma.

Cardiovascular diseases may, for example, be atherogenesis, atherosclerosis or atherosclerotic disorders, vascular restinosis, cardiomyopathy, or myocardial fibrosis. or any of the cardiovascular diseases mentioned above.

The inflammation may be, for example, a chronic inflammation, preferably any of the chronic inflammations mentioned herein above.

Diabetes mellitus refers to a disease process derived from multiple causative factors and characterized by elevated levels of glucose in blood, or hyperglycemia. Uncontrolled hyperglycemia is associated with increased and premature morbidity and mortality. At least two types of diabetes mellitus have been identified: (i) Type I diabetes, or Insulin Dependent Diabetes Mellitus (IDDM), which is the result of a complete lack of insulin, the hormone that regulates glucose utilization under normal physiological conditions, and (ii) the Type II diabetes, or Non Insulin Dependent Diabetes Mellitus (NIDDM). NIDDM is a complex disease derived from multiple causative factors, which can be addressed in some cases by increasing circulating insulin levels.

Pharmaceutical Formulations and Methods of Administration

In accordance with the methods and compositions of the present invention, one or more of the compounds described herein (preferably a PPAR modulator, a TP antagonist and/or TS inhibitor described above, such as (Z)-6-((2S,4S,5R)-2-(2-chlorophenyl)-4-(2-hydroxyphenyl)-1,3-dioxan-5-yl) hex-4-enoic acid) may be administered to a mammal in a variety of forms depending on the selected route of administration, as will be understood by those skilled in the art. The compositions of the invention may be administered orally, nasally, topically, via pulmonary administration or parenterally, the latter route including intravenous and subcutaneous administration. Parenteral administration may be by continuous infusion over a selected period of time.

Forms for injectable use include sterile aqueous solutions or dispersion and sterile powders for the extemporaneous preparation of sterile injectable solutions or dispersions. In all cases, the form must be sterile and must be fluid to the extent that easy syringability exists.

For ease of administration by the patient, oral or other non-invasive modes of administration are preferred, e.g. patches, suppositories and the like. The compounds may be orally administered with an inert diluent or with an assimilable edible carrier, or it may be enclosed in hard or soft shell gelatin capsules, compressed into tablets or incorporated directly with the food of the diet. For oral therapeutic administration, a compound may be incorporated with excipient and used in the form in ingestible tablets, buccal tablets, troches, capsules, elixirs, suspensions, syrups, wafers and the like.

Compositions containing one or more compounds of the present invention can also be administered in a solution or emulsion contained within phospholipid vesicles called liposomes. The liposomes may be unilamellar or multilamellar and are formed of constituents selected from phosphatidylcholine, dipalmitoylphosphatidylcholine, cholesterol, phosphatidylethanolamtine, phosphatidylserine, dimyristoylphosphatidylcholine and combinations thereof. The multilamellar liposomes comprise multilamellar vesicles of similar composition to unilamellar vesicles, but are prepared so as to result in a plurality of compartments in which the compounds in solution or emulsion are entrapped. Additionally, other adjuvants and modifiers may be included in the liposomal formulation such as polyethyleneglycol, or other materials.

The liposomes containing compositions may also have modifications such as having antibodies immobilized on the surface of the liposome in order to target their delivery.

In one embodiment of the present invention is a pharmaceutical composition for administration to subjects in a biologically compatible form suitable for administration in vivo for treating one of the clinical conditions described above in the section "Clinical conditions," said method comprising a safe and effective amount of a compound alone, or in combination with other agents and/or pharmaceutical carriers. For example, the compounds of the invention may be used to treat insulin resistance and/or diabetes in combination with an agent effective against dislipidemia, such as a drug of the fibrate class, e.g., Bezafibrate. The examples of some other agents are insulin sensitizers, PPARγ agonists, glitazones, troglitazone, pioglitazone, englitazone, MCC-555, BRL 49653, biguanides, metformin, phenformin, insulin, insulin minetics, sulfonylureas, tolbutamide, glipizide, alpha-glucosidase inhibitors, acarbose, cholesterol lowering agent, HMG-CoA reductase inhibitors, lovastatin, simvastatin, pravastatin, fluvastatin, atrovastatin, rivastatin, other statins, sequestrates, cholestyramine, colestipol, dialkylaminoalkyl derivatives of a cross-linked dextran, nicotinyl alcohol, nicotinic acid: a nicotinic acid salt, PPARalpha agonists, fenofibric acid derivatives, gemfibrozil, clofibrate, fenofibrate, inhibitors of cholesterol absorption, beta-sitosterol, acryl CoA:cholesterol acyltransferase inhibitors, melinamide, probucol, PPARdelta agonists, antiobesity compounds, fenfluramine, dexfenfluramine, phentiramine, sulbitramine, orlistat, neuropeptide Y5 inhibitors, $\beta_3$ adrenergic receptor agonists, and ileal bile acid transporter inhibitors.

The composition may be administered to any living organism in need of such treatment including humans and animals as the composition has efficacy in vivo. By safe and effective, as used herein, is meant providing sufficient potency in order to decrease, prevent, ameliorate, or treat the disease affecting the subject while avoiding serious side effects. A safe and effective amount will vary depending on the age of the subject, the physical condition of the subject being treated, the severity of the disorder, the duration of treatment and the nature of any concurrent therapy, and its determination is within the skill of the ordinary physician. The compositions are formulated and administered in the same general manner as described herein. The compounds of the present invention may be used effectively alone or in combination with one or more additional active agents. Combination therapy includes administration of a single pharmaceutical dosage composition, which contains a compound of the present invention and one or more additional active agents, as well as administration of a compound of the present invention and each active agent in its own separate pharmaceutical dosage. For example, a compound of the present invention and an insulin secretagogue such as sulfonylureas, thiazolidinediones, biguanides, meglitinides, insulin or beta-glucosidase inhibitors can be administered to the patient together in a single oral dosage composition such as a capsule or tablet, or each agent administered in separate oral dosages. Where separate dosages are used, a compound of the present invention and one or more additional active agents can be administered at essentially the same time, i.e., concurrently or at separately staggered times, i.e., sequentially; combination therapy is understood to include all these regimens.

A therapeutically active amount of a pharmaceutical composition of the present invention may also vary according to factors such as the disease state, age, sex, and weight of the subject and the ability of a compound to elicit a desired response in the subject. Dosage regimens may be adjusted to provide the optimum therapeutic response. For example, several divided doses may be administered daily or the dose may be proportionally reduced as indicated by the exigencies of the therapeutic situation.

A dose of around 0.01 mg/kg is likely a suitable initial dosage for a mammal and this dosage may be adjusted as required to provide a safe and effective amount. Thus, the dosage will initially typically be 0.01 to 100 mg/kg, such as 0.1 to 50 mg/kg, preferably 0.1 to 10 mg/kg, preferably 0.5 to 5 mg/kg, more preferably 1 to 5 mg/kg. For an adult human being the dose will in general be 0.01-20 mg/kg, preferably 0.1 to 10 mg/kg, more preferably 0.5 to 5 mg/kg, such as in the range of 1 to 200 mg total, for example 1 to 125 mg in total, for example 5 mg in total, preferably administered once or twice daily.

By pharmaceutically acceptable carrier as used herein is meant one or more compatible solid or liquid delivery systems have innocuous physiological reactions when administered to a subject. Some examples include but are not limited to starches, sugars, cellulose and its derivatives, powdered tragacanth, malt, gelatin, collagen, talc, stearic acids, magnesium stearate, calcium sulfate, vegetable oils, polyols, agar, alginic acids, pyrogen free water, isotonic saline, phosphate buffer, and other suitable non-toxic substances used in pharmaceutical formulations. Other excipients such as wetting agents and lubricants, tableting agents, stabilizers, anti-oxidants, and preservatives are also contemplated.

The compositions described herein can be prepared by known methods for the preparation of pharmaceutically acceptable compositions which can be administered to subjects, such that an effective quantity of the compounds or analogs is combined in a mixture with a pharmaceutical acceptable carrier. Suitable carriers are described for example in Remington's Pharmaceutical Sciences (Mack Publishing Company, Easton, Pa., USA, 1985). On this basis the compositions include, albeit not exclusively, solutions of the compounds in association with one or more pharmaceutical acceptable vehicles or diluents, and contained in buffered solutions with a suitable pH and iso-osmotic with the physiological fluids.

In one preferred embodiment of the invention the compounds of the invention (preferably the PPAR modulator, TP receptor antagonist and/or TS inhibitor), such as any of the compounds of formula IX, for example any of the compounds of formula X, such as any of the compounds of formula XI, for example any of the compounds of formula XII, such as any of the compounds of formula XIII, such as any of the compounds of formula XIV, for example (Z)-6-((2S,4S,5R)-2-(2-chlorophenyl)-4-(2-hydroxyphenyl)-1,3-dioxan-5-yl(hex-4-enoic acid are to be administered in admixture with suitable pharmaceutical excipients, diluents or carriers, in particular with pharmaceutical excipients, diluents or carriers suitable for immediate-, delayed-, modified-, sustained-, dual-, controlled-release or pulsatile delivery of said compounds.

For example, the compounds to be used in accordance with the invention can be administered orally, buccally or sublingually in the form of tablets, capsules (including soft gel capsules), ovules, elixirs, solutions or suspensions, which may contain flavouring or colouring agents, for immediate-, delayed-, modified-, sustained-, dual-, controlled-release or pulsatile delivery applications. The compounds of the invention may also be administered via fast dispersing or fast dissolving dosage forms. In a preferred embodiment of the invention the compounds (preferably the PPAR modulator, TP receptor antagonist and/or TS inhibitor, such as any of the compounds of formula IX, for example any of the compounds of formula X, such as any of the compounds of formula XI, for example any of the compounds of formula XII, such as any of the compounds of formula XIII, such as any of the compounds of formula XIV, for example (Z)-6-((2S,4S,5R)-2-(2-chlorophenyl)-4-(2-hydroxyphenyl)-1,3-dioxan-5-yl)hex-4-enoic acid are administered in a pharmaceutical composition for delayed-, modified-, sustained-, or controlled-release.

Delayed-, modified-, sustained-, or controlled-release dosage forms may contain the above mentioned excipients together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer, cremophor, corn oil glyceride, propylene glycol and mixtures thereof. Modified release and controlled-release dosage forms may contain one or a combination of release rate modifying excipients. Release rate modifying excipients may be present both within the dosage form i.e. within the matrix, and/or on the dosage form, i.e. upon the surface or coating.

In addition to the above described formulations, medicaments containing a compound for use in accordance with the present invention may furthermore be prepared by conventional techniques, e.g. as described in Remington: The Science and Practice of Pharmacy 1995, edited by E. W. Martin, Mack Publishing Company, 19th edition, Easton, Pa.

The following examples describe specific aspects of the invention to illustrate the invention and should not be construed as limiting the invention, as the examples merely provide specific methodology useful in the understanding and practice of the invention.

EXAMPLES

Example 1:

Synthesis of (Z)-6-(-2-(2-chlorophenyl)-4-(2-hydroxyphenyl)-1,3-dioxan-5-yl)hex-4-enoic acid This example describes the synthesis of (Z)-6-[(2-(2-chlorophenyl)-4-(2-hydroxyphenyl)-1,3-dioxan-5-yl]hex-4-enoic acid, also referred to herein as DPD, according to Scheme 2 (SN1 in Table II).

Scheme 2

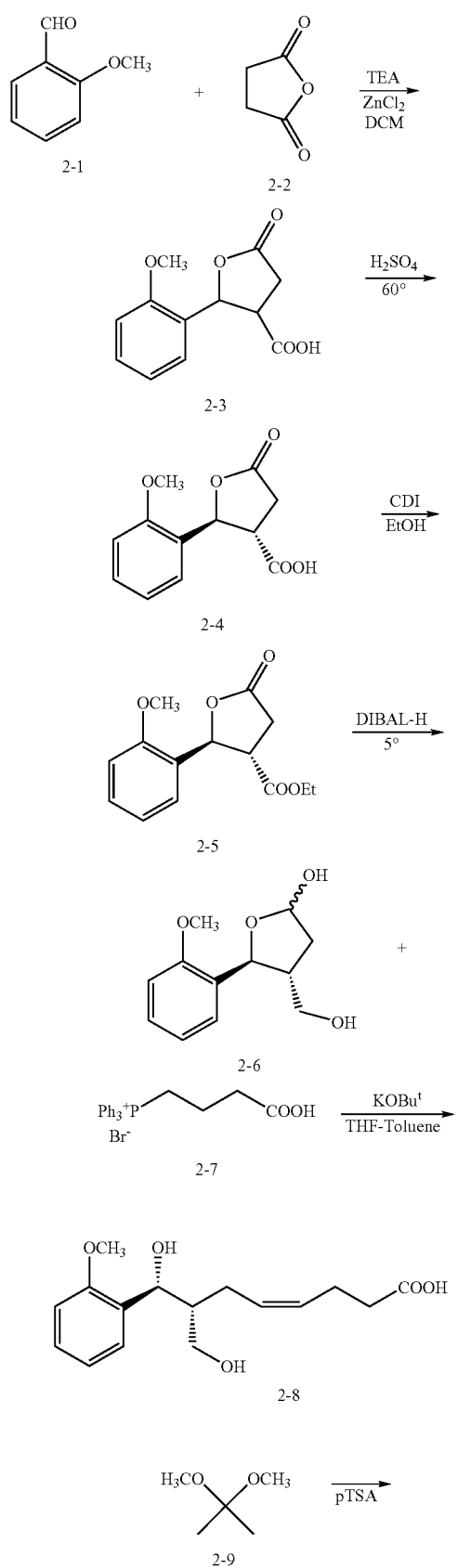

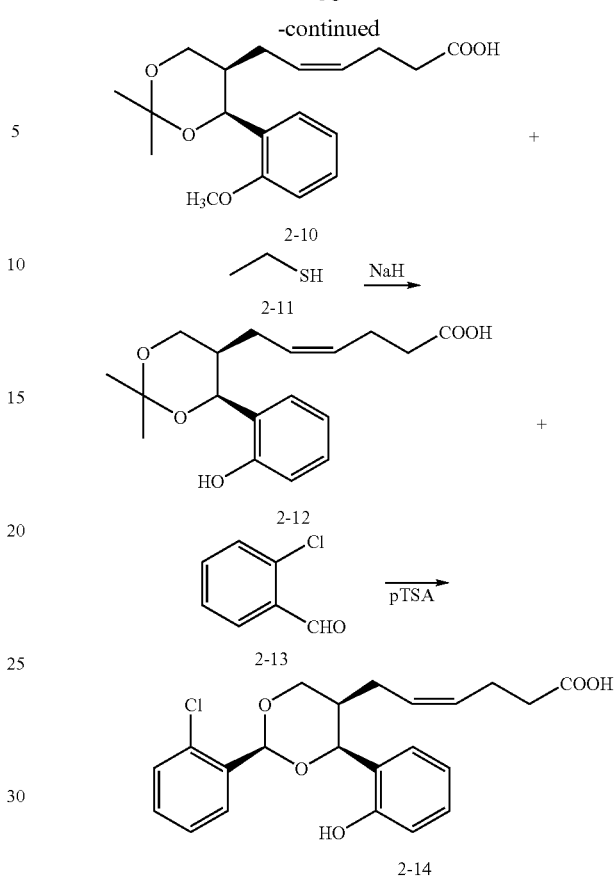

Synthesis of racemic 2-methoxy-paraconic acid (2-3) as a cis/trans mixture: A 20 L double-jacketed glass reactor was charged with 260 g o-methoxybenzaldehyde, 286 g succinic anhydride, 572 g anhydrous zinc chloride and 2600 mL anhydrous DCM. The mixture was stirred and cooled to 2° C. An amount of 533 mL triethylamine was added over a period of 30 min. The mixture was then allowed to stir at ambient temperature for 24 h. An amount of 1690 mL 2M HCl was added, followed by 2600 mL ethyl acetate. The mixture was stirred vigorously for 5 min. The aqueous phase was extracted with 2000 mL ethyl acetate. The combined organic extracts were washed with 650 mL saturated brine, followed by a wash with 3×2600 mL saturated sodium bicarbonate. The combined aqueous extracts were then washed with ethyl acetate. The aqueous extracts were acidified to pH 2 using concentrated HCl. A yellow oil separated. The mixture was extracted twice using 2000 mL ethyl acetate. The organic phase was washed four times with 1000 mL brine and evaporated on a Buchi R220 rotavap employing a heating bath temperature of 45° C. To the remaining residue were added 4000 mL toluene. The mixture was heated to 110° C. 1 L of toluene was distilled off. The remainder was allowed to cool to room temperature, and was left standing for 48 h during which pure 2-methoxy-paraconic acid crystallized. The crystalline material was collected, filtered and dried in vacuo at 45° C. in a vacuum oven until constant weight.

Yield: 220 g (49%). cis/trans ratio: 46/54

Conversion of cis- and trans racemic methoxy-paraconic acid to all-trans-2-methoxy paraconic acid (2-4): 1020 g methoxyparaconic acid was added to a mixture of 1729 mL concentrated sulfuric acid and 2570 mL water. The mixture was allowed to stir at room temperature for 18 h. A cis/trans ratio of 33:64 was obtained. The mixture was then heated to 60° C. for 2.5 h. A cis/trans ratio of 11:89 was obtained (analysis by HPLC). The mixture was then allowed to cool to room temperature, and subsequently filtered. The solid material was redissolved in ethyl acetate, and washed with water and brine. The organic layer was dried over MgSO$_4$ and evaporated. A cis/trans ratio of 6:94 was observed. The solid material was recrystallized from hot toluene. The obtained crystalline material was dried in vacuo at 40° C. for 48 h.

Yield: 855 g (84%). cis/trans ratio: 8/92. Melting point: 132-133° C.

NMR (CDCl$_3$, 300 MHz): 2.9 (2H, d), 3.4 (1H, m), 3.83 (3H, s), 5.85 (1H, d), 6.8-7.4 (4H, m)

Esterification of racemic methoxy-paraconic acid, (2-5): 193 g of methoxy-paraconic acid were dissolved in 600 mL THF. To the mixture were added 145 g CDI (899 mmol, 1.1 eq), and the mixture was stirred for 10 min. An amount of 65 mL absolute ethanol (or methanol to make the methyl ester) was added, and the mixture was stirred till complete (~120 min).

The crude reaction mixture was extracted using ethyl acetate and saturated sodium bicarbonate. The organic phase was washed with 0.5N HCl and brine. After evaporation, an amount of 188 g of the desired ethyl ester were obtained.

Reduction of racemic methoxy-paraconic acid, ethyl ester (2-6): Preparation of racemic lactol: To 105 g ethyl ester (397 mmol) in 700 mL toluene at 5° C. were Added 3 eq. DIBAL-H (1.19 mol, 1.19 L 1M solution). The mixture was stirred for 60 min at room temperature and quenched with methanol. Ethyl acetate (2.5 L) and water (700 mL) were added. After phase separation, the aqueous phase was again extracted with EtOAc. The organic layer was then washed with brine, filtered and evaporated. The oily residue was recrystallized from chloroform/hexanes. The solids were filtered and dried in vacuo.

Yield: 53 g (237 mmol, 59%).

Wittig reaction employing racemic lactol-Synthesis of racemic diol (2-8): An amount of 191 g carboxypropyltriphenylphosphonium bromide, 1000 mL anhydrous toluene and 100 g potassium t-butoxide were mixed at 80° C. for 30 min. The mixture was cooled to room temperature. An amount of 25 g purified racemic lactol (114.5 mmol) pre-dissolved in 180 mL anhydrous THF were slowly added. The reaction was continued for 60 min. The crude reaction mixture was poured into 1500 mL ice-water, 300 mL ethyl acetate were added. The aqueous phase was re-extracted with 300 mL ethyl acetate. The aqueous phase was then acidified with 2N HCl, and extracted 3 times using 300 mL ethyl acetate. The solids that had formed were filtered off. The organic phase was evaporated. To the evaporated residue were added 500 mL diethyl ether. The flask was swirled for 10 min, and the solids were filtered off. The filtrate was extracted 3 times with saturated sodium bicarbonate solution. The aqueous phase was then acidified to pH 4 using 2M HCl. The aqueous phase was then extracted 3 times employing 200 mL of ethyl acetate. The organic phases were combined, dried over MgSO$_4$ and evaporated to yield 45 g of material Column chromatography: Racemic diol was purified over silica gel (35 cm column length, 4 cm diameter). Racemic diol was dissolved in a minimum of ethyl acetate and applied to the column. 1 L of ethyl acetate (60%)/hexanes (40%) was added to a volumetric cylinder. 300 mL of EtOAc/hexanes was taken from the cylinder and added to the column. The remaining 700 mL of EtOAc/hexanes in the cylinder were diluted to 1 L using ethyl acetate. 300 mL of the new EtOAc/hexanes solution were then added to the column and were allowed to pass through the column. The remaining 700 mL of EtOAc/hexanes in the cylinder were again diluted to 1 L using ethyl acetate. 300 mL of the new EtOAc/hexanes solution were then added to the column and were allowed to pass through the column. The remaining 700 L of EtOAc/hexanes in the cylinder were diluted once more to 1 L using ethyl acetate. 300 mL of the new EtOAc/hexanes solution were then added to the column and were allowed to pass through the column. Pure fractions of racemic diol were collected and evaporated to yield 26 g of pure racemic diol.

Yield: 26 g (88.3 mmol, 79%)

Conversion of racemic diol into racemic acetonide (2-10): 26 g (88 mmol) of purified diol was mixed with 260 mL dimethoxypropane and 26 mg p-TsOH. The mixture was allowed to stir at ambient temperature overnight. Three drops of triethylamine were added, and the mixture was evaporated. To the remaining residue were added 150 mL hexane, and the mixture was stirred overnight. The solids were filtered off and dried to yield 25 g (75 mmol) of racemic acetonide.

Yield: 85%

De-methylation of racemic acetonide (2-12): A suspension of sodium hydride and ethanethiol was prepared by adding 16.7 g of ethanethiol to a mixture of 21.5 g NaH in 375 mL DMPU. The suspension was heated to 80° C., and allowed to cool to ambient temperature.

15 g of racemic acetonide were dissolved in 75 mL DMPU and added to the suspension of EtSH/NaH. The mixture was heated at 130° C. for 2 h. The reaction mixture was then poured into ice-water and extracted with DCM. The aqueous layer was acidified using 2N HCl, and extracted with ethyl acetate. The organic layer was washed with brine and evaporated to dryness.

Yield: 16.5 g (crude).

Preparation of racemic final compound (2-14): An amount of 28 mmol de-methylated racemic acetonide was mixed with 15 mL 2-chlorobenzaldehyde, 0.5 g of p-TsOH, and 60 mL of toluene. The mixture was stirred for 24 h and evaporated. The crude reaction mixture was purified using silica gel chromatography employing a Biotage Horizon® chromatography instrument. The mixture was purified using DCM (19)/methanol(1) to yield 6.5 g of a solid after evaporation.

Yield: 6.5 g (16.7 mmol, 59%)

Scheme 3: Synthetic route for PPAR modulators described in Table I (and Table II)

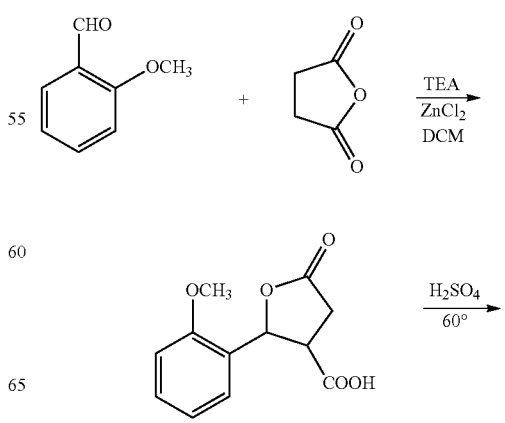

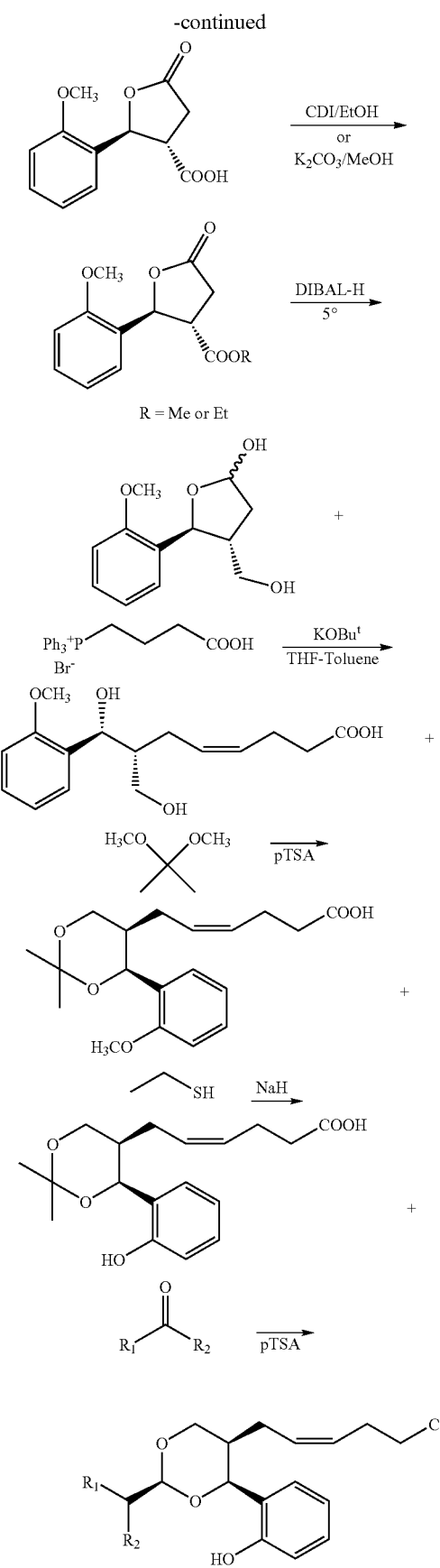
TABLE I
| R₁ | R₂ |
|---|---|
| 2,3-dichlorophenyl | H |
| 2-pyridyl | H |
| 2-fluorophenyl | H |
| 7-methylbenzo[d][1,3]dioxol-4-yl | H |
| 1,1-dimethylcyclohexyl | |
| 2-methyl-4'-methoxydiphenyl ether | H |
| 1-Boc-4,4-dimethylpiperidin-4-yl | |
| 1-methylnaphthalen-2-yl | H |
| 2-methylbiphenyl | H |
| n-hexyl | H |
| (E)-pent-2-enyl | H |
| 7-chloro-4-methyl-2H-chromen-2-one | H |

TABLE I-continued

| R₁ | R₂ |
|---|---|
| 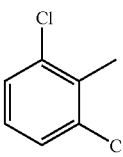 | H |
| 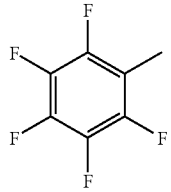 | H |
| 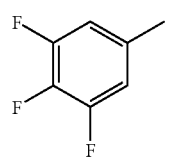 | H |
| 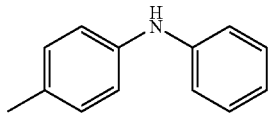 | H |
| 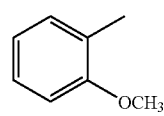 | H |
| 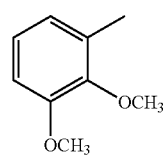 | H |
|  | H |
| 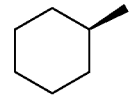 | H |
| 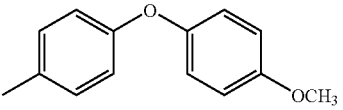 | H |

Example 2:

Synthesis of PPAR Modulator 2 (SN2, Table II)

This example describes the synthesis of PPAR modulator 2 (SN2, Table II) according to Scheme 3. An amount of 100 mg (0.31 mmol) racemic acetonide (6-[4-(2-hydroxyphenyl)-2,2-dimethyl-[1,3]dioxan-5-yl]-hex-4-enoic acid) 2-12 as described in Example 1 was mixed with 1 mL toluene and 10 mg p-toluenesulfonic acid. To the mixture was were added 2 eq (0.62 mmol, 108 mg) of 2,3-dichlorobenzaldehyde. The mixture was stirred for 24 h and evaporated using a nitrogen flow. The crude reaction mixture was purified over a silica gel column, using methanol(1)/DCM(19). Pure fractions were identified by TLC, collected, evaporated and analyzed by HPLC and mass spectrometry.

Mass spectrum (electrospray, negative mode): [M-H]—=435

Example 3:

Synthesis of PPAR Modulator 6 (SN6, Table II)

This example describes the synthesis of PPAR modulator 6 (SN6, Table II) according to Scheme 3. An amount of 100 mg (0.31 mmol) racemic acetonide was mixed with 1 mL toluene and 10 mg p-toluenesulfonic acid. To the mixture were added 2 eq (0.62 mmol, 70 mg) of cyclohexanone. The mixture was stirred for 24 h and evaporated using a nitrogen flow. The crude reaction mixture was purified over a silica gel column, using methanol(1)/DCM(19). Pure fractions were identified by TLC, collected, evaporated and analyzed by HPLC and mass spectrometry.

Mass spectrum (electrospray, negative mode): [M-H]—=359

Example 4:

Synthesis of PPAR Modulator 8 (SN8, Table II)

This example describes the synthesis of PPAR modulator 8 (SN8, Table II) according to Scheme 3.

Preparation of N-Boc 4-oxopiperidine: An amount of 2 g 4-oxopiperidine was dissolved in 20 mL dioxane/water. To the mixture was added 2 eq. Sodium bicarbonate, followed by 1.0 eq. Boc₂O. The mixture was stirred for 4 h. Ethyl acetate (100 mL) was added. The organic phase was washed twice using 0.2N HCl and brine. The organic phase was then dried over magnesium sulfate and evaporated to yield oil which crystallized. An amount of 100 mg (0.31 mmol) racemic acetonide was mixed with 1 mL toluene and 10 mg p-toluenesulfonic acid. To the mixture were added 2 eq. (0.62 mmol) of N-Boc-4-oxopiperidine. The mixture was stirred for 24 h and evaporated using a nitrogen flow. The crude reaction mixture was purified over a miniature silica gel column, using methanol(1)/DCM(19). Pure fractions were identified by TLC, collected, evaporated and analyzed by HPLC and mass spectrometry.

Mass spectrum (electrospray, negative mode): [M-H]—=460

The biological assays referred to hereinbelow were carried out with the reaction product including the Boc-protecting group still present on the spiro-piperidine ring.

Example 5:

Synthesis of PPAR Modulator 9 (SN9, Table II)

This example describes the synthesis of PPAR modulator 9 (SN9, Table II) according to Scheme 3.

Preparation of 1-naphthalenecarboxaldehyde An amount of 3.87 mL oxalyl chloride (44.24 mmol) was dissolved in 100 mL DCM. The mixture was cooled to −60° C. An amount of 5.6 mL DMSO was added dropwise using a syringe. The mixture was stirred for 15 min. A solution of 5 g of naphthalene-1-methanol in 75 mL DCM was added dropwide. The reaction was continued for 1 h at −60° C. An amount of 20 mL triethylamine was added. The mixture was allowed to attain 15° C. The mixture was transferred to an extraction funnel, washed with water, 1M HCl, water and brine. The organic layer was then dried over magnesium sulfate and evaporated. The crude product was sufficiently pure to be used without further purification in the next step.

An amount of 100 mg (0.31 mmol) racemic acetonide (2-12 as described above) prepared according to Example 1 was mixed with 1 mL toluene and 10 mg p-toluenesulfonic acid. To the mixture were added 2 eq. (0.62 mmol, 97 mg) of 1-naphthalenecarboxaldehyde. The mixture was stirred for 24 h and evaporated using a nitrogen flow. The crude reaction mixture was purified over a silica gel column, using methanol (1)/DCM(19). Pure fractions were identified by TLC, collected, evaporated and analyzed by HPLC and mass spectrometry.

Mass spectrum (electrospray, negative mode): [M-H]—=417

Example 6:

Synthesis of PPAR Modulator 11 (SN11, Table II)

This example describes the synthesis of PPAR modulator 11 (SN11, Table II) according to Scheme 3.

An amount of 100 mg (0.31 mmol) racemic acetonide (2-12 from Example 1) was mixed with 1 mL toluene and 10 mg p-toluenesulfonic acid. To the mixture were added 2 eq (0.62 mmol, 62 mg) of hexane. The mixture was stirred for 24 h and evaporated using a nitrogen flow. The crude reaction mixture was purified over a silica gel column, using methanol (1)/DCM(19). Pure fractions were identified by TLC, collected, evaporated and analyzed by HPLC and mass spectrometry.

Mass spectrum (electrospray, negative mode): [M-H]—=361

Example 7:

Synthesis of PPAR Modulator 13 (SN13, Table II)

This example describes the synthesis of PPAR modulator 13 (SN13, Table II) according to Scheme 3.

An amount of 100 mg (0.31 mmol) racemic acetonide was mixed with 1 mL toluene and 10 mg p-toluenesulfonic acid. To the mixture were added 2 eq (0.62 mmol, 130 mg) of o-2-oxo-4-a,8a-dihydro-2H-chromene-4-carbaldehyde. The mixture was stirred for 24 h and evaporated using a nitrogen flow. The crude reaction mixture was purified over a miniature silica gel column, using methanol(1)/DCM(19). Pure fractions were identified by TLC, collected, evaporated and analyzed by HPLC and mass spectrometry.

Mass spectrum (electrospray, negative mode): [M-H]—=469

Example 8:

Synthesis of PPAR Modulator 19 (SN19, Table II)

This example describes the synthesis of PPAR modulator 19 (SN19, Table II) according to Scheme 3.

An amount of 100 mg (0.31 mmol) racemic acetonide was mixed with 1 mL toluene and 10 mg p-toluenesulfonic acid. To the mixture were added 2 eq (0.62 mmol, 103 mg) of 2,3-dimethoxybenzaldehyde. The mixture was stirred for 24 h and evaporated using a nitrogen flow. The crude reaction mixture was purified over a silica gel column, using methanol (1)/DCM(19). Pure fractions were identified by TLC, collected, evaporated and analyzed by HPLC and mass spectrometry.

HPLC: retention time (gradient A): 15.23, 15.39 min, 95% (sum of 1:1 mixture of isomers)

Mass spectrum (electrospray, negative mode): [M-H]—=427.2

Example 9:

Synthesis of PPAR Modulator 14 (SN14, Table II)

This example describes the synthesis of PPAR modulator 14 (SN14, Table II) according to Scheme 3

To a stirred solution of diol (0.08 g, 0.27 mmol) in DCM (10 mL) at room temperature was added 2,6-dichlorobenzaldehyde (0.07 g, 0.40 mmol) and pTSA (3 mg). The reaction mixture was stirred for 8 h and quenched with triethylamine (2-3 drops) before concentration in vacuo. The residue was purified by column chromatography on silica gel, eluted with hexane/EtOAc (8:2) to give the acetal (100 mg, 45% yield) as colorless oil.

$^1$HNMR (200 MHz, CDCl$_3$): δ 7.55 (d, 1H, J=7.8 Hz), 7.37-7.13 (m, 4H), 7.00 (t, 1H, J=7.8 Hz), 6.87 (d, 1H, J=7.8 Hz), 6.46 (s, 1H), 5.51-5.15 (m, 3H), 4.24-4.14 (m, 2H), 3.84 (s, 3H), 2.99-2.81 (m, 1H), 2.40-2.27 (m, 4H), 1.93-1.87 (bd, 1H, J=10.9 Hz), 1.73-1.67 (bd, 1H, J=10.9 Hz). MS: 450 (M$^+$)

Example 10:

Synthesis of PPAR Modulator 15 (SN15, Table II)

This example describes the synthesis of PPAR modulator 15 (SN15, Table II) according to Scheme 3. Compound 2-12 from Scheme-2, Example 1 (100 mg, 0.31 mmol) was dissolved in THF (5 mL), and a catalytic amount of pTsOH (5 mg) was added at room temperature. The reaction mixture was kept for stirring at room temperature for 8 h. 2,3,4,5,6-Pentafluoro benzaldehyde (158 mg, 0.62 mmol) was added to the reaction mass; once again catalytic amount of pTsOH was added. Reaction conditions were maintained for further 24 h. After the completion of reaction, dry Et$_3$N was added to adjust to pH=7. The solvent was removed under vacuum and the resulting crude mixture was purified by column chromatography to obtain final product 15.

Scheme 4: Synthetic route for compounds described in Table III (and Table II)

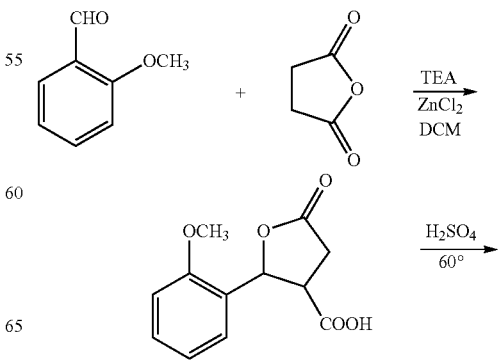

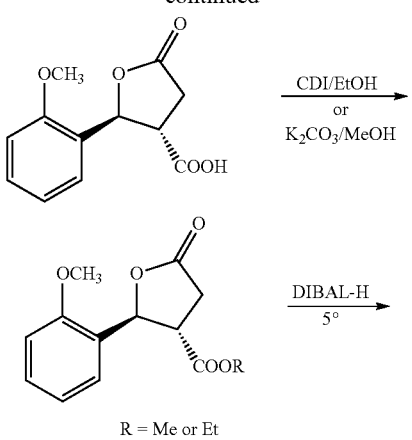

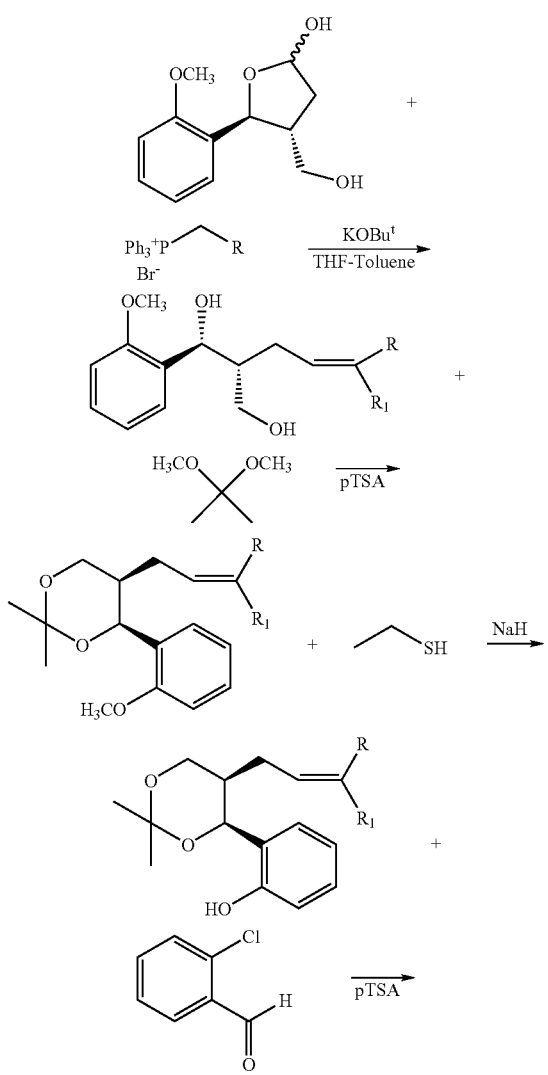

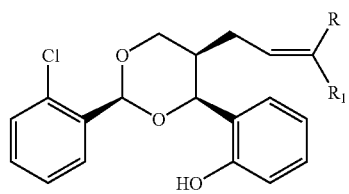

TABLE III

| R | $R_1$ |
|---|---|
| ![propyl]~~~COOH | H |
| ![butyl]~~~~COOH | H |
| H | COOH |
| ethyl-furyl-COOH | H |

Example 11:

Synthesis of PPAR Modulator 23 (SN23, Table II)

This example describes the synthesis of PPAR modulator 23 (SN23, Table II) according to Scheme 4.

Wittig reaction An amount of 10 g (22.56 mmol) BrPPh$_3$(CH$_2$)$_4$CO$_2$H was mixed with 5.06 g (45 mmol) KOtBu in 60 mL dry toluene. The mixture was heated to 80° C. for 30 min and allowed to cool to ambient temperature. An amount of 1.26 g racemic lactol in 10 mL anhydrous THF was added and the reaction was continued for 2 h. Work-up was as for preparation of 2-8 Scheme-2.

Yield: 3.3 g (crude, used as is in the next step).

Preparation of acetonide The diol, obtained in the previous step, was dissolved in 40 mL dimethoxypropane. An amount of 25 mg p-TsOH was added and the reaction was stirred for 24 h. A drop of triethylamine was added and the mixture was evaporated. The crude mixture was filtered over a small silica gel column.

Yield: 1.6 g

De-methylation of acetonide An amount of 1.91 mL ethanethiol (25.83 mmol) was mixed with 50 mL DMPU. An amount of 51.7 mmol NaH (2.06 g 60% dispersion in oil) was added and the mixture was heated to 80° C. for 30 min. The mixture was cooled to ambient temperature. A solution of 1.5 g acetonide (4.3 mmol) in 7.5 mL DMPU was added and the mixture stirred for 2 h at 125° C. The crude mixture was poured into ice-water, and extracted with 2×50 mL DCM. The aqueous phase was acidified with 2N HCl, then extracted with EtOAc, and finally washed with brine. The organic phase was evaporated to yield 1.6 g of hydroxy-acetonide.

Reaction with 2-chlorobenzaldehyde The hydroxy-acetonide (1.6 g, crude) was mixed with 2 mL 2-chlorobenzaldehyde, 8 mL anhydrous toluene, and 50 mg pTsOH. The mixture was stirred for 24 h, evaporated, and purified by silica gel column chromatography.

Mass spectrum (electrospray, negative mode): [M-H]—=415

Example 12:

Synthesis of PPAR Modulator 17 (SN17, Table II)

This example describes the synthesis of PPAR modulator 17 (SN17, Table II) according to Scheme 4.

An amount of 100 mg (0.31 mmol) racemic acetonide was mixed with 1 mL toluene and 10 mg p-toluenesulfonic acid. To the mixture was added 2 eq (0.62 mmol, 122 mg) of 4-phenylaminobenzaldehyde. The mixture was stirred for 24 h and evaporated using a nitrogen flow. The crude reaction mixture was purified over a miniature silica gel column, using methanol(1)/DCM(19). Pure fractions were identified by TLC, collected, evaporated and analyzed by HPLC and mass spectrometry.

Synthesis of methyl ester of o-methoxyparaconic acid: a) To a stirred solution of acid (5 g, 21.18 mmol) in dry DMF (150 mL) was added K$_2$CO$_3$ (29.2 g, 211.8 mmol) followed by methyl iodide (6.01 g, 42.3 mmol) at 0° C. and the reaction mixture was stirred for 5 h at room temperature. The reaction mixture was diluted with water (10 mL), DCM (30 mL) and the organic layer was separated. The aqueous layer was extracted with DCM (2×15 mL) and the combined organic layers were washed with brine (2×20 mL), dried over Na$_2$SO$_4$ and evaporated in vacuo to obtain the ester, which was pure enough to use in further reaction. (Yield: 4.34 g, 81.9%).

b) To a stirred solution of acid 5 (10 g, 42.3 mmol) in dry ether (60 mL) was added a freshly prepared diazomethane solution (200 mL solution, generated from 10 g of nitroso methyl urea) at 0° C. and stirred for 30 min at r. t. After complete disappearance of starting material, ether was evaporated to get the ester 6, which was used for the further reaction without purification. (Yield: 9.8 g, 98%). Yellow viscous oil $^1$H NMR (CDCl$_3$, 200 MHz): δ 7.38-7.22 (2H, m), 6.94-6.82 (m, 2H), 5.79 (d, J=6.2 Hz, 1H), 3.36-3.24 (m, 1H), 2.9-2.8 (m, 2H).

Example 13:

Synthesis of PPAR Modulator 34 (SN34, Table II)

This example describes the synthesis of PPAR modulator 34 (SN34, Table II).

A mixture of diol 7 (0.4 g, 1.36 mmol) and chlorobenzaldehyde dimethylacetal (0.28 g, 1.63 mmol) in dry toluene (2 mL) was stirred for overnight in the presence of catalytic p-toluenesulfonic acid (~5 mg) under nitrogen atmosphere. After complete disappearance of the starting material, the reaction mixture was neutralized with solid NaHCO$_3$; the solution was decanted from the reaction mixture and concentrated on rotary evaporator. The crude product was purified by column chromatography to yield benzylidine acetal.

Yield: 0.31 g (59%)

$^1$HNMR (CDCl$_3$, 200 MHz): δ 7.82 (d, J=7.8 Hz, 1H), 7.42 (d, J=7.8 Hz, 1H), 7.38-7.2 (m, 3H), 6.87 (t, J=7.8 Hz, 1H), 6.82 (d, J=8.6 Hz, 1H), 6.05 (s, 1H), 5.72 (d, J=15.6 Hz, 1H), 5.45 (d, J=2.3 Hz, 1H), 4.21 (t, J=15.6 Hz, 2H), 4.1 (q, J=7.0 Hz, 2H), 3.83 (s, 3H), 2.68-2.56 (m, 1H), 1.29 (t, J=7.0 Hz, 3H).

To a solution of this compound (0.2 g, 0.48 mmol) in THF:H$_2$O (4 mL, 3:1), was added LiOH.H$_2$O (0.3 g, 7.15 mmol), methanol (0.5 mL) and stirred for overnight at room temperature. The reaction mixture was neutralized with saturated aqueous solution of NaHSO$_4$ and extracted with DCM (2×10 mL). The combined organic layers were washed with brine (10 mL), evaporated on rotavapour and the crude product was purified by column chromatography.

Yield: 95 mg (51%)

$^1$HNMR (CDCl$_3$, 200 MHz): δ 7.83 (d, J=7.5 Hz, 1H), 7.32 (m, 1H), 7.2 (t, J=7.5 Hz, 1H), 6.87 (d, J=8.5 Hz, 1H), 6.9 (t, J=7.5, 6.6 Hz, 1H), 6.69 (m, 1H), 6.06 (s, 1H), 5.67 (d, J=16.1 Hz, 1H), 5.42 (s, 1H), 4.18 (dd, J=11.32 Hz, 2H), 3.84 (s, 3H), 2.58 (m, 1H), 2.09 (m, 2H). MS: 411 (M+Na)$^+$

Scheme-4a:

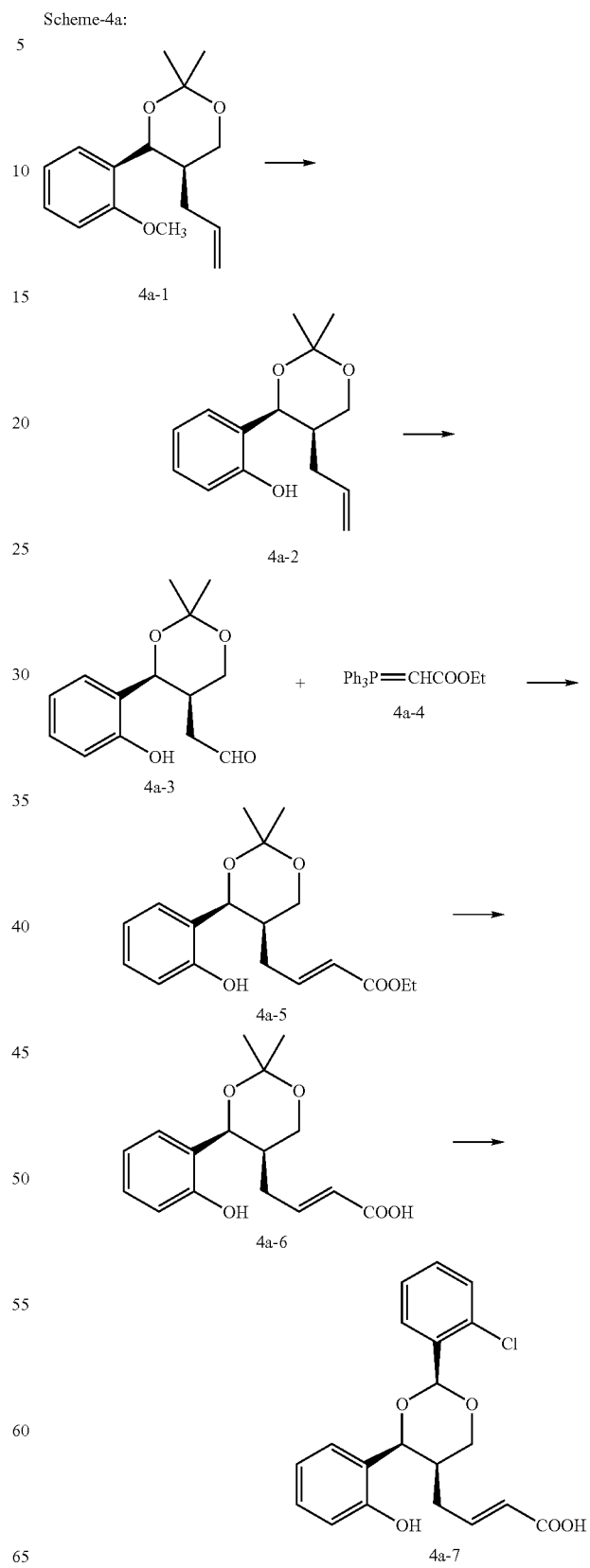

Example 14:

Synthesis of PPAR Modulator 25 (SN25, Table II)

This example describes the synthesis of PPAR modulator 25 of Table II.

Ethanethiol (0.7 mL, 9.5 mmol) was added to a stirred suspension of (60% in oil) NaH (0.38 g, 9.5 mmol) in dry DMF (8 mL) at 0-5° C. and stirred for 20-30 min. Compound 4a-1 (0.25 g, 0.95 mmol) in dry DMF (2 mL) was added slowly drop-wise to the above mixture maintaining the temperature. The reaction mass temperature was raised to 120-130° C. and maintained for 6-8 h. After the completion of reaction, the mass was cooled to 0-5° C. and quenched with 1N HCl (1 mL) by adjusting the pH 4-5. The compound was extracted with ethyl acetate (3×10 mL) and separated the aqueous layer. The combined organic fractions were collected, washed with brine water, dried over sodium sulphate (2 g) and concentrated in vacuo. The crude product was purified by column chromatography (elution with ethyl acetate:hexane; 2.5:7.5) to obtain pure 4a-2).

Yield: 155 mg (65.6%).

Compound 4a-2 (0.15 g, 0.6 mmol) was dissolved in a mixture of acetone and water in the ratio of 8:2 (10 mL). To the above mixture, $OsO_4$ (catalytic amount, 0.05M) and NMO (0.14 g, 1.2 mmol) were added and kept for stirring at room temperature for 8-10 h. The progress of the reaction was monitored by TLC. After the completion of reaction, it was quenched by saturated $Na_2S_2O_5$ solution (3 mL). The solvent acetone was removed under vacuum and the compound was extracted with ethyl acetate (3×10 mL). The combined organic fractions were collected, washed with brine water dried over sodium sulphate (2 g), concentrated on vacuum.

To a solution of the crude product (a diol not depicted in the scheme) in a mixture of THF: $H_2O$ (8:2, 10 mL), $NaIO_4$ (0.27 g, 1.8 mmol) was added at room temperature and kept for stirring for 1 h. After the completion of reaction, it was quenched by saturated $Na_2S_2O_5$ solution (3 mL). The compound was extracted with ethyl acetate (3×10 mL) and aqueous layer was separated. The combined organic fractions were collected, washed with brine water, dried over sodium sulphate (2 g) and concentrated on vacuum. The crude product 4a-3 was processed for further reaction.

To a solution of compound 4a-3 in dry benzene (10 mL), C2-Wittig ylide (0.15 g, 0.42 mmol) was added. The reaction mass was kept for stirring under inert conditions for 2-3 h at room temperature. Excess benzene was removed on rotary evaporator and thus resulting crude compound 4a-5 was subjected to purification by column chromatography. (Ethyl acetate:hexane; 0.5:9.5).

Yield: 0.11 g (95%)

$^1$HNMR ($CDCl_3$, 300 MHz): δ 8.1(s, 1H), 7.2-7.1 (t, J=6.1 Hz, 1H), 6.85-6.6 (m, 4H), 5.8-5.69 (d, J=15.7 Hz, 1H), 5.85 (m, 1H), 4.15-4.0 (q, J=6.1 Hz, 8.74, 3H), 3.80-3.70 (d, J=8.7 Hz, 1H), 2.7-2.55 (m, 1H), 2.15-2.05 (m, 1H), 1.72-1.65 (m, 1H), 1.60-1.40 (m, 6H), 1.25-1.11 (t, J=6.1 Hz, 3H), [M+Na$^+$]=343.1

To a solution of compound 4a-5 (0.11 g, 0.34 mmol) in a mixture of THF: $H_2O$ (8:2, 5 mL), LiOH.$H_2O$ (0.1 g, 2.4 mmol) was added at room temperature and kept for stirring for 8-10 h.

After the completion of reaction, it was quenched by saturated $NaHSO_4$ solution (1 mL) by adjusting the pH to 4-5. The compound was extracted with ethyl acetate (3×10 mL) and aqueous layer was separated. The combined organic fractions were collected, washed with brine water dried over sodium sulphate (2 g), concentrated on vacuum. The crude product 4a-6 was processed for further reaction.

Compound 4a-6 (85 mg, 0.29 mmol) was dissolved in THF, and a catalytic amount of pTSOH was added at room temperature. The reaction mixture was kept for stirring at room temperature for 6-8 h. o-Chlorobenzaldehyde (81 mg, 0.58 mmol) was added to the reaction mass; once again catalytic amount of pTSOH was added. Reaction conditions were maintained for further 5-6 h. After the completion of reaction dry $Et_3N$ was added by adjusting the pH=7. The solvent was removed under vacuum and the resulting crude mixture was purified by column chromatography to obtain final product 25 (Table II). (ethyl acetate:hexane;3.5:6.5).

Yield: 35 mg (32%)

The above compound HPLC purity is 79.2%, which was further purified by preparative HPLC to obtain the pure compound (98% pure, 15 mg).

$^1$HNMR ($CDCl_3$, 300 MHz): δ7.85-7.69(d, J=7.1 Hz, 1H), 7.5-7.30(m, 4H), 7.19-7.08(t, J=7.1 Hz, 1H), 7.08-7.0(d, J=7.1 Hz, 1H), 6.99-6.70 (m, 2H), 6.05(s, 1H), 5.95(s, 1H), 5.9-5.75(d, J=15.7 Hz, 1H), 5.5 (s, 1H), 4.4-4.1 (s, broad, 2H), 2.4-2.1(m, 4H), 2.9-2.7(m, 1H), 2.35-2.19 (d, J=7.1 Hz, 1H), 2.1-1.95 (d, J=7.1 Hz, 1H). [M$^+$+H$^+$]=374.1 HPLC: 98.93% (RT:4.12)

Scheme 5:

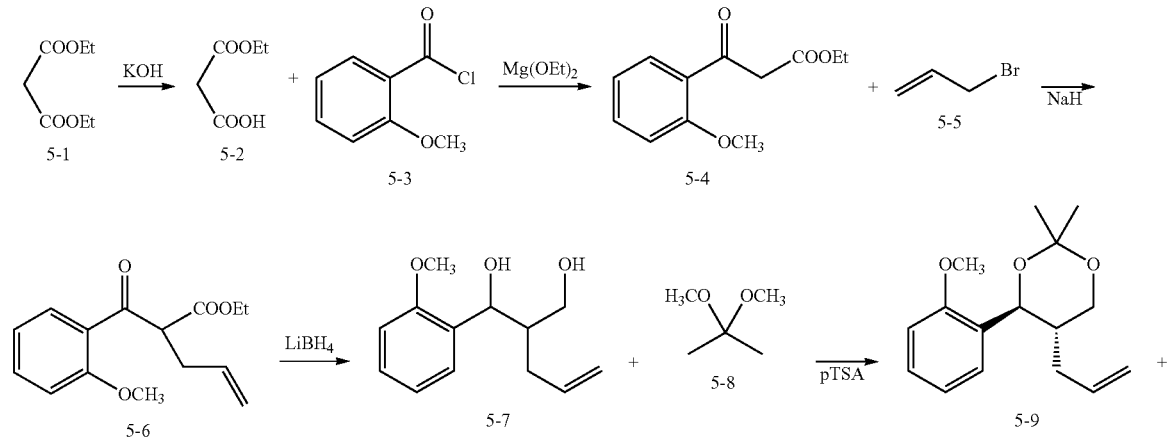

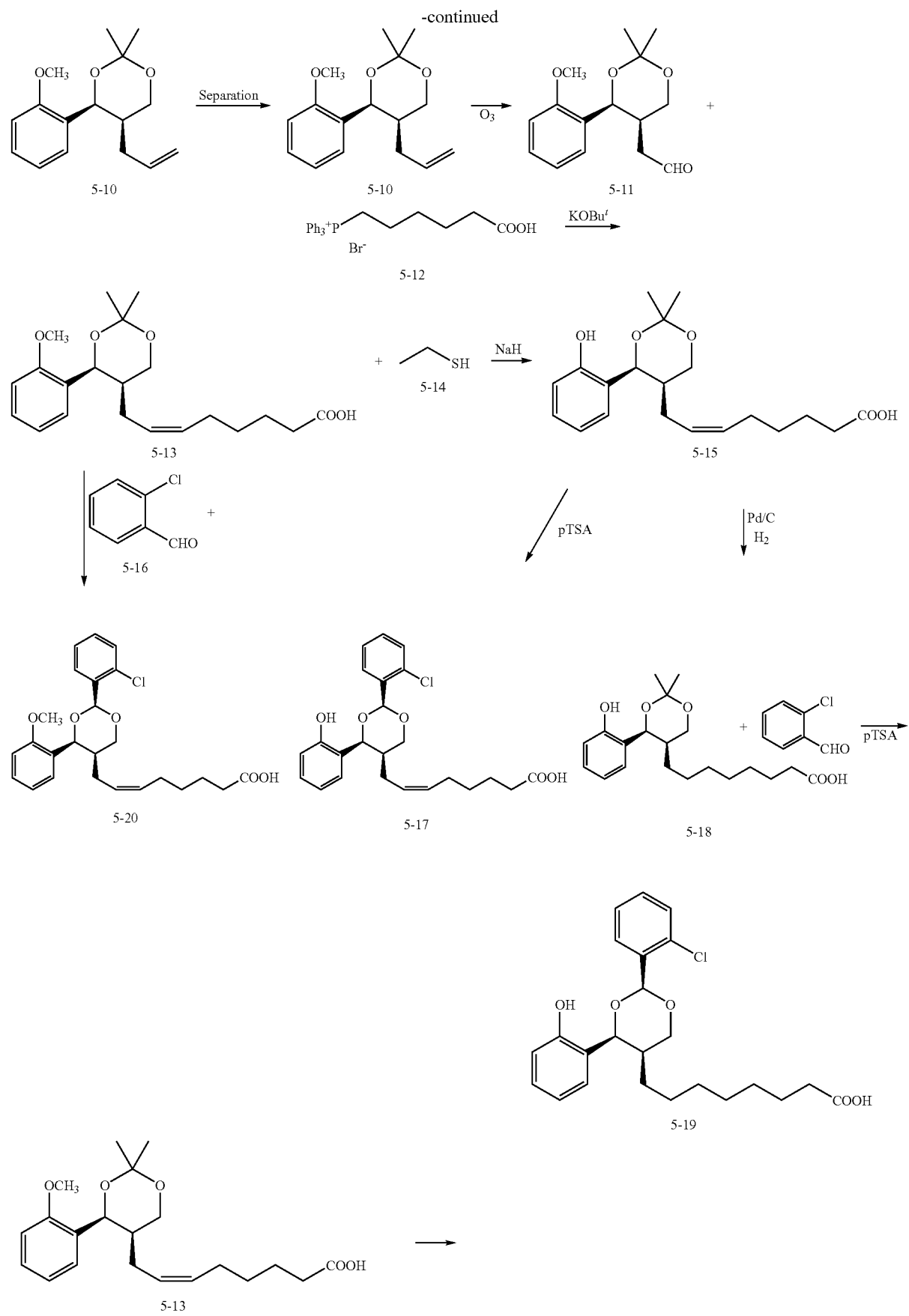

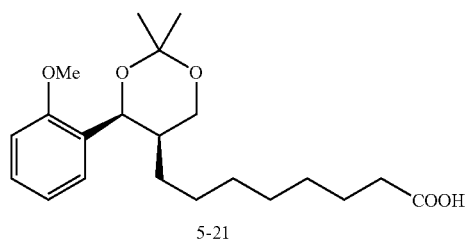

5-21

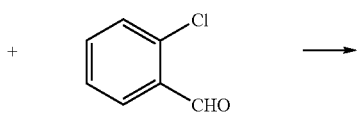

5-16

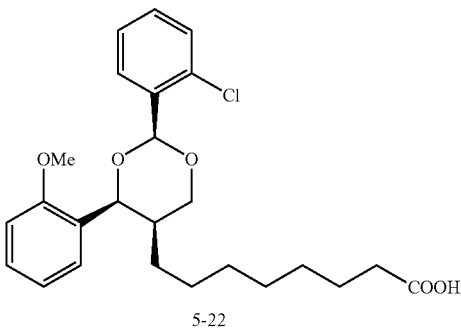

5-22

Example 15:

Synthesis of PPAR Modulator 37 (SN37, Table II)

This example describes the synthesis of PPAR modulator 37 of Table II according to Scheme 5.

Preparation of Ethyl Hydrogenmalonate 5-2 in Scheme 5

To a stirred solution of diethyl malonate (20 g, 0.125 moles) in ethanol (100 mL) at r.t, a solution of 85% KOH (7 g, 0.125 moles) in ethanol (30 mL) was added with occasional cooling. After 20 min, the mixture was acidified with conc. HCl and filtered. The filter cake (KCl) was washed with ethanol (50 mL). The combined filtrate was concentrated and residual liquid was subjected to column chromatography (hexane-EtOAc: 85:15) to afford 1 (14.7 g, 87%).

$^1$HNMR (CDCl$_3$): 1.22 (3H, t), 3.39 (2H, s), 4.39-4.41 (2H, q).

Preparation of Keto-ester 5-4

To a suspension of 14.34 g of magnesium ethoxide (0.13 moles) in dry THF (100 mL) was added 10.5 g of ethyl hydrogenmalonate 15-2 (0.08 moles) and refluxed for 90 min. The reaction mixture was cooled to 0° C. and a solution of 2-methoxybenzoyl chloride 5-3 (14.59 g; 0.085 moles) in dry THF (25 mL) was added at such a rate that the reaction temperature did not exceed 5° C. The reaction mixture was stirred at r.t for overnight and allowed to stand for two days. A saturated solution of ammonium chloride was added and the reaction mixture was extracted with EtOAc (3×50 mL). The combined organic layer was washed with water and dried over anhydrous sodium sulphate. The solvent was evaporated to give the product as oil and was purified by column chromatography (hexane-EtOAc: 95:5) to yield the product (4.33 g, 25% yield). The product was confirmed by spectral data.

$^1$HNMR (CDCl$_3$): 1.23 (3H, t), 3.85 (5H, s), 4.10-4.22 (2H, q), 6.90-7.05 (2H, m), 7.42-7.51 (1H, m), 7.69-7.80 (1H, d).

To a stirred suspension of sodium hydride (60%, 0.9 g, 0.08 moles) in dry THF (40 mL), the acetylated ester (4.33 g, 0.019 moles) was added drop wise at 0-10 C and stirred for 15 min. Ally bromide 5-5 (2.30 g, 0.019 moles) was added to the reaction mixture at the r.t. and the reaction mixture was refluxed for 3-4-h. The reaction mixture was cooled and ammonium chloride solution was added and extracted with EtOAc (3×30 mL). The organic layer was washed with water, dried over anhydrous sodium sulphate and evaporated. The crude product was purified by column chromatography (n-hexane-EtOAc: 95:5) to obtain 5-6 (2.5 g. 50% yield).

$^1$H-NMR (CDCl$_3$): 1.15 (3H, t), 2.61-2.72 (2H, m), 3.90 (3H, s), 4.05-4.11 (2H, q), 4.30-4.33 (1H, m), 4.92-5.10 (2H, m), 5.78-5.81 (1H, m), 6.92-7.15 (2H, m), 7.40-7.49 (1H, m), 7.71-7.75 (1H, d).

Preparation of Diol (5-7)

To the cooled suspension of lithium borohydride (0.83 g, 0.038 moles) in dry THF (15 mL) was added the cooled solution of alkylated keto ester 5-6 (2.5 g, 0.0095 moles) in dry THF (25 mL) at such a rate that the temperature did not exceed 10° C. Stirring was continued for 4-5 h at r.t. and the progress of the reaction was monitored by TLC. The reaction mixture was acidified to pH 2 by the addition of 2N HCl; water was added to the reaction mixture and extracted with EtOAc (3×25 mL). The combined organic layer was washed with brine, water and dried over anhydrous sodium sulphate. The solvent was evaporated to yield the cis and trans reaction mixture of the diol 5-7 (2 g, 94% yield) and proceeded to the next step with out purification. HPLC: c is 77.318%, retention time 20.244 min.; trans 22.682%, retention time 22.337 min. (HPLC conditions are mentioned on the chromatogram).

Preparation of the Acetonide 5-10

A solution of diol 5-7 (2 g, 0.009 moles), 2,2-dimethylpropane (15 mL, 0.12 moles), catalytic amount pTSA (10 mg) was stirred at r.t. for 4-5 h and the progress of the reaction was monitored by TLC. The reaction mixture was neutralized with Et$_3$N. Excess DMP was removed under vacuum and the oily cis-trans mixture was separated by column chromatography to get 5-10 (0.925 g, yield 40%).

¹HNMR (CDCl₃): 1.51 (3H, s), 1.53 (3H, s), 1.62-1.80 (2H, m), 2.25-2.41(1H, m), 3.75-3.85 (1H, m), 3.82 (3H, s), 4.08-4.11 (1H, m), 4.85-4.96 (2H, m), 5.35 (1H, d, J=2.3), 5.41-5.62 (1H, m), 6.75-6.81 (1H, d), 6.90-6.97 (1H, m), 7.15-7.25 (1H, m), 7.33-7.41(1H, m).

Preparation 1,3-dioxane Aldehyde (Ozonolysis) 5-11

$O_3$ was passed through a solution of acetonide 5-10 (0.93 g, 0.004 moles) in dry DCM (10 mL) at −78° C. till the permanent blue colour was developed. The reaction mixture was stirred at 0° C. till the blue colour was disappeared. A solution of TPP (1.1 g, 0.0043 moles) in DCM (5 mL) was added to the colourless solution at 0° C. and the reaction mixture was warmed to room temperature and stir for 1 h. The progress of the reaction mixture was monitored by TLC. The solvent was removed and the product was purified by flash chromatography to yield the aldehyde 5-11 (0.5 g, yield 54%).

¹HNMR (CDCl₃): δ 1.50 (3H, s), 1.54 (3H, s), 2.23 (1H, dd), 2.44 (1H, m), 2.75-2.80 (1H, m), 3.65 (1H, dd), 3.81 (3H, s), 4.21-4.22 (1H, dd), 5.39 (1H, d, J=2.2 Hz), 6.90 (1H, d), 6.95-6.97 (1H, t), 7.18-7.21 (1H, m), 7.39-7.40 (1H, d), 9.45 (1H, s).

IR (cm⁻¹): 2992, 2933, 2720, 1723, 1595, 1491, 1462, 1379, 1239 and 1197.

Preparation of Wittig Salt 5-12

A solution of 6-Bromohexanoic acid (3 g, 0.0512 moles) and triphenylphosphine 4.8 g, 0.018 moles) in dry acetonitrile (50 mL) was refluxed for 20-24 h and excess solvent was removed under reduced pressure to afford a color less oil which was triturated with dry benzene and wash in succession with dry benzene and ether (3 times each). During the washing procedure the material crystallized drying at reduced pressure afford Wittig salt as a white microcrystalline powder (3.6 g, 55% yield).

Preparation of 2,4-substituted (1,3-dioxane-5-yl) Carboxylic Acid (SN37, Table II)] (Wittig Product) 5-13

A solution of sodium hydride (60%, 0.364 g, 0.0152 moles) in dry THF (5 mL) was added to a stirred suspension of Wittig salt 5-12 (0.95 g, 0.002 moles) in dry THF (10 mL) at 0° C. under $N_2$ atmosphere. The mixture was stirred for 30 min. Then a solution of aldehyde 5-11 (0.5 g, 0.0019 moles) was added. The reaction was kept under stirring for 36 h. After the completion of reaction, water was added and the solvent was removed under reduced pressure. The aqueous solution was washed with ethyl acetate and acidified to pH 2 with 5% HCL and extracted with ethyl acetate. The combined organic extract was washed with saturated brine, dried over anhydrous $Na_2SO_4$ and evaporated. The oil obtained was purified by flash column chromatography (Hexane:Ethyl acetate −75:25) to afford the Wittig product 5-13 (0.2 g, 35% yield).

¹HNMR (CDCl₃): δ 1.49 (3H, s), 1.51 (3H, s), 1.40-1.49 (4H, m), 1.55-1.95 (4H, m), 2.22-2.48 (3H, m), 3.70-3.75 (1H, m), 3.80 (3H, s), 4.05-4.15 (1H, m), 5.12-5.42 (2H, m), 5.35 (1H, d, J=2.30 Hz), 6.75-6.80 (1H, d), 6.92-6.99 (1H, t), 7.21-7.25 (1H, m), 7.40-7.47 (1H, d).

LC/MS: Purity 91% and MW: 385 (M+Na).

Example 16:

Synthesis of PPAR Modulator 36 (SN36, Table II)

This example describes the synthesis of PPAR modulator 36 of Table II (2,2-dimethyl-4-(2-hydroxyphenyl)-1,3-dioxane-5-yl-carboxylic acid) (5-15) (deprotection of methoxy group):

Ethanethiol (0.13 g, 0.00203 moles) was added at 0° C. under $N_2$ atmosphere to a stirred suspension of sodium hydride (60%, 1 g, 0.004167 moles) in DMPU (5 mL). After 30 min a solution of compound 5-13 (0.00055 moles) in DMPU was added. The mixture was heated at 120° C. for 2-3 h, cooled, poured into ice water and the aqueous mixture was washed with DCM. The aqueous layer was acidified to pH 5 with 5% HCl and extracted with ethyl acetate. The combined organic extract was washed with saturated brine dried and evaporated. The oil obtained was purified by flash column chromatography (Hexane:Ethyl acetate −75:25) to afford Wittig product 5-15 (0.6 g, 66% yield).

¹HNMR (CDCl₃): 1.51 (3H, s), 1.53 (3H, s), 1.22-1.34 (4H, m), 1.52-2.00 (4H, m), 2.21-2.34 (2H, t), 2.53-2.69 (1H, m), 3.79-4.11 (2H, m), 5.15-5.40 (2H, m), 5.38-5.40 (1H, d, J=2.40), 6.70-6.95 (3H, m), 7.05-7.15 (1H, m), 8.20-8.30 (1H, br). LC/MS: Purity 99% and MW: 371 (M+Na).

Example 17:

Synthesis of PPAR Modulator 35 (SN35, Table II)

This example describes the synthesis of PPAR modulator 35 of Table II (Z)-8-(2-(2-Chlorophenyl)-4-(2-methoxyphenyl)-1,3-dioxan-5-yl)octa-6-enoic acid (5-20 scheme 5):

A mixture of 2-chlorobenzaldehyde (50.48 mg, 0.359 mmoles), pTSA (catalytic, 5 mg) and acetonide compound 5-15 (130 mg, 0.359 mmoles) was stirred in 4 mL of dry toluene for 24 h. The solvent was evaporated under reduced pressure and mixture was subjected to column chromatography (hexane-EtOAc: 80:20) to afford product 5-20 (55 mg, 34.3% yield).

¹HNMR (CDCl₃, δ): 1.21-2.03 (8H, m); 2.25 (2H, t, J=7.554 Hz); 2.28 (1H, m); 3.83 (3H, s); 4.16 (2H, m); 5.13-5.38 (2H, m); 5.41 (1H, d, J=2.266 Hz); 6.03 (1H, s); 6.81 (1H, d, J=7.554 Hz); 6.93 (1H, t, J=7.55 Hz); 7.14-7.36 (4H, m); 7.43 (1H, t, J=6.043 Hz); 7.82 (1H, d, J=7.554 Hz). LC-MS: Purity 89.19% (71.05+18.14, two diastereomers) and MW 462 (M+18).

Example 18:

Synthesis of PPAR Modulator 38 (SN38, Table II)

This example describes the synthesis of PPAR modulator 38 of Table II 8-(2-(2-Chlorophenyl)-4-(2-methoxyphenyl)-1,3-dioxan-5-yl)octanoic acid (5-21):

To the solution of olefin compound 5-13 (150 mg, 0.414 mmol) in 5 mL of dry ethyl acetate, 10 mol % of 10% Pd—C (44 mg) was added carefully. The reaction mixture was allowed to stir under $H_2$ atmosphere for 1.5-2 h. After reaction was completed the mixture was filtered through celite and cake (Pd—C) was washed with dry ethyl acetate (2×5 mL). The combined filtrate was concentrated and residual liquid was subjected to column chromatography (hexane-EtOAc: 80:20) to afford product 5-21 (SN38) (80 mg, 53.05% yield).

$^1$HNMR (CDCl$_3$, δ): 1.06-1.60 (12H, m); 1.46 (3H, s); 1.53 (3H, s); 1.67 (1H, m); 2.25 (2H, t, J=7.554 Hz); 3.76 (1H, d, J=10.009 Hz); 3.81 (3H, s); 4.15 (1H, d, J=8.687 Hz); 5.32 (1H, d, J=2.455 Hz); 6.77 (1H, d, J=7.365 Hz); 6.92 (1H, t, J=7.554 Hz); 7.16 (1H, t, J=6.043 Hz); 7.38 (1H, d, J=5.854 Hz).

A mixture of 2-chlorobenzaldehyde (34.25 mg, 0.247 mmoles), pTSA (catalytic, 3 mg) and acetonide compound 125-21 (80 mg, 0.34 mmoles) was stirred in 3 mL of dry toluene for 24 h. The solvent was evaporated under reduced pressure and mixture was subjected to column chromatography (hexane-EtOAc: 80:20) to afford product 5-22 (50 mg, 45% yield).

$^1$HNMR (CDCl$_3$, δ): 1.08-1.92 (13H, m); 2.26 (2H, t, J=7.554 Hz); 3.83 (3H, s); 4.20 (2H, m); 5.36 (1H, d, J=2.266 Hz); 6.02 (1H, s); 6.81 (1H, d, J=7.554 Hz); 6.92 (1H, t, J=7.554 Hz); 7.15-7.36 (4H, m); 7.42 (1H, t, J=7.554 Hz); 7.81 (1H, d, J=7.554 Hz).

LC-MS: Purity 87.53% and MW 464 (M+18).

Example 19:

Synthesis of PPAR Modulator 24 (SN24, Table II)

This example describes the synthesis of PPAR modulator 24 of Table II f(Z)-8-(2-(2-Chlorophenyl)-4-(2-methoxyphenyl)-1,3-dioxan-5-yl)octa-6-enoic acid (5-17).

A mixture of 2-chlorobanzaldehyde (48.47 mg, 0.344 mmoles), pTSA (catalytic, 5 mg) and acetonide compound (120 mg, 0.344 mmoles) was stirred in 4 mL of dry toluene for 24 h.

The solvent was evaporated under reduced pressure and mixture was subjected to column chromatography (hexane-EtOAc: 80:20) to afford product 5-17 (40 mg, 27% yield).

$^1$HNMR (CDCl$_3$, δ): 1.13-2.80 (11H, m); 4.10-4.37 (2H, m); 5.17-5.41 (2H, m); 5.44 (1H, d, J=2.340 Hz); 6.00 (1H, s); 6.74-7.74 (8H, m).

LC-MS: Purity is 94.43% (two diastereomers, 80.12+14.31 respectively) and MW 448 (M+18).

Example 20:

Synthesis of PPAR Modulator 31 (SN31, Table II)

This example describes the synthesis of PPAR modulator 31 of Table II 8-(2-(2-Chlorophenyl)-4-(2-hydroxyphenyl)-1,3-dioxan-5-yl)octanoic acid (5-19)

To the solution of olefin 5-15 (60 mg, 0.172 mmole) in 3 mL of dry ethyl acetate, 10 mol % (19 mg, 0.0172 mmole) of 10% Pd—C was added. The reaction mixture was allowed to stir under H$_2$ atmosphere for 8 h. After reaction was completed the mixture was filtered through celite and cake (Pd—C) was washed with dry ethyl acetate (2×5 mL). The combined filtrates were concentrated and residual liquid was subjected to column chromatography (hexane-EtOAc: 80:20) to afford product 5-18 (40 mg, 66% yield).

$^1$HNMR (CDCl$_3$, δ): 1.05-1.88 (13H, m); 1.54 (3H, s); 1.58 (3H, s); 2.29 (2H, t, J=7.031 Hz); 3.86 (1H, d, J=11.719 Hz); 4.15 (1H, d, J=12.5 Hz); 5.36 (1H, d, J=2.344 Hz); 6.82 (3H, m); 7.12 (1H, m); 8.32 (1H, broad).

A mixture of 2-chlorobanzaldehyde (16 mg, 0.114 mmoles), pTSA (catalytic, 3 mg) and acetonide compound 5-18 (40 mg, 0.114 mmoles) was stirred in 3 mL of dry toluene for 24 h.

The solvent was evaporated under reduced pressure and mixture was subjected to column chromatography (hexane-EtOAc: 80:20) to afford product 5-19 (20 mg, 40% yield).

$^1$HNMR (CDCl$_3$, δ): 1.07-2.35 (13H, m); 2.98 (2H, t, J=7.554 Hz); 3.65-4.41 (2H, m); 4.62 (1H, d, J=10.575 Hz); 5.90 (1H, s); 6.77-7.66 (8H, m).

LC-MS: Purity 85% and MW 450 (M+18).

Scheme 6

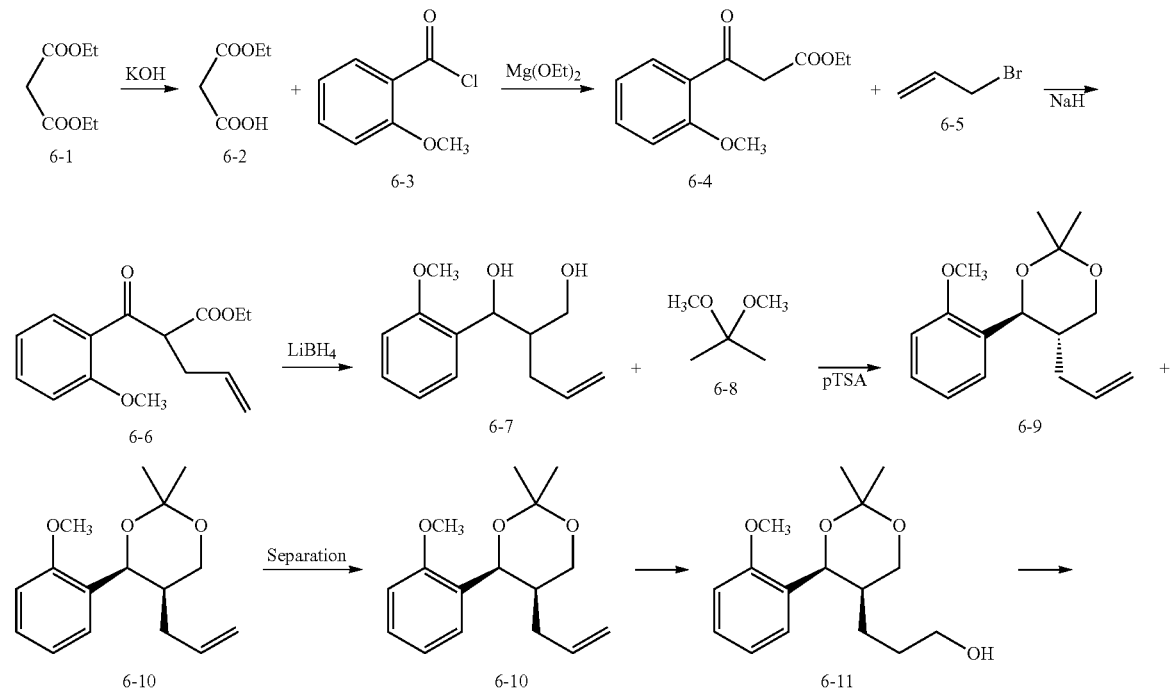

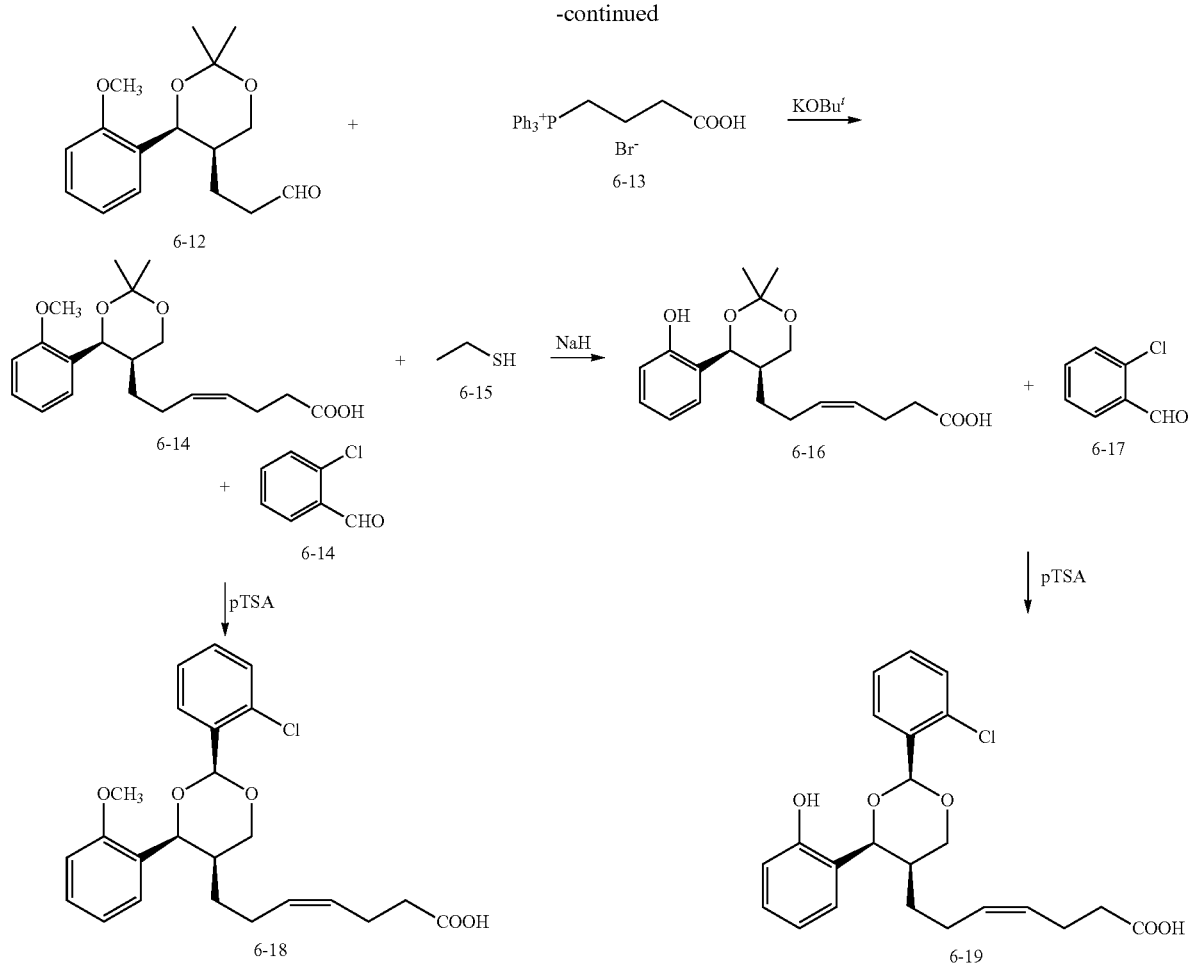

Example 21:

Synthesis of PPAR Modulator 32 (SN32, Table II)

This example describes the synthesis of PPAR modulator 32 of Table II

To a solution of alkene 6-10 (described earlier 5-10) (1.2 g, 4.5 mmol) in dry THF (10 mL) was added $BH_3.DMS$ (0.34 g, 4.5) at 0° C. and the reaction mixture was stirred for 2 h at the same temperature. To this mixture was added, 3N NaOH (3 mL) and 30% $H_2O_2$ (1 mL) at 0° C. and stirring continued for another hour at room temperature. The reaction mixture was diluted with water and extracted with ethyl acetate (2×30 mL). The combined organic layers were evaporated under vacuum and the crude product was purified by column chromatography (ethyl acetate:hexanes; 2:8).

Yield: 0.9 g (70%)

$^1$H NMR ($CDCl_3$, 200 MHz): δ 7.51-7.45 (d, J=6.4 Hz, 1H), 7.3-7.2 (t, J=7.1 Hz, 1H), 7.05-6.95 (t, J=7.1 Hz, 1H), 6.9-6.82 (d, J=7.1 Hz, 1H), 5.5-5.4 (s 1H), 4.25-4.19 (d, J=9.6 Hz, 1H), 3.92-3.78 (m, 4H), 3.53-3.40 (t, J=7.1 Hz, 2H), 1.85-1.70 (m, 1H), 1.51 (d, J=11.3 Hz, 6H), 1.32-1.0 (m, 4H).

Preparation of 6-12: IBX (0.525 g, 1.87 mmol) was dissolved in dry DMSO (1 mL) and stirred for 10 min at RT and cooled to 0° C. To this, alcohol 6 (0.35 g, 1.25 mmol) was added in dry THF (9 mL) under nitrogen atmosphere and stirred for 1.5 h at room temperature. The reaction mixture was diluted with ether (10 mL), stirred for 20 min and filtered. The filtrate was washed with water (2×10 mL), the ether layer was dried ($Na_2SO_4$) and concentrated on rotary evaporator. The product was purified by filter column to obtain aldehyde 6-12 (ethyl acetate:hexanes; 2:8).

Yield: 300 mg (86.4% yield).

$^1$H NMR ($CDCl_3$, 200 MHz): δ 9.59 (s, 1H), 7.54-7.48 (d, J=6.4 Hz, 1H), 7.28-7.20 (t, J=6.4 Hz, 1H), 7.08-6.95 (t, J=6.4 Hz, 1H), 6.90-6.82 (d, J=6.4 Hz, 1H), 5.42 (s, 1H), 4.26-4.21 (d, J=9.6 Hz, 1H), 3.81 (s, 3H), 3.80-3.75 (d, J=9.6 Hz, 1H), 2.4-1.7 (m, 3H), 1.51 (s, 6H), 1.45-1.40 (m, 2H).

Preparation of 6-14: (3-Carboxypropyl)triphenylphosphonium bromide was dried under vacuum at 100° C. for 2-3 h. To a stirred solution of (3-Carboxypropyl)triphenylphosphonium bromide (1.47 g, 3.43 mmol) in dry Toluene (10 mL), Potassium t-butoxide (0.774 g, 6.89 mmol) was added in portions at room temperature under inert conditions. The mixture was heated to 80° C. and temperature was maintained for 30-40 min. Reaction mass was cooled to 50° C. and the aldehyde (compound 6-12) (0.3 g, 1.07 mmol) in dry THF (2 mL) was added to above mixture drop wise. The progress of the reaction was monitored by TLC. After the completion of reaction, the mass was cooled to 0-5° C. and quenched with 1N HCl (1 mL) by adjusting the pH 4-5. The compound was extracted with ethyl acetate (3×10 mL) and separated the aqueous layer. The combined organic fractions were collected and dried over sodium sulphate (2 g), concentrated in vacuo. The crude product was purified by column chromatography to obtain compound 6-14 pure (ethyl acetate:hexanes; 2:8).

Yield: 325 mg (86%).

$^1$H NMR (CDCl$_3$, 300 MHz): δ 7.45-7.4 (d, J=7.1 Hz, 1H), 7.25-7.10 (t, J=7.1, 1H), 6.95-6.85 (t, J=7.1 Hz, 1H), 6.80-6.70 (d, J=7.1 Hz, 1H), 5.40-5.30 (s, 1H), 5.25-5.10 (m, 2H), 4.2-4.1 (d, J=14.3 Hz, 1H), 3.85-3.8 (d, J=14.3 Hz, 1H), 3.75 (s, 3H), 2.35-2.05 (m, 4H), 1.75-1.5 (m, 3H), 1.50-1.45 (d, J=11.4 Hz, 6H), 0.85-0.75 (m, 2H).

MW:371.1 (M$^+$+Na).

Preparation of 6-16: Ethanethiol (0.44 g, 7.17 mmol) was added to a stirred suspension of 60% NaH (0.287 g, 7.17 mmol) in dry DMF (10 mL) at 0-5° C. and stirred for 20-30 min. Compound 6-14 (0.25 g, 0.71 mmol) in dry DMF (2 mL) was added slowly drop wise to the above mixture maintaining the temperature. The reaction mass temperature was raised to 120-130° C. and maintained for 6-8 h. After the completion of reaction, the mass was cooled to 0-5° C. and quenched with 1N HCl (1 mL) by adjusting the pH 4-5. The compound was extracted with ethyl acetate (3×10 mL) and separated the aqueous layer. The combined organic fractions were collected, washed with brine water dried over sodium sulphate (2 g), concentrated under vacuum. The crude product was purified by column chromatography to obtain 6-16 pure (ethyl acetate:hexanes; 2.5:7.5).

Yield: 155 mg (65%).

Compound 6-16 (130 mg, 0.38 mmol) was dissolved in THF (8 mL), and a catalytic amount of pTsOH was added at room temperature. The reaction mixture was kept for stirring at room temperature for 6-8 h. o-Chlorobenzaldehyde (109 mg, 0.77 mmol) was added to the reaction mass; once again catalytic amount of pTsOH was added. Reaction conditions were maintained for further 5-6 h. After the completion of reaction dry Et$_3$N was added by adjusting the pH=7. The solvent was removed under vacuum and the resulting crude mixture was purified by column chromatography to obtain final product SN32 (Table II) 6-19. (Ethyl acetate: hexanes; 3.5:6.5).

Yield: 65 mg (40%).

The HPLC purity after column chromatography is 80.3% with closer impurities. This was further purified by preparative HPLC to obtain 92.4% HPLC pure compound (20 mg obtained).

$^1$H NMR (CDCl$_3$, 200 MHz): δ 7.7-7.6 (d, J=6.4 Hz, 1H), 7.35-7.20 (m, 3H), 7.10-7.0 (s, 1H), 6.99-6.90 (d, J=6.4 Hz, 1H), 6.80-6.60 (m, 2H), 5.95 (s, 1H), 5.85-5.80 (s, 1H), 5.25-5.10 (brs, 2H), 4.27-4.05 (dd, J=6.4, 9.6 Hz, 2H), 2.4-2.1 (m, 4H), 2.0-1.65 (m, 3H), 1.29-1.1 (m, 2H).

MW: 415.1 (M$^+$—H)

HPLC purity: 92%. A further analog was synthesized as follows: Compound 6-14 (90 mg, 0.25 mmol) was dissolved in a mixture of THF: 0.2N HCl (10 mL, 9:1) and stirred for 2 h at room temperature. After completion of the reaction, the mixture was extracted with ethyl acetate (2×10 mL), dried over Na$_2$SO$_4$ and evaporated on rotary evaporator to obtain 68 mg of crude product, which was utilized for further reaction without purification.

The above crude compound (68 mg, 0.22 mmol) was dissolved in dry THF to this mixture was added 2-chlorobenzaldehyde (61 mg, 0.44 mmol) and catalytic amount of pTSA (~4 mg) at room temperature. The reaction mixture was stirred for 5 h at same temperature under nitrogen atmosphere. After disappearance of the starting material, the mixture was neutralized with dry triethylamine (by adjusting the pH to 7) and the solvent was evaporated. The crude product was purified by column chromatography (25% ethyl acetate in hexanes) to obtain the compound 6-18.

Yield: 32 mg (34%).

$^1$H NMR (CDCl$_3$, 300 MHz): δ 7.9-7.8 (d, J=7.1 Hz, 1H), 7.45-7.15 (m, 5H), 6.95-6.87 (t, J=7.0 Hz, 1H), 6.85-6.77 (d, J=7.2 Hz, 1H), 6.05 (s, 1H), 5.36 (s, 1H), 5.25 (brs, 2H), 4.2 (2, 2H), 3.85 (s, 3H), 2.35-2.1 (m, 4H), 2.05-1.82 (m, 3H), 1.3-1.1 (m, 2H).

MW: 429.1 (M$^+$—H)

HPLC purity: 98%.

Example 22:

PPARgamma Transactivation Assays

Cell Culture, Plasmids and Transfections

This is an example of a transactivation assay for determining PPAR gamma modulating activity.

Gal4-PPARgammaLBD (Helledie et al 2000), UASx-4-TK luc (Chen and Evans, 1995) and CMV-beta-galactosidase (available commercially, e.g. Clontech) were used in these assays to show PPAR gamma transactivation. The UASx-4-TK-luc reporter construct (where UAS refers to "upstream activator sequence") contains four Gal4-responsive elements. The plasmid Gal4-PPARgammaLBD encodes a Gal4-DBD-PPARgamma-LBD fusion protein (i.e. the DNA-binding domain, DBD, of Gal4 fused to the ligand-binding domain, LBD, of PPARgamma) capable of transactivating the UASx-4-TK-luc reporter plasmid by binding to the UAS. The CMV-beta-galactosidase plasmid (where CMV is cytomegalovirus) is used for normalization of experimental values.

Mouse embryonic fibroblasts (MEFs) were grown in AmnioMax basal medium (Gibco) supplemented with 7.5% Amniomax supplement C-100 (Gibco), 7.5% Fetal Bovine Serum (FBS), 2 mM Glutamine, 62.5 µg/ml penicillin and 100 µg/ml Streptomycin (growth medium). Alternatively, ME3 cells (Hansen et al., 1999) were grown in DMEM supplemented with 10% Calf Serum (CS), 62.5 µg/ml penicillin and 100 µg/ml Streptomycin (growth medium). The cells were replated, typically in 24 well plates, so that at the time of transfection the cells are 50-70% confluent.

The cells were transfected with Gal4-PPARgammaLBD (Helledie et al 2000), UASx-4-TK luc (Chen and Evans, 1995) and CMV-beta-galactosidase (available commercially, e.g. Clontech) using Lipofectamin Plus (Invitrogen) or Metaffectane (Biontex) according to the manufacturer's instructions. Briefly, per well in a 24 well plate, UASx4TKluc (0.2 µg) Gal4-PPARgammaLBD (or pM-hPPARgamma-LBD; 0.1 µg) and CMV-beta-galactosidase (0.05 µg) in 30 µL DMEM (free of serum and antibiotics) is mixed with 30 µL DMEM (free of serum and antibiotics) containing 1 µL metafectenein. The mixture is incubated at room temperature for 20 min to allow formation of nucleic acid-lipid complexes and then approximately 60 µL is added to each well containing the 50-60% confluent cells. The cells are then incubated at 37° C. in a CO$_2$ incubator for 6 to 12 hours and then the medium is replaced with medium supplemented with antibiotics and the substance of interest (e.g., 4-(Z)-6-(2-o-chlorophenyl-4-o-hydroxyphenyl-1,3-dioxan-cis-5-yl) hexenoic acid, referred to herein as DPD, or rosiglitazone (Avandia) as a positive control, all dissolved in DMSO) or a comparable volume of DMSO (<0.5% of total cell culture volume). DPD is available commercially or can be synthesized according to Example 1. Cells were harvested after 12-24 hours and luciferase and beta-galactosidase activities were measured according to standard protocols.

Figure 2:
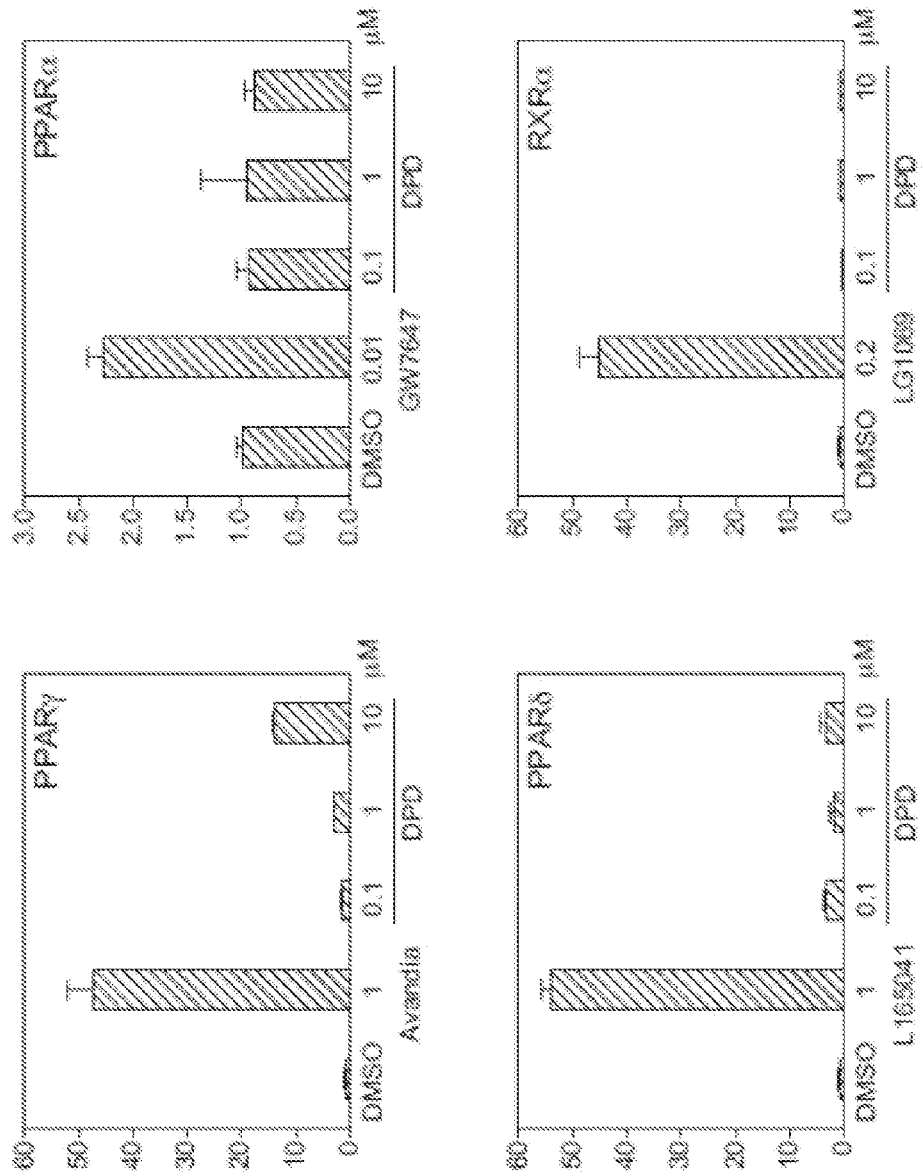
FIG. 2 illustrates selective activation of PPAR-gamma by rosiglitazone and (Z)-6-(-2-(2-chlorophenyl)-4-(2-hydroxyphenyl)-1,3-dioxan-5-yl)hex-4-enoic acid, compared with PPAR-delta, PPAR-alpha and RxR.

PPAR transactivation was over 40-fold higher with rosiglitazone (a known PPAR gamma agonist) than with DMSO alone, and about 10-fold higher with 10 µM 4-(Z)-6-(2-O—chlorophenyl-4-o-hydroxyphenyl-1,3-dioxan-cis-5-yl) hexenoic acid (see "DPD" in FIG. 2). Thus 4-(Z)-6-(2-o-chlorophenyl-4-o-hydroxyphenyl-1,3-dioxan-cis-5-yl) hexenoic acid is a PPARgamma agonist.

Preliminary results indicated that there was no difference in PPARgamma transactivating activity between either of the DPD enantiomers purified by chiral HPLC. However, subsequent analysis has revealed a significant difference (see Example 32 herein below). Thus one enantiomer was found not to bind PPARγ, whereas the other binds PPARγ with an $IC_{50}$ of in the range of 4.9 to 12 µM.

Table II summarizes the results obtained with various analogs of DPD (SN1) and compares their activities. "P" represents a similar PPARgamma activating activity at 10 µM compared with 10 µM DPD (SN1 in Table II), "P–" represents same level of activity at 30 µM tested substance compared with 10 µM DPD (ie less potent); "P+" represents level of activity greater than "P" and a level of activity at 3 µM comparable with 10 µM DPD (ie more potent); "P++" represents a level of activity at 3 µM above that of 10 µM DPD but at 1 µM below that of 10 µM DPD; and "P+++" represents a level of activity at 1 µM comparable with 10 µM DPD. "–" means that testing was not performed.

Figure 3:
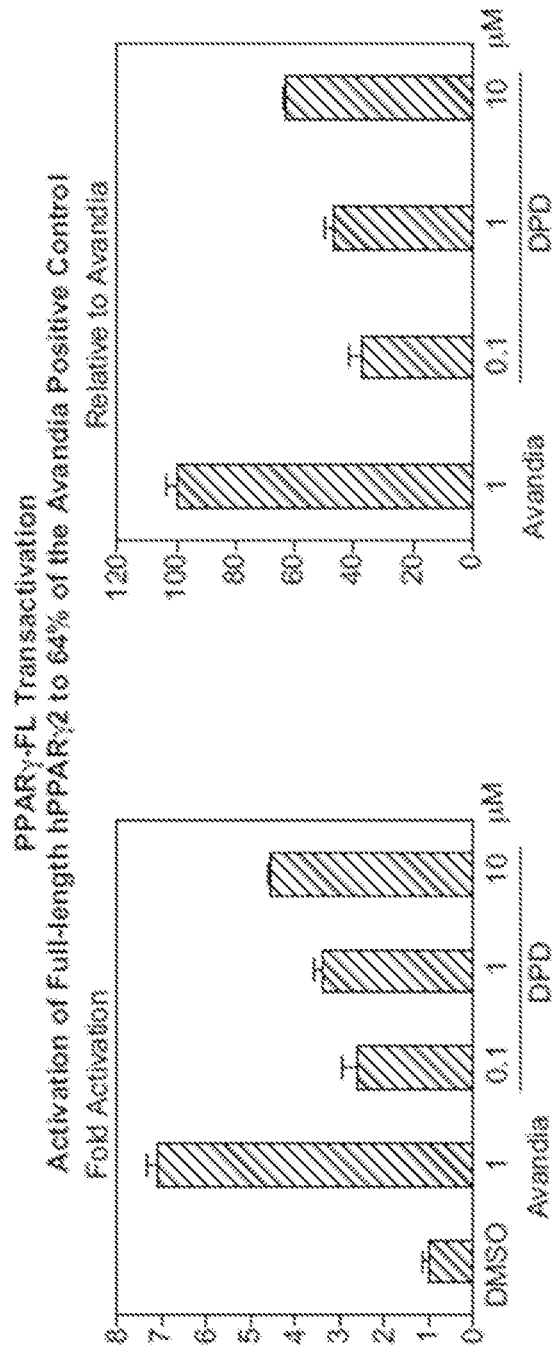
FIG. 3 illustrates activation of full length PPAR-gamma by rosiglitazone and (Z)-6-(-2-(2-chlorophenyl)-4-(2-hydroxyphenyl)-1,3-dioxan-5-yl(hex-4-enoic acid FIG. 4 illustrates that (Z)-6-(2-(2-chlorophenyl)-4-(2-hydroxyphenyl-1,3-dioxan-cis-5-yl)hex-4-enoic acid has no effect on full length PPAR-delta transactivation.

When this assay was carried out essentially as described above but with the full length human PPARgamma rather than with the PPARgamma ligand binding domain, activation of full-length hPPARg2 was seen to 64% of the Avandia positive control (FIG. 3).

Example 23:

PPARdelta Transactivation Assays

This example describes a transactivation assay for determining PPARdelta modulating activity.

DPD and other ligands are tested for their ability to transactivate PPARdelta essentially as described in Example 22. However, the transactivating construct is mPPARdeltaLBD, where the PPARdelta ligand binding domain replaces that of PPARgamma and L165041 (commercially available) is used as a selective PPARdelta agonist instead of rosiglitazone. Under the conditions used, L165041 was shown to increase PPARdelta transactivation by over 50-fold, whereas DPD resulted in no or little increase in transactivation (see FIG. 2). Therefore DPD shows selectivity for PPARgamma.

Figure 4:
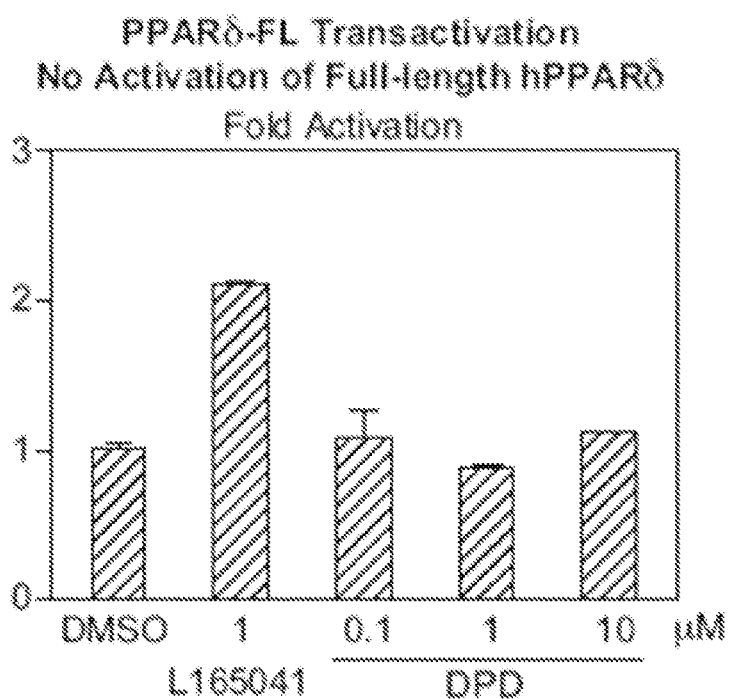

When this assay was carried out essentially as described above but with the full length human PPARdelta rather than with the PPARdelta ligand binding domain, activation of full-length hPPARdelta, no activation was seen (FIG. 4), confirming the selectivity of DPD for PPARgamma.

Example 24:

PPARalpha Transactivation Assays

This example describes a transactivation assay for determining PPARalpha modulating activity.

DPD and other ligands are tested for their ability to transactivate PPARalpha essentially as described in Example 22. However, the transactivating construct is mPPARalphaLBD, where the PPARalpha ligand binding domain replaces that of PPARgamma and GW7647 (commercially available) is used as a selective PPARalpha agonist instead of rosiglitazone. Under the conditions used, GW7647 was shown to increase PPARalpha transactivation by over 2-fold, whereas DPD resulted in no transactivation (see FIG. 2). Therefore DPD shows selectivity for PPARgamma.

Example 25:

RXR Transactivation Assays

This example describes a retinoic acid X receptor transactivation assay.

Compounds are tested for their ability to transactivate RXR essentially as described in Example 22. However, the transactivating construct was hRXRαLBD, where the RXR ligand binding domain replaces that of PPARgamma and {4-[1-(3,5,5,8,8-pentamethyl-5,6,7,8-tetrahydro-2-naphthyl)ethenyl] benzoic acid} (LG1069, commercially available) is used as a selective RXR agonist instead of rosiglitazone. Under the conditions used, LG1069 is shown to increase RXR transactivation by over 5-fold, whereas DPD resulted in no transactivation (see FIG. 2). Therefore DPD again shows selectivity for PPARgamma.

Example 26:

Adipocyte Differentiation Assays

This example describes an assay for determining adipocyte differention. Compounds are tested to see whether they induce adipocyte differentiation and also to see whether they inhibit adipocyte differention.

Cell Culture and Differentiation

MEFs were grown in AmnioMax basal medium (Gibco) supplemented with 7.5% Amniomax supplement C-100 (Gibco), 7.5% Fetal Bovine Serum (FBS), 2 mM Glutamine, 62.5 µg/ml penicillin and 100 µg/ml Streptomycin (growth medium). At confluence, MEFs were induced to differentiation in growth medium with the addition of 1 µM dexamethasone (Sigma) 0.5 mM isobutylmethylxanthine (Sigma), 5 µg/ml insulin (Sigma) and 10 µM test compound dissolved in DMSO or DMSO alone. Medium was subsequently renewed every 48 hrs with growth media supplemented with 5 µg/ml Insulin and ligand or DMSO.

Briefly, to test compounds as inducers of adipocyte differentiation, 3T3-L1 are grown to confluence in DMEM with 10% Calf serum (CS), typically in 24 well dishes. At 2 days post confluence (day 0), cells are induced to differentiate with DMEM supplemented with 10% fetal bovine serum (FBS), 1 µM dexamethasone and the test compound (01, 1 and 10 µM). BRL49653 (1.0 µM dissolved in 100% DMSO) is used as a positive control. After 48 h, the cells are re-fed with DMEM containing 10% FBS supplemented with the test compound or the positive control. From day 4, cells are grown in DMEM with 10% FBS and are changed every second day until day 8. At day 8, cells are stained with Oil Red O as described below.

To test compounds as inhibitors of adipocyte differentiation, 3T3-L1 cells are grown as above until two-day postconfluence (designated day 0), after which the cells are induced to differentiate with DMEM containing 10% fetal bovine serum (FBS), 1 µM dexamethasone (Sigma), 0.5 mM methylisobutylxanthine (Sigma), 1 µg/ml insulin (Roche Molecular Biochemicals) and the test-compound. Cells induced to differentiate in presence of solvent of the test-compounds are used as positive control. After 48 h, the cells are re-fed with DMEM containing 10% FBS supplemented with the test compound or the positive control. From day 4, cells are grown in DMEM with 10% FBS and are changed every second day until day 8. At day 8, cells are stained with Oil Red O as described below.

Oil Red O Staining

Cells cultured as described above are used for Oil Red staining. Dishes are washed in PBS and cells were fixed in 3.7% paraformaldehyde for 1 h and stained with oil red O as described in (Hansen et al 1999). Oil red O solution stock solution is prepared by dissolving 0.5 g of Oil Red O (Sigma) in 100 mL of isopropanol. Oil re 0 working solution is prepared by diluting a stock solution with water (6:4) followed by filtration.

DPD induced very little red staining in the induction assay. As the red staining is indicative of the presence of adipocytes, it can be inferred that DPD does not induces adipocyte differentiation. However, DPD does not inhibit adipocyte as it showed no significant effect in inhibition of adipocyte differentiation. Table II summarizes results obtained with different analogs of DPD (SN1), "0" representing similar results to DPD, "−1" representing even less adipocyte differentiation, "+1" representing more adipocyte differentiation (both relative to DPD) and "−" meaning not assayed.

An assay carried out essentially as described above but using human pre-adipocytes also demonstrated that DPD induced very little red staining, similar to DMSO.

Example 27:

Identification of Partial Agonists vs. Full Agonists

This example describes an assay for determining partial PPAR agonists, which are particularly desirable as pharmaceuticals.

Figure 5:
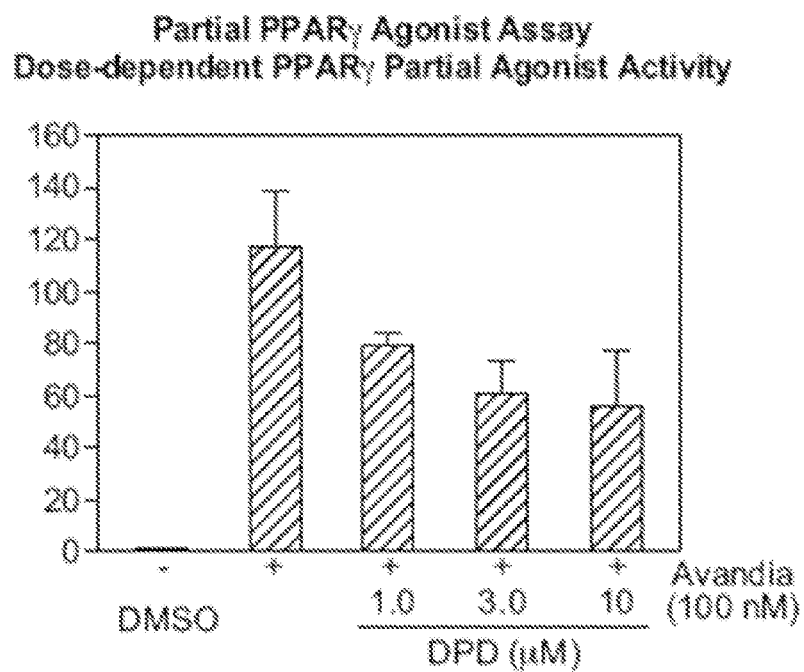
FIG. 5 illustrates results of partial PPAR-gamma competition assays.

Briefly, transactivation assays are carried out essentially as described in Example 22 but 100 nM Avandia (a full agonist) is added to each well, together with increasing concentrations of test compound (or no test compound as control). Compounds that reduce the transactivation by Avandia are PPAR partial agonists. The results are depicted in FIG. 5.

PPARgamma partial agonists are identified in this example by their ability to displace a known PPARgamma agonist from binding to PPARgamma, e.g., Avandina in this case. Alternatively, other known full agonists can be used, for example 300 nM L165041 to identify partial agonists of PPARdelta using the transactivation assay essentially as described in Example 2.

Example 28:

Partial PPARgamma Agonist Ligand Displacement Assay

A further assay to identify partial PPARgamma agonists is performed using the Invitrogen POLARSCREEN PPAR competition assay, as follows for the analysis of binding to the PPARgamma ligand-binding pocket.
1. Dispense 20 microL 2× test compound in the cuvette
2. Add 20 microliter 2×PPAR-LBD/Fluormone Green Complex and mix
3. Incubate in the dark for 2 hours
4. Measure fluorescence polarization value
5. As control, use rosiglitazone (Avandia)

Figure 6:
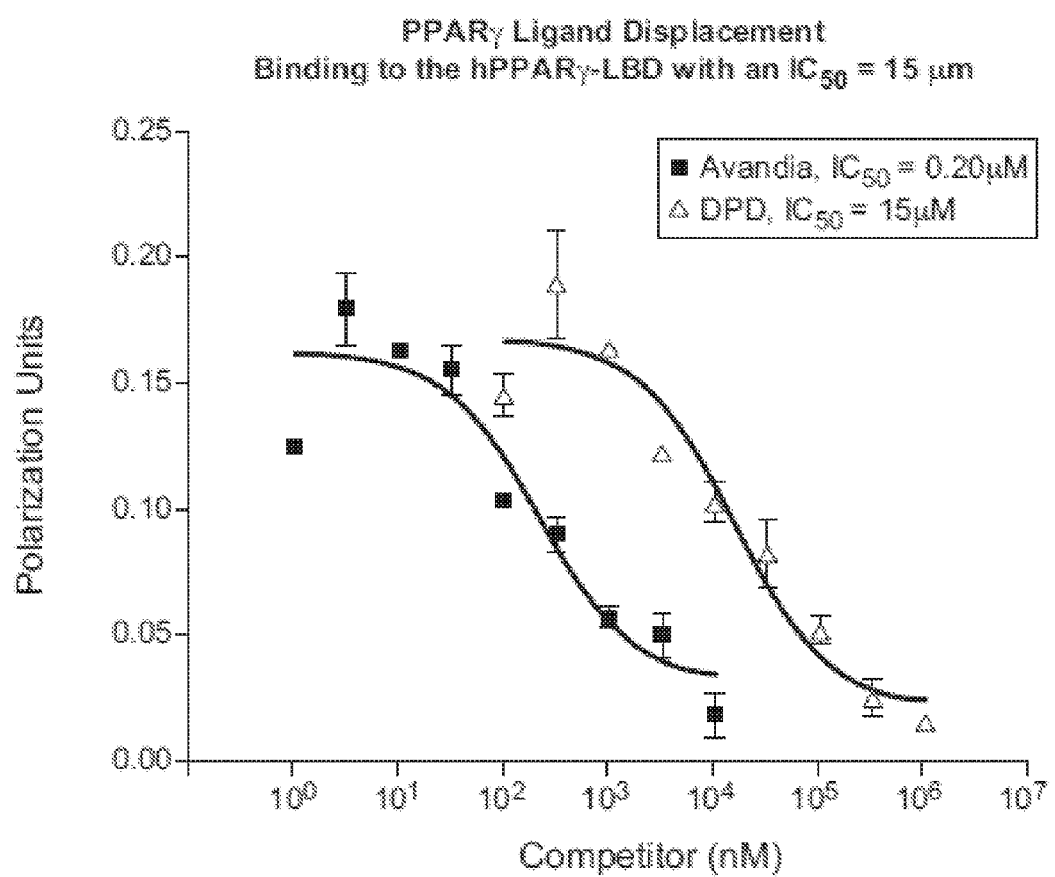
FIG. 6 illustrates results of PPAR-gamma ligand displacement assays.

The results with DPD relative to AVANDIA are shown in FIG. 6.

Example 29:

Glucose Uptake Assays

This example illustrates that compounds identified as PPARgamma agonists also produce a physiological effect in cellular assays, expected of a PPARgamma agonist, namely an effect on glucose uptake. Glucose uptake assays are important to establish the suitability of a compound for the treatment of insulin resistance.

Figure 7:
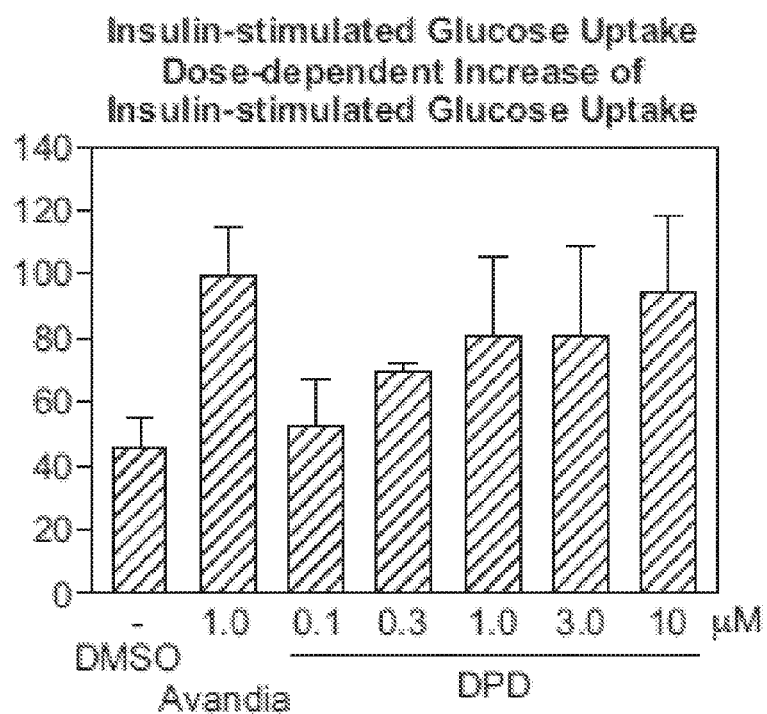
FIG. 7 illustrates results of glucose uptake assays.
Figure 8:
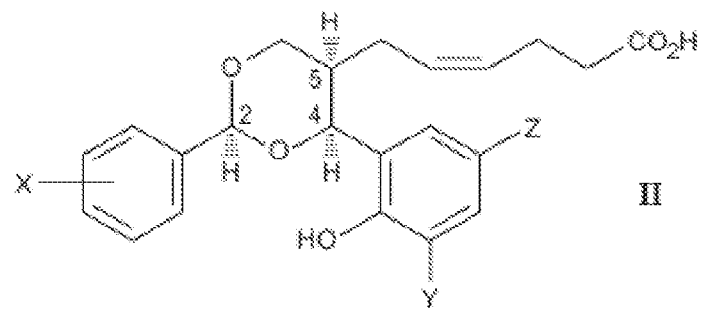
FIG. 8 illustrates chemical formulae II-V.
Figure 8:
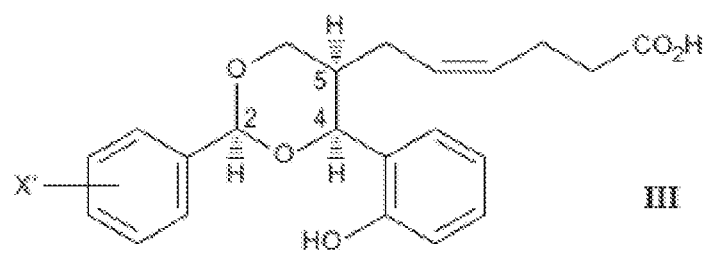
Figure 8:
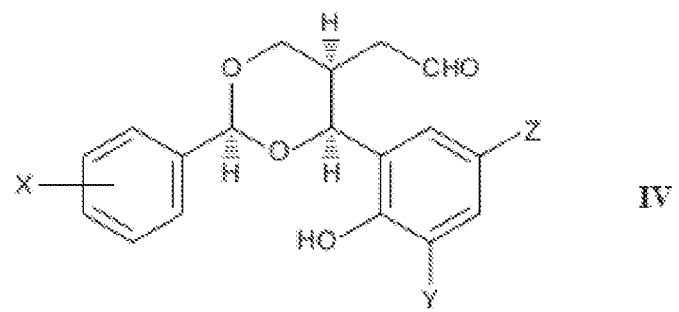
Figure 8:
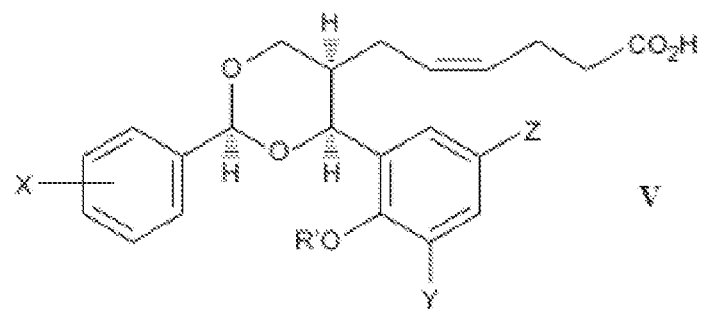
Figure 9:
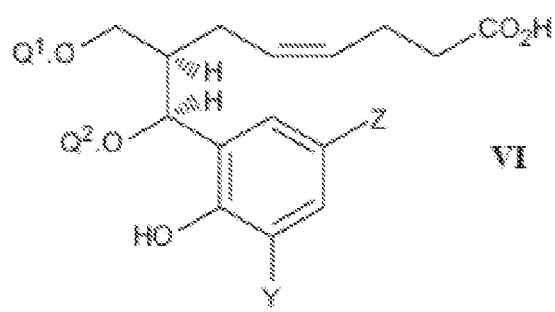
FIG. 9 illustrates chemical formulae VI-VIII.
Figure 9:
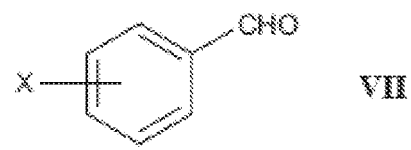
Figure 9:
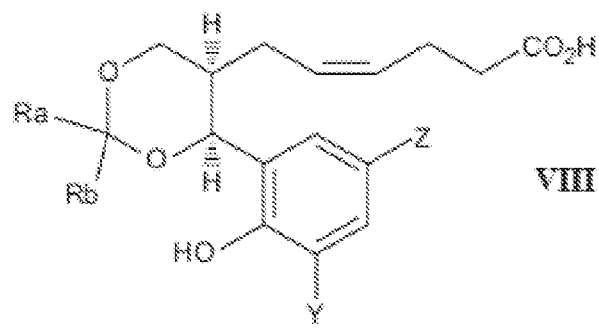
Figure 10:
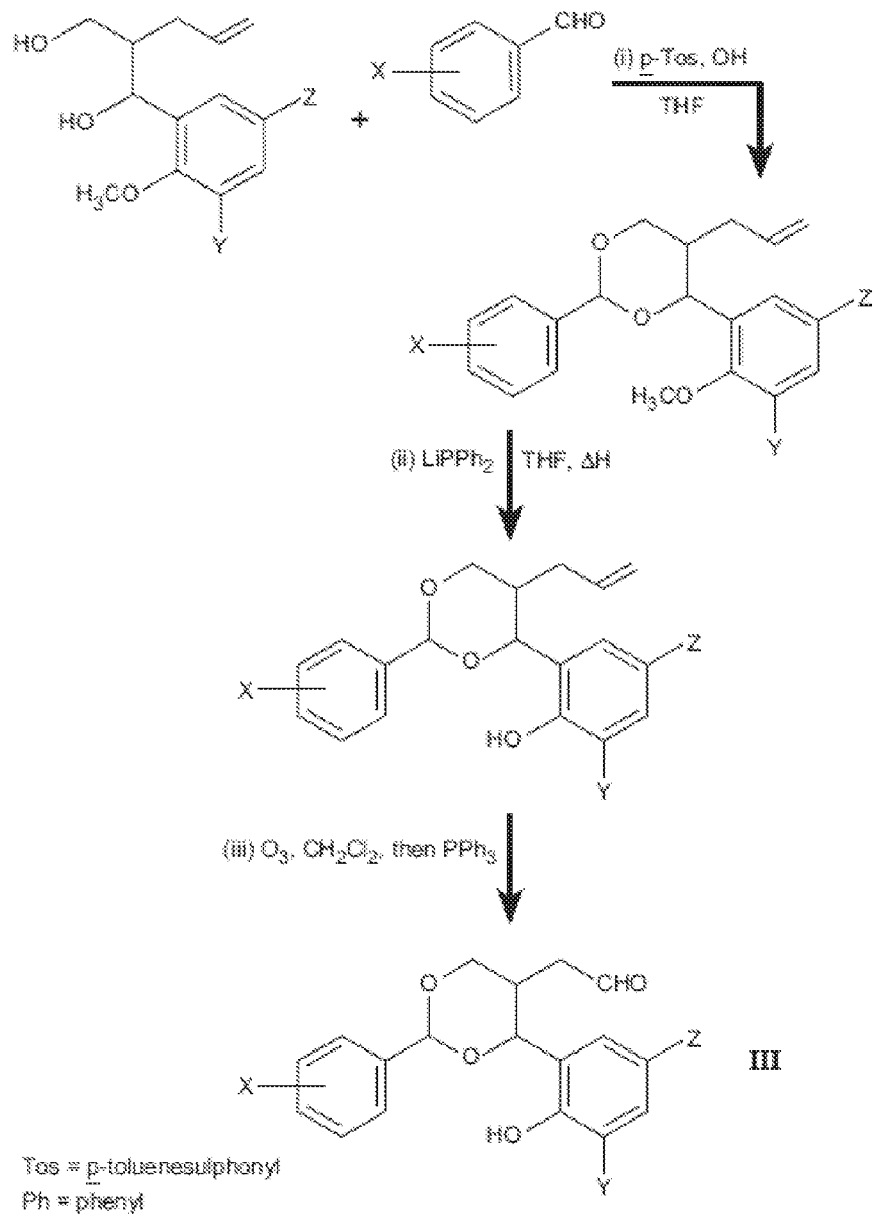
FIG. 10 illustrates chemical Reaction Scheme I.

Briefly, 3T3-L1 preadipocytes are grown in 12-well plates until confluence. Cells are washed with serum-free DMEM and incubated with 1 ml of the same medium at 37° C. for 1-2 h. The cells are then washed with Krebs-Ringer-Hepes (KRP) buffer and then incubated with 0.9 ml KRP buffer at 37° C. for 30 min. Insulin is added to the cells at 0, 0.3, 1 and 3 nM final concentrations and incubated for 15 min at 37° C. Glucose uptake is initiated by the addition of 0.1 ml of Krebs-Ringer phosphate (KRP) buffer supplemented with 10 mM [$^3$H] 2-deoxy-D-glucose (1 mCi/l). After 10 min incubation at 37° C., the medium is aspirated and plates washed with ice-cold PBS to terminate the induced glucose uptake. The cells are lyzed with 0.5 ml 1% Triton X-100 and radioactivity levels determined using a scintillation counter. The results are depicted in FIG. 7.

In summary, DPD and a number of analogs referred to in Table II are demonstrated to be PPARgamma agonists, whereas substance 10 appeared to be a PPARgamma antagonist. Substances 7 and 13 are particularly interesting analogs as these show higher potency whilst causing low or no adipocyte differentiation.

TABLE II

| SN | Structure | PPAR | Adip. |
|----|-----------|------|-------|
| 1 | ![structure] | P | 0 |
| 2 | ![structure] | P | 0 |

TABLE II-continued

| SN | Structure | PPAR | Adip. |
|---|---|---|---|
| 3 | 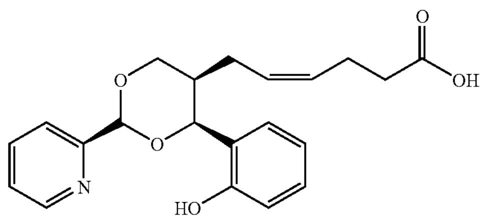 | — | — |
| 4 | 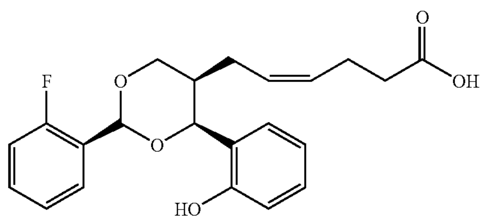 | P+ | 0 |
| 5 | 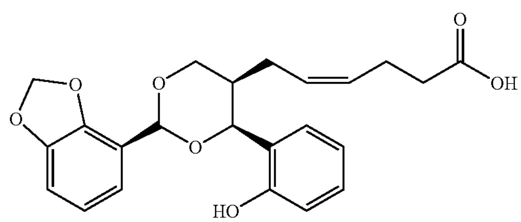 | P− | 0 |
| 6 | 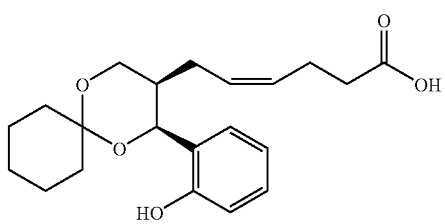 [SMILES: O=C(O)CC/C=C\C[C@@H]1COC2(CCCCC2)O[C@@H]1c1ccccc1O] | P | 0 |
| 7 | 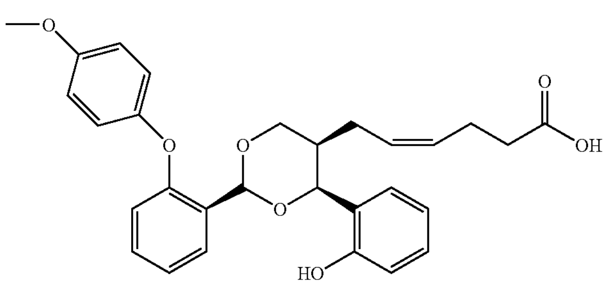 | P+++ | 0 |
| 8 | 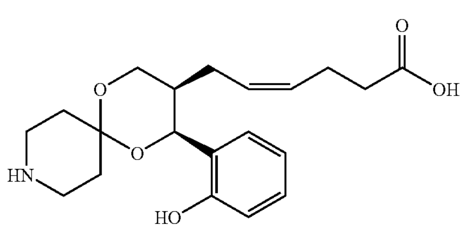 [SMILES: O=C(O)CC/C=C\C[C@@H]1COC2(CCNCC2)O[C@@H]1c1ccccc1O] | Boc derivative Inactive | −1 |

TABLE II-continued

| SN | Structure | PPAR | Adip. |
|---|---|---|---|
| 9 | 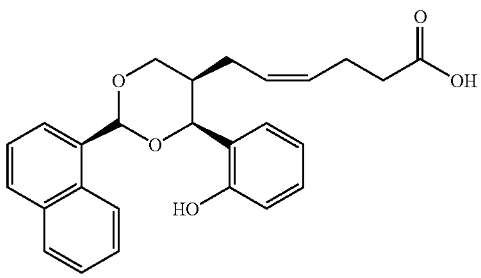 | P | 0 |
| 10 | 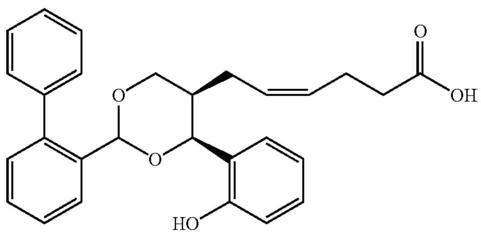 [SMILES: O=C(O)CC/C=C\C[C@@H]1COC(c2ccccc2-c2ccccc2)O[C@@H]1c1ccccc1O] | Antagonist | 0 |
| 11 | 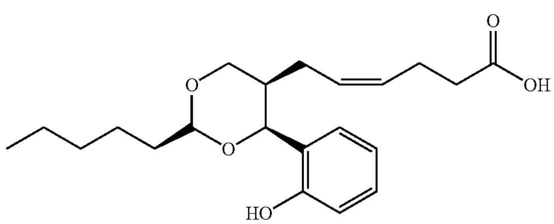 | P+ | +1 |
| 12 | 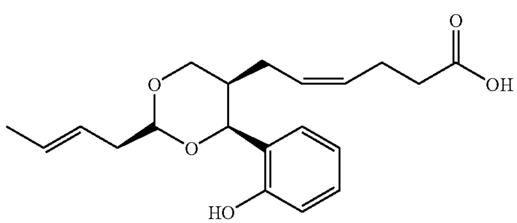 | P | −1 |
| 13 | 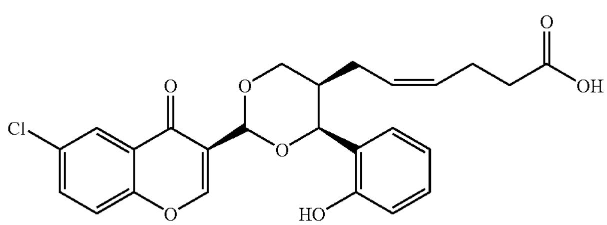 | P+++ | −1 |
| 14 | 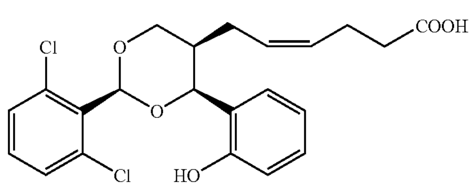 [SMILES: O=C(O)CC/C=C\C[C@@H]1CO[C@H](c2c(Cl)cccc2Cl)O[C@@H]1c1ccccc1O] | | |
| 15 | 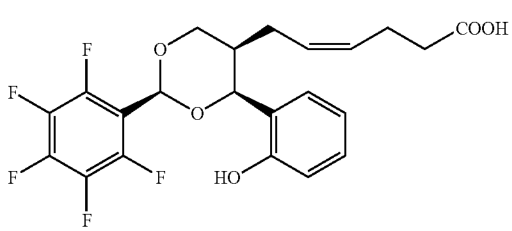 [SMILES: O=C(O)CC/C=C\C[C@@H]1CO[C@H](c2c(F)c(F)c(F)c(F)c2F)O[C@@H]1c1ccccc1O] | | |

TABLE II-continued

| SN | Structure | PPAR | Adip. |
|---|---|---|---|
| 16 | 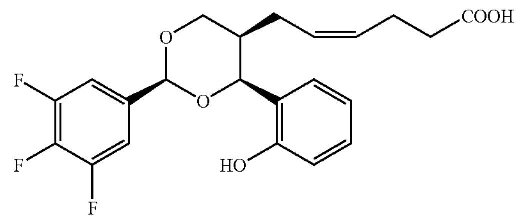 [SMILES: O=C(O)CC/C=C\C[C@@H]1CO[C@H](c2cc(F)c(F)c(F)c2)O[C@@H]1c1ccccc1O] | | |
| 17 | 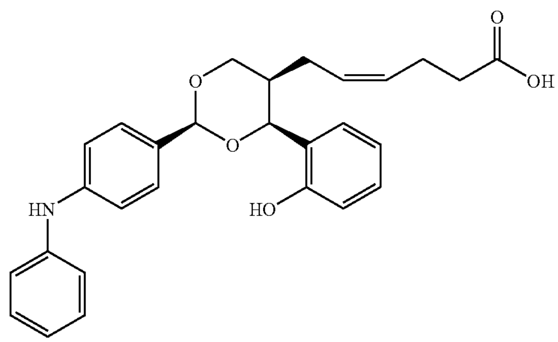 [SMILES: O=C(O)CC/C=C\C[C@@H]1CO[C@H](c2ccc(Nc3ccccc3)cc2)O[C@@H]1c1ccccc1O] | | |
| 18 | 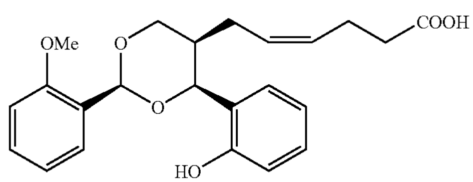 [SMILES: COc1ccccc1[C@H]1OC[C@@H](C/C=C\CCC(=O)O)[C@@H](c2ccccc2O)O1] | P | −1 |
| 19 | 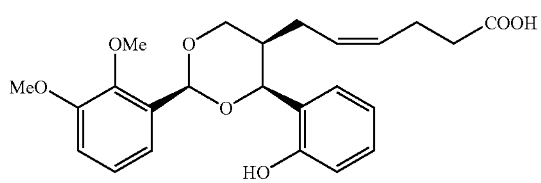 [SMILES: COc1cccc([C@H]2OC[C@@H](C/C=C\CCC(=O)O)[C@@H](c3ccccc3O)O2)c1OC] | P | 0 |
| 20 | 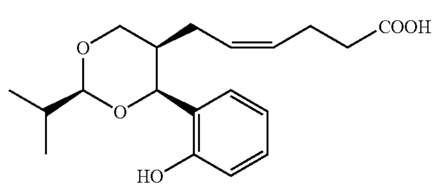 [SMILES: CC(C)[C@H]1OC[C@@H](C/C=C\CCC(=O)O)[C@@H](c2ccccc2O)O1] | P | 0 |
| 21 | 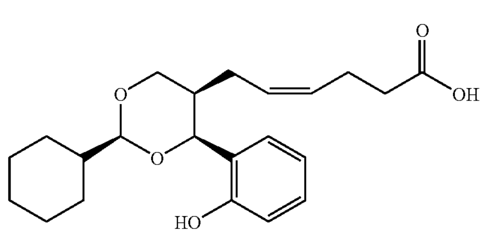 [SMILES: O=C(O)CC/C=C\C[C@@H]1CO[C@H](C2CCCCC2)O[C@@H]1c1ccccc1O] | P+ | 0 |

TABLE II-continued

| SN | Structure | PPAR | Adip. |
|---|---|---|---|
| 22 | 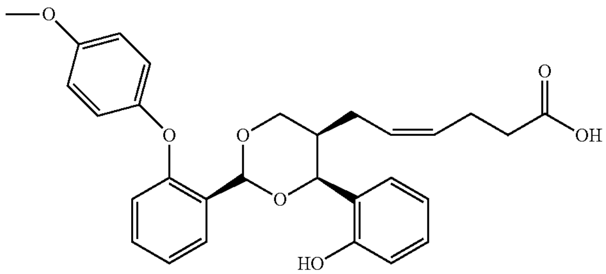 | | |
| 23 | 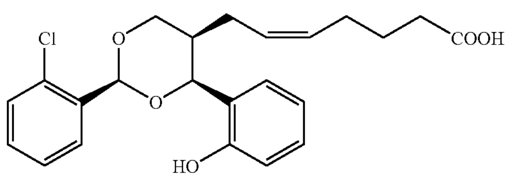 [SMILES: O=C(O)CCC/C=C\C[C@@H]1CO[C@H](c2ccccc2Cl)O[C@@H]1c1ccccc1O] | P+ | +1 |
| 24 | 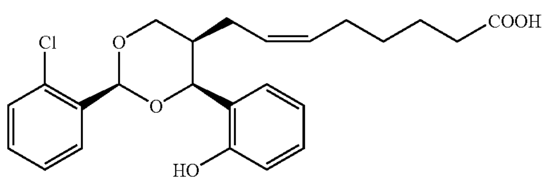 [SMILES: O=C(O)CCCC/C=C\C[C@@H]1CO[C@H](c2ccccc2Cl)O[C@@H]1c1ccccc1O] | P+ | — |
| 25 | 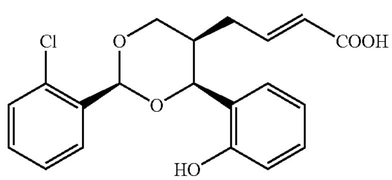 [SMILES: O=C(O)/C=C/C[C@@H]1CO[C@H](c2ccccc2Cl)O[C@@H]1c1ccccc1O] | — | — |
| 26 | 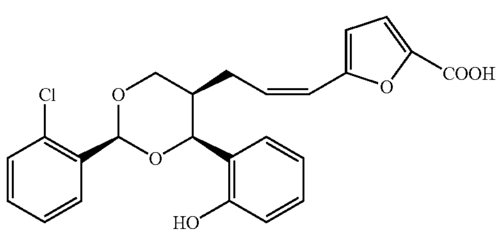 [SMILES: O=C(O)c1ccc(/C=C\C[C@@H]2CO[C@H](c3ccccc3Cl)O[C@@H]2c2ccccc2O)o1] | | |
| 27 | 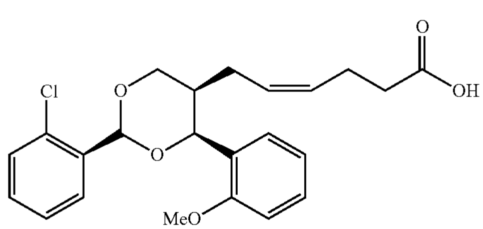 | Inactive | — |
| 28 | 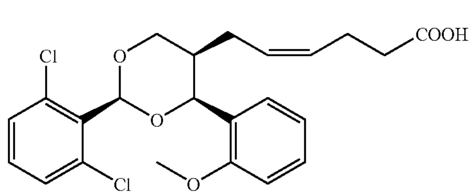 [SMILES: COc1ccccc1[C@H]1O[C@@H](c2c(Cl)cccc2Cl)OC[C@H]1C/C=C\CCC(=O)O] | Inactive | — |

TABLE II-continued

| SN | Structure | PPAR | Adip. |
|---|---|---|---|
| 29 | 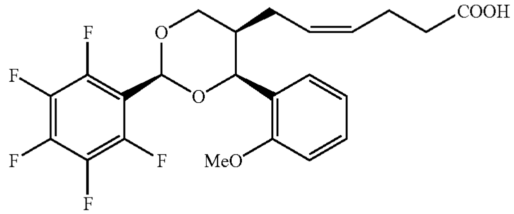 | P | — |
| 30 | 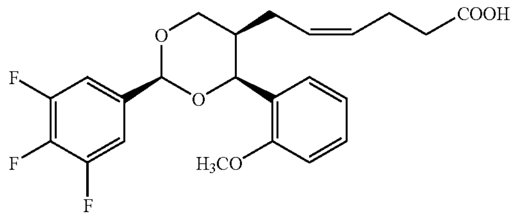 [SMILES: COc1ccccc1[C@H]1O[C@@H](c2cc(F)c(F)c(F)c2)OC[C@H]1C/C=C\CCC(=O)O] | P | — |
| 31 | 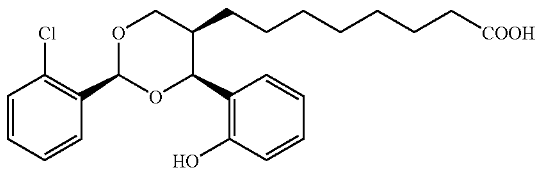 [SMILES: O=C(O)CCCCCCC[C@@H]1CO[C@H](c2ccccc2Cl)O[C@@H]1c1ccccc1O] | P+ | 0 |
| 32 | 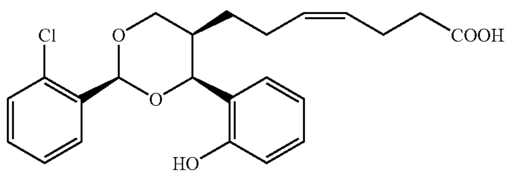 [SMILES: O=C(O)CC/C=C\CC[C@@H]1CO[C@H](c2ccccc2Cl)O[C@@H]1c1ccccc1O] | P++ | — |
| 33 | 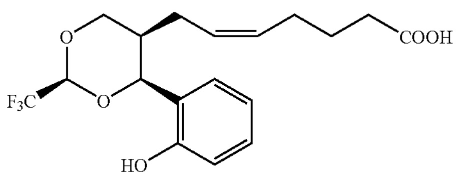 | P | — |
| 34 | 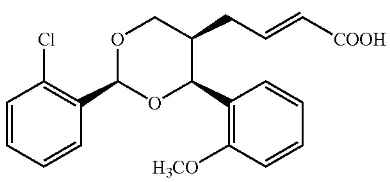 [SMILES: COc1ccccc1[C@H]1O[C@@H](c2ccccc2Cl)OC[C@H]1C/C=C/C(=O)O] | P | — |
| 35 | 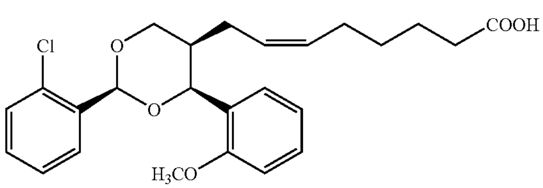 [SMILES: COc1ccccc1[C@H]1O[C@@H](c2ccccc2Cl)OC[C@H]1C/C=C\CCCCC(=O)O] | P | — |
| 36 | 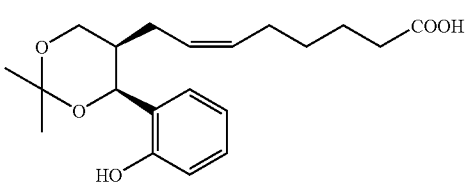 [SMILES: CC1(C)OC[C@@H](C/C=C\CCCCC(=O)O)[C@@H](c2ccccc2O)O1] | Inactive | — |

TABLE II-continued

| SN | Structure | PPAR | Adip. |
|---|---|---|---|
| 37 | 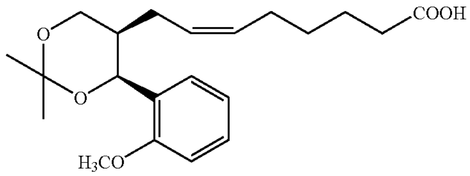 [SMILES: COc1ccccc1[C@H]1OC(C)(C)OC[C@H]1C/C=C\CCCCC(=O)O] | Inactive | 0 |
| 38 | 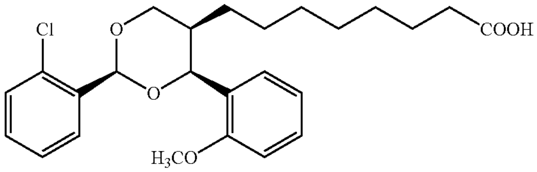 [SMILES: COc1ccccc1[C@H]1O[C@@H](c2ccccc2Cl)OC[C@H]1CCCCCCCC(=O)O] | P+ | — |
| 39 | 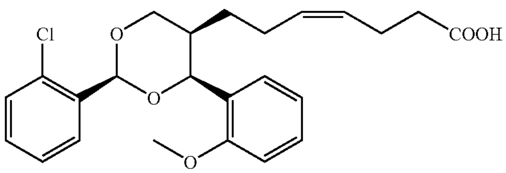 [SMILES: COc1ccccc1[C@H]1O[C@@H](c2ccccc2Cl)OC[C@H]1CC/C=C\CCC(=O)O] | — | — |

Example 30:

Thromboxane Receptor activity

This example demonstrates that only one enantiomer of substance 1 (SN1) binds to the TP receptor.

Each enantiomer of DPD (SN1 in Table II), i.e. the compounds (Z)-6-((2S,4S,5R)-2-(2-chlorophenyl)-4-(2-hydroxyphenyl)-1,3-dioxan-5-yl(hex-4-enoic acid (enantiomer 1) and (Z)-6-((2R,4R,5S)-2-(2-chlorophenyl)-4-(2-hydroxyphenyl)-1,3-d ioxan-5-yl)hex-4-enoic acid (enantiomer 2, as per elution on chiral column below), was isolated by chiral chromatography under the following conditions:

Column: 250×4.6 mm Chiralpak AD-H 5 µm
  Mobile phase: 80/20/0.1 n-Heptane/Ethanol/Trifluoroacetic acid
  Flow rate: 1 ml/min
  Detection: UV at 230 nm
  Temperature: 25° C.
  Samples were dissolved in 80/20 n-Heptane/Ethanol
  Enantiomer 1 elutes first on the chiral column and Enantiomer 2 eluted second on the chiral column.

The enantiomers 1 and 2 were tested on radioligand binding assays for thromboxane receptor binding essentially as described by Hedberg et al. (1988) J. Pharmacol. Exp. Ther. 245:786-792 and Saussy et al. (1986) J. Biol. Chem. 261: 3025-3029. Whereas Enantiomer ((Z)-6-((2S,4S,5R)-2-(2-chlorophenyl)-4-(2-hydroxyphenyl)-1,3-dioxan-5-yl(hex-4-enoic acid) was found to be a potent thromboxane receptor binder ($IC_{50}$: 0.841 nM; Ki: 0.549 nM) enantiomer 2 did not appear to bind ($IC_{50}$>10 nM).

Example 31:

Inhibition of Cancer Cell Proliferation

This example demonstrates the anti-proliferative effect of DPD on the growth of cancer cells and illustrates the utility of the analogs described herein for the treatment of cancer.

A human cervical carcinoma cell line (HeLa) engineered to stably express a recombinant biosensor reporter activity and a non-cancer cell line, HaCaT (Boukamp et al., 1988, J. Cell Biol 106(3):761-771) was used with a Caspa Tag kit (commercially available eg from Chemicon). The detection of proliferation was carried out using a high content screening automated flow cytometer.

DPD (Substance 1) was diluted to 20 µM in cell culture medium without serum adjusted to 1% DMSO. Detection of cellular events was performed in duplicate in 96-well plates after 48 hours of treatment in the FL2 (dilution of a proliferative marker) channels of a HTS flow cytometer (FACS Calibur HTS, Becton Dickenson). At day 1, cells were seeded in 96 well plates. Cells were treated with DPD and the appropriate controls on day 2 and analysis was carried out on day 4.

DPD inhibited 90% proliferation of HeLa cells at 20 microM. DPD had no effect on the non-cancer cell line HaCaT, thus establishing a selective antiproliferative effect on cancer cells by DPD (SN1 in Table II).

Example 32

This example illustrates the glucose lowering effect of an enantiomer of the invention in a mouse model.
Materials and Methods.
$KKA^y$ Mice 52 male $KKA^y$ mice were obtained commercially (e.g., from Clea Japan) at an age of 6 weeks and put on a high fat diet upon arrival. Individual mice were housed in IVC Type II cages during both the acclimatization and the experimental phase. Both food (high fat diet) and water were supplied ad libitum.

1 animal per cage. Light 12 h, dark 12 h. Lights on at 06:00 a.m. Temperature: 21-25° C. Relative humidity target range: 55-60%.

Mice were randomized into treatment groups according to their 4-h fasting blood glucose.
Groups:
  Vehicle, ((Z)-6-((2S,4S,5R)-2-(2-chlorophenyl)-4-(2-hydroxyphenyl)-1,3-dioxan-5-yl)hex-4-enoic acid (53 mg/kg), Rosiglitazone (5 mg/kg; positive control).

Treatment:

14-Day oral gavage BID every 12 h.

Finish:

4 hours after the last administration, non-fasting conditions.

High Fat Diet

Gamma irradiated high fat diet was obtained from Research Diets, Inc. New Brunswick, N.J. (Product # D12266B1)

Blood Glucose

Glucose was measured either in whole blood using the Glucotrend stick (Roche Diagnostics Art # 28050) or in serum (see below)

Hematocrit

Blood was collected into heparin containing glass capillaries which were subsequently centrifuged in a "Haematokrit 24" centrifuge (Hettich) at 15'200×g for 10 min at room temperature to obtain the hematocrit value.

Serum Parameters

The following serum parameters were determined on a COBAS INTEGRA 800 auto analyzer (Roche Diagnostics, Switzerland) using the reagents and protocols provided by the supplier.

| | |
|---|---|
| Glucose | (Ordering # 04404483190) |
| Cholesterol | (Ordering # 03039773190) |
| Triglycerides | (Ordering # 20767107322) |
| HDL | (Ordering # 04399803190) |
| AST | (Ordering # 20764949322) |
| ALT | (Ordering # 20764957322) |
| ALP | (Ordering # 03333752190) |

HbA1c Was determined on a Hitachi 917 auto analyzer using the Roche Diagnostics kit (order # 11822039216) according to the protocol provided by the supplier.

The following serum parameters were measured in a micro titer plate format

Insulin Was determined using an ELISA kit (Mercodia, Uppsala, order # 10-1149-01) in a one micro liter sample according to the protocol provided by the supplier.

Fructosamine Was determined in a 96 well format using the Roche Diagnostics kit (order # 11930010216) in 5 micro liter serum according to the protocol provided by the supplier.

FFA Free fatty acids were measured using the NEFA C kit (Wako Chemicals GmbH D-42468 Neuss) according to the protocol of the supplier All measurements were made on Day 14 of administration, except for the food intake and body weight measurements that were made on Day 12.

On Day 12, the number of mice was 10 (vehicle), 14 ((Z)-6-((2S,4S,5R)-2-(2-chlorophenyl)-4-(2-hydroxyphenyl)-1,3-dioxan-5-yl)hex-4-enoic acid, 53 mg/kg) and 10 (rosiglitazone).

On Day 14 the number of mice was 10 (vehicle), 10 ((Z)-6-((2S,4S,5R)-2-(2-chlorophenyl)-4-(2-hydroxyphenyl)-1,3-dioxan-5-yl)hex-4-enoic acid, 53 mg/kg) and 10 (rosiglitazone).

Serum compound levels were measured in 9 (((Z)-6-((2S,4S,5R)-2-(2-chlorophenyl)-4-(2-hydroxyphenyl)-1,3-dioxan-5-yl)hex-4-enoic acid, 53 mg/kg) mice.

Results:

TABLE IV

| | Treatment Groups Average Values ± S.E.M. | | |
|---|---|---|---|
| Measured parameter | Vehicle | (Z)-6-((2S,4S,5R)-2-(2-chlorophenyl)-4-(2-hydroxyphenyl)-1,3-dioxan-5-yl)hex-4-enoic acid 53 mg/kg BID | Rosiglitazone 5 mg/kg BID |
| Serum Glucose (mM) | 42.5 ± 1.6 | 31.9 ± 3.6* | 18.8 ± 2.2*** |
| HbA1C (%) | 8.8 ± 0.2 | 7.8 ± 0.3* | 7.8 ± 0.4* |
| Fructosamine (mM) | 0.38 ± 0.01 | 0.41 ± 0.03 | 0.35 ± 0.03 |
| Insulin (µg/L) | 30.9 ± 3.3 | 39.1 ± 8.8 | 17.9 ± 4.2* |
| FFA (mM) | 2.2 ± 0.1 | 1.7 ± 0.3 | 1.3 ± 0.1*** |
| TG (mM) | 2.2 ± 0.2 | 2.0 ± 0.3 | 1.0 ± 0.2** |
| HDL (mM) | 2.7 ± 0.1 | 3.1 ± 0.2 | 3.6 ± 0.2** |
| Total Cholesterol (mM) | 3.2 ± 0.1 | 3.6 ± 0.3 | 4.0 ± 0.4 |
| Body Weight (g) | 45.9 ± 1.0 | 45.4 ± 1.0 | 49.5 ± 1.0* |
| Food Intake (g/day) | 5.5 ± 0.2 | 5.0 ± 0.6 | 4.5 ± 0.6 |
| Heart weight (mg) | 204.8 ± 5.3 | 208.5 ± 7.6 | 226.2 ± 6.9* |
| Hematocrit (%) | 42.1 ± 1.4 | 40.1 ± 1.6 | 40.3 ± 1.5 |
| AST (dU/L) | 7.1 ± 0.6 | 7.7 ± 1.0 | 10.1 ± 0.9 |
| ALT (dU/L) | 5.8 ± 0.6 | 5.1 ± 0.6 | 8.9 ± 0.9 |
| ALP (dU/L) | 30.1 ± 1.3 | 21.5 ± 1.6 | 26.0 ± 1.7 |
| Serum (Z)-6-((2S,4S,5R)-2-(2-chlorophenyl)-4-(2-hydroxyphenyl)-1,3-dioxan-5-yl)hex-4-enoic acid (ng/ml) | NA | 161 ± 60 | NA |

Statistical difference (P) from vehicle control is:

*p < 0.05,

**p < 0.01,

***p < 0.001.

Circulating glucose is one of the primary measurements made in the clinic for diagnosis of diabetes because it reflects the actual levels. The main aim of a glucose-lowering compound is to lower circulating glucose.

Conclusion: Both (Z)-6-((2S,4S,5R)-2-(2-chlorophenyl)-4-(2-hydroxyphenyl)-1,3-dioxan-5-yl)hex-4-enoic acid, and the positive control (Rosiglitazone), decreased (the latter slightly more) the circulating glucose levels in the hyperglycemic mice, indicative of a glucose-lowering effect of (Z)-6-((2S,4S,5R)-2-(2-chlorophenyl)-4-(2-hydroxyphenyl)-1,3-dioxan-5-yl)hex-4-enoic acid.

Fructosamines, which are formed from glycosylated blood proteins, and HbA1c (glycosylated hemoglobin) reflect the integrated circulating glucose levels over a prolonged period of time. Blood proteins are glycosylated irreversibly in a non-enzymatic manner. Due to the shorter life span of serum proteins as compared to erythrocytes fructosamine is considered to be the shorter range parameter.

Conclusion: HbA1c levels were decreased by the positive control (Rosiglitazone) and by (Z)-6-((2S,4S,5R)-2-(2-chlorophenyl)-4-(2-hydroxyphenyl)-1,3-d ioxan-5-yl)hex-4-enoic acid; fructosamine levels were not influenced. PPAR-γ agonists are known not to have an immediate onset, but to require some time to onset, 2-3 weeks in humans, and even longer time to reach maximal effect. The glucose levels may have been of lower magnitude, and not for a long enough period, to have a uniform impact on HbA1c and fructosamine levels.

Insulin is a hormone that increases glucose uptake from the circulation into tissues such as muscle, fat, and adipose. The KKA$^y$ mouse is a hyperinsulinemic model, i.e. it is not deficient in insulin.

Conclusion: Only the positive control reduced insulin levels, suggesting that (Z)-6-((2S,4S,5R)-2-(2-chlorophenyl)-4-(2-hydroxyphenyl)-1,3-dioxan-5-yl(hex-4-enoic acid has lower efficacy, as shown by the effect on circulating glucose levels. High insulin levels reflect either high circulating glucose levels or insulin resistance. Thus, it seems that while glucose levels are decreased, insulin resistance has not yet decreased; probably because the glucose effect is recent, smaller, and the resistance will take longer.

High circulating levels of triglycerides (TG), total cholesterol, and free fatty acids (FFA), as well as low high density lipoprotein (HDL) cholesterol are cardiovascular risk factors.

Conclusion: (Z)-6-((2S,4S,5R)-2-(2-chlorophenyl)-4-(2-hydroxyphenyl)-1,3-dioxan-5-yl(hex-4-enoic acid slightly decreased the FFA. The positive control (Rosiglitazone) increased HDL, decreased triglycerides, and FFA.

Body weight of the mice was measured since one of the side effects of thioglitazones is increased body weight in the mouse and human. Moreover, decreased body weight is an indication of side effects.

Conclusion: The body weight was increased only by the positive control (Rosiglitazone), consistent with previous observations. (Z)-6-((2S,4S,5R)-2-(2-chlorophenyl)-4-(2-hydroxyphenyl)-1,3-dioxan-5-yl)hex-4-enoic acid did not alter body weight.

Heart weight was also measured:

Conclusion: The heart weight is increased in the rosiglitazone group, likely in compensation for the increased body weight at termination. (Z)-6-((2S,4S,5R)-2-(2-chlorophenyl)-4-(2-hydroxyphenyl)-1,3-dioxan-5-yl)hex-4-enoic acid treatment had no effect on heart weight.

An increase in hematocrit might indicate a tendency of dehydration, i.e. decrease in water intake.

Conclusion: No effect on hematocrit was observed in any of the groups, suggesting that there was no dehydration.

The common liver function marker enzymes aspartate aminotransferase (AST), alanine aminotransferase (ALT), and alkaline phosphatases (ALP), are measured to assure that are no side effects on the liver.

Conclusion: Serum AST, ALT, and ALP were not increased, suggesting that the doses used were devoid of adverse effects.

Serum (Z)-6-((2S,4S,5R)-2-(2-chlorophenyl)-4-(2-hydroxyphenyl)-1,3-dioxan-5-yl)hex-4-enoic acid levels were measured in order to document that the animals had in fact the intended compound in the circulation.

Example 33:

Human Recombinant (*E. Coli*) PPARgamma (h) Binding Assay

This example illustrates the binding of a compound of the invention to recombinant human PPAR gamma.

Ligand Concentration: [3H]-rosiglitazone 10 nM

Non Specific Binding: rosiglitazone (10 µM)

Incubation: 120 min at 4° C.

The results are expressed as a percent of control specific binding ((measured specific binding/control specific binding)×100) obtained in the presence of the test compounds. The $IC_{50}$ values (concentration causing a half-maximal inhibition of control specific binding) and Hill coefficients (nH) were determined by non-linear regression analysis of the competition curves generated with mean replicate values using Hill equation curve fitting (Y=D+[(A D)/(1+(C/C50) nH)], where Y=specific binding, D=minimum specific binding, A=maximum specific binding, C=compound concentration, C50=$IC_{50}$, and nH=slope factor). This analysis was performed using a software developed at Cerep (Hill software) and validated by comparison with data generated by the commercial software SigmaPlot® 4.0 for Windows® (© 1997 by SPSS Inc.). The inhibition constants (Ki) were calculated using the Cheng Prusoff equation (Ki=$IC_{50}$/(1+(L/KD)), where L=concentration of radioligand in the assay, and KD=affinity of the radioligand for the receptor).

TABLE V

| | PPARgamma binding | |
|---|---|---|
| Compound: | $IC_{50}$ (µM) | Ki (µM) |
| (Z)-6-((2R,4R,5S)-2-(2-chlorophenyl)-4-(2-hydroxyphenyl)-1,3-dioxan-5-yl)hex-4-enoic acid | @ 30 µM no binding | |
| (Z)-6-((2S,4S,5R)-2-(2-chlorophenyl)-4-(2-hydroxyphenyl)-1,3-dioxan-5-yl)hex-4-enoic acid | 4.9; 12 | 1.8; 4.3 |
| (Z)-6-(-2-(2-chlorophenyl)-4-(2-hydroxyphenyl)-1,3-dioxan-5-yl)hex-4-enoic acid | 21 | |
| Picotamide | @ 10 µM no binding | |

Example 34:

Effect on Arterial Thrombosis in a Mouse Model

This example illustrates the effect of a compound of the invention on thrombosis in a mouse model.

Materials

Vehicle (DMSO/PEG 400, 5/95)

Dose of 1, 3, 10, 30, 100 and 300 mg/kg ((Z)-6-((2S,4S,5R)-2-(2-chlorophenyl)-4-(2-hydroxyphenyl)-1,3-dioxan-5-yl)hex-4-enoic acid) in vehicle Saline Aspirin (dose of 100 mg and 600 mg/kg in vehicle)

Aspirin (Aspégic from Sanofi Synthelabo; dissolved in Saline)

Clopidogrel (Plavix from Sanofi Pharma; dissolved in $H_2O$)

The solutions were diluted 3.3-fold in saline and 100 µl/25 g was injected. Thus, the above-mentioned doses of 100 and 300 mg/kg of (Z)-6-((2S,4S,5R)-2-(2-chlorophenyl)-4-(2-hydroxyphenyl)-1,3-dioxan-5-yl)hex-4-enoic acid correspond to final doses of 30 and 100 mg/kg.

It should be noted that PEG is very hygroscopic and that DMSO affects platelet aggregation ex vivo at very low concentration. For i.v. injection in mice this does not appear to be a preferable solvent.

During the experiments, a soluble potassium salt of the drug was provided, diluted in saline. Of this formulation, 100 µl/25 g was injected i.v. in the tail vein (dose of 100 mg/kg).

Thrombosis Model

Solutions are injected (100 µl/25 g body weight) i.v. in the tail vein over 2 min to obtain doses of (Z)-6-((2S,4S,5R)-2-(2-chlorophenyl)-4-(2-hydroxyphenyl)-1,3-dioxan-5-yl)hex-4-enoic acid of 30 mg/kg and 100 mg/kg. Aspirin is given the same way at a dose of 200 mg/kg. Clopidogrel is administered by oral gavage at a dose of 20 mg/kg at 6-7 hours prior to the experiment. The solutions were coded (except for clopidogrel) and the operator was blinded to the code. The animals assigned to each group were matched for body weight. All mice used were 8-10 weeks old males and were in a 100% Swiss genetic background.

The arterial thrombosis model was performed essentially as described by Nagai et al. (Nagai N, Lijnen H R, Van Hoef B, Hoylaerts M F, Van Vlijmen B J M. Nutritionally induced obesity reduces the arterial thrombotic tendency of Factor V Leiden mice. Thromb Haemost. 2007 October; 98(4):858-863 (published on-line; doi: 10.1160/TH07-04-0306). Briefly, a small piece of tissue paper saturated with a 5% $FeCl_3$ solution is deposited on the isolated femoral artery of the mice for 2 min, followed by extensive washing with saline (application starts at about 10 min after i.v. injection). Blood flow in the hind paws is monitored using a scanning laser Doppler flow meter and digitized images are collected during 30 min at 15s intervals (starting 1 min after arresting $FeCl_3$ treatment). The flow in each image is expressed as a percentage of that at the contralateral side, and data are averaged for all 120 images to determine total flow. The same analysis is performed for 10 min intervals (which gives essentially the same information as the area under the curve). The occlusion time is recorded as the first image that showed 0% flow. Flow before treatment is recorded as 100%, and that in occluded arteries as 0%. At the end of the experiment, blood is collected on 0.01M citrate by heart puncture for determination of blood cell counts. Plasma is prepared by centrifugation and stored at −20° C. for determination of drug levels.

Statistical analysis for differences between two groups is performed by non-parametric Student t-test. Occlusion times >30 min were considered equal to 30 min for statistical analysis. It should be noted that this approach may result in a statistical bias, the more so because the number of experiments is not the same in the different groups. Significance is set at p<0.05.

Results

A total of 59 mice were used in this study, of which 4 in the preliminary experiments to optimize the administration scheme. One mouse (D947) died during the experiment (5 min after $FeCl_3$ application corresponding to about 15 min after injection of the drug; cause of death unknown) in the 100 mg/kg drug dose in vehicle.

Occlusion Times

Aspirin at 200 mg/kg had no effect on the occlusion time; the somewhat shorter occlusion time as compared to vehicle is due to two experiments with delayed occlusion in the vehicle group (mean±SEM=7'18"±0'33" without these)

Clopidogrel totally prevents occlusion within 30 min in 6/7 experiments. In one experiment rapid occlusion was observed (Z)-6-((2S,4S,5R)-2-(2-chlorophenyl)-4-(2-hydroxyphenyl)-1,3-dioxan-5-yl(hex-4-enoic acid at a dose of 30 mg/kg in vehicle slightly prolongs the occlusion time as compared to aspirin (p=0.024), but has no effect as compared to vehicle.

(Z)-6-((2S,4S,5R)-2-(2-chlorophenyl)-4-(2-hydroxyphenyl)-1,3-dioxan-5-yl(hex-4-enoic potassium at a dose of 100 mg/kg in saline prolonged the occlusion time (p=0.0006 versus aspirin; p=0.017 versus saline only).

The results shows inhibition of formation of $FeCl_3$ induced occlusion in the mouse model.

Blood Flow

Aspirin at 200 mg/kg had no significant effect on the total blood flow (p=0.53 versus vehicle).

Clopidogrel significantly improved total blood flow (p=0.0087, versus vehicle, including experiment B130).

(Z)-6-((2S,4S,5R)-2-(2-chlorophenyl)-4-(2-hydroxyphenyl)-1,3-dioxan-5-yl(hex-4-enoic acid at a dose of 30 mg/kg in vehicle had no effect on total blood flow (p=0.84 versus vehicle and p=0.65 versus aspirin).

(Z)-6-((2S,4S,5R)-2-(2-chlorophenyl)-4-(2-hydroxyphenyl)-1,3-dioxan-5-yl(hex-4-enoic acid at a dose of 100 mg/kg in vehicle improved total blood flow as compared to aspirin (p=0.055), but not as compared to vehicle (p=0.45).

In all groups, the evolution of blood flow with time was compatible with the observed occlusion time. In the time window 0-10 min, 100 mg/kg (Z)-6-((2S,4S,5R)-2-(2-chlorophenyl)-4-(2-hydroxyphenyl)-1,3-dioxan-5-yl (hex-4-enoic acid administered in vehicle was associated with significantly higher flow as compared to aspirin (p=0.0002) but not as compared to vehicle only (p=0.11). The same trends were observed at later time points.

(Z)-6-((2S,4S,5R)-2-(2-chlorophenyl)-4-(2-hydroxyphenyl)-1,3-dioxan-5-yl(hex-4-enoic potassium at a dose of 100 mg/kg in saline significantly improved total blood flow as compared to either saline (p=0.0032) or aspirin (p=0.0021). Furthermore, in the same time window 100 mg/kg (Z)-6-((2S,4S,5R)-2-(2-chlorophenyl)-4-(2-hydroxyphenyl)-1,3-dioxan-5-yl)hex-4-enoic potassium in saline was associated with significantly higher blood flow as compared to either saline alone (p=0.009) or to aspirin (p=0.0006). The same trends were observed at later time points. With 100 mg/kg (Z)-6-((2S,4S,5R)-2-(2-chlorophenyl)-4-(2-hydroxyphenyl)-1,3-dioxan-5-yl(hex-4-enoic in saline for 10-20 min, p=0.0066 versus saline and p=0.027 versus aspirin; for 20-30 min, p=0.016 versus saline and p=0.031 versus aspirin.

Blood Cell Analysis

Table VI summarizes the results of blood cell analysis performed on a sample taken at the end of the observation period. (Z)-6-((2S,4S,5R)-2-(2-chlorophenyl)-4-(2-hydroxyphenyl)-1,3-dioxan-5-yl)hex-4-enoic is referred to in Table VI as EV.

No major changes were observed as compared to aspirin or clopidogrel; some moderate differences were observed in white blood cell distribution.

TABLE VI

Blood cell analysis

| | Vehicle (n = 11) | Saline (n = 4) | Aspirin (n = 7) | Clopidogrel (n = 6) | EV 30 mg/kg vehicle (n = 4) | EV 100 mg/kg vehicle (n = 9) |
|---|---|---|---|---|---|---|
| White blood cells ($\times 10^3/\mu l$) | 1.9 ± 0.47 | 1.3 ± 1.0 | 1.4 ± 0.42 | 0.62 ± 0.22 | 0.95 ± 0.17 | 1.5 ± 0.46 |
| Neutrophils (%) | 37 ± 5.6 | 42 ± 14 | 39 ± 11 | 50 ± 7.2 | 56 ± 5.3 | 34 ± 12 |
| Lymphocytes (%) | 62 ± 5.6 | 56 ± 15 | 60 ± 11 | 47 ± 7.8 | 42 ± 4.7 | 58 ± 11 |
| Platelets ($\times 10^3/\mu l$) | 1005 ± 44 | 935 ± 77 | 1020 ± 59 | 1060 ± 106 | 1020 ± 89 | 895 ± 46 |
| Red blood cells (($\times 10^6/\mu l$) | 8.4 ± 0.30 | 9.1 ± 0.25 | 9.3 ± 0.10 | 9.0 ± 0.36 | 9.1 ± 0.26 | 9.2 ± 0.17 |
| Hemoglobin (g/dl) | 14 ± 0.49 | 15 ± 0.40 | 15 ± 0.19 | 15 ± 0.60 | 15 ± 0.28 | 15 ± 0.30 |
| Hematocrit (%) | 66 ± 2.2 | 64 ± 7.8 | 72 ± 0.60 | 72 ± 2.7 | 62 ± 7.3 | 70 ± 3.5 |

Data are mean ± SEM of n experiments

EV = (Z)-6-((2S,4S,5R)-2-(2-chlorophenyl)-4-(2-hydroxyphenyl)-1,3-dioxan-5-yl)hex-4-enoic acid Example 35

Thromboxane Receptor Binding Assays were Performed as Described in Example 30

TP Receptor Radioligand Binding Studies:

Using these experimental conditions Human recombinant HEK-293 cells, Ligand: 5 nM [$^3$H] SQ-29548, Vehicle: 1% DMSO, Incubation Time, Temp: 30 min at 25° C., Incubation Buffer: 50 mM Tris-HCl, pH 7.4, 154 mM NaCl, Non-Specific Ligand: 1 µM SQ-29548, KD: 9.4 nM, Bmax: 5.1 pmole/mg protein, Specific Binding: 93%, the assay performed according to Hedberg A, Hall S E, Ogletree M L, Harris D N and Liu E C-K (1988) Characterization of [5, 6-3H]SQ 29,548 as a high affinity radioligand, binding to thromboxane A2/prostaglandin H2-receptors in human platelets. J Pharmacol Exp Ther. 245(3):786-92792, and Saussy D L Jr, Mais D E, Burch R M and Halushka P V (1986) Identification of a putative thromboxane A2/prostaglandin H2 receptor in human platelet membranes.

J Biol. Chem. 261(7):3025-9.

Human Platelet Thromboxane Synthase Assay:

Using these experimental conditions Substrate: 10 µM PGH$_2$Vehicle: 1% DMSO Pre-incubation time, temp: 15 min at 25° C., Incubation time, temp: 3 min at 25° C. Incubation Buffer: 10 mM Tris-HCl, pH 7.4, Quantification Method: EIA quantification of TxB$_2$, the assay performed according to Borsch-Haubold A G, Pasquet S, Watson S P. (1998) Direct inhibition of cyclooxygenase-1 and –2 by the kinase inhibitors SB 203580 and PD 98059. SB 203580 also inhibits thromboxane synthase. J Biol. Chem. 273(44):28766-72, and Iizuka K, Akahane K, Momose D, Nakazawa M, Tanouchi T, Kawamura M, Ohyama I, Kajiwara I, Iguchi Y, Okada T, Taniguchi K, Miyamoto T, Hayashi M. (1981) Highly selective inhibitors of thromboxane synthetase. 1. Imidazole derivatives. J Med. Chem. 24(10):1139-48.

TP Receptor Platelet Aggregation—Rabbit:

Using these experimental conditions New Zealand Rabbit (2.75±0.25 kg) platelet rich plasma, Vehicle: 0.3% DMSO, Assay: Inhibition of 1.5 µM U-46619-induced platelet aggregation, Incubation Time, Temp: 5 min at 37° C., Incubation Buffer: Trisodium Citrate (0.13 M) treated platelet rich plasma, Bath Volume: 0.5 mL, Time of Assessment: 5 min, Quantification Method: Optical Density Change. the assay performed according to Patscheke, H., and Stregmeier, K. (1984) Investigations on a selective non-prostanoic thromboxane antagonist, BM13, 177, in human platelets. Thrombosis Research 33:277-288

TP Receptor Platelet Aggregation—Human:

Using these experimental conditions Human (60±10 kg) platelet rich plasma, Vehicle: 0.3% DMSO, Assay: Inhibition of 3 µM U-46619-induced platelet aggregation, Incubation Time, Temp: 5 min at 37° C., Incubation Buffer: Trisodium Citrate (0.13M)—treated fresh platelet rich plasma, Bath Volume: 0.5 mL, Time of Assessment: 5 minutes, Quantification Method: Optical Density Change the assay performed according to Patscheke, H., and Stregmeier, K. (1984) Investigations on a selective non-prostanoic thromboxane antagonist, BM13, 177, in human platelets. Thrombosis Research 33:277-288

IC$_{50}$ Calculation:

The data were transformed to semi-log and then analysed using non-linear regression to a four-parameter dose-response curve Y=Bottom+(Top-Bottom)/(1+10^((Log EC50−X)*HillSlope)) using the log(agonist) vs. response—Variable slope function of GraphPad Prism software (http://graphpad.com/help/prism5/prism5help.html?usingnonlinear_regression_step_by_s.htm).

| Compound: | Platelet aggregation | | | | Thromboxane receptor (TP) binding Human recombinant HEK-293 cells | | | Thromboxane synthase Human platelet | |
|---|---|---|---|---|---|---|---|---|---|
| | Human Inhibition (%) at | IC$_{50}$ (nM) | Rabbit Inhibition (%) at | | Inhibition (%) @ 10 µM | IC$_{50}$ (nM) | Ki (nM) | Inhibition (%) at 5 µM | IC$_{50}$ (nM) |
| | | | 10 µM | 30 µM | | | | | |
| A | 13@30 µM | | | 15 @ 0.1 mM | 94, 96 | 1260 | 825 | 25, 28 @ 10 µM | 12100 |
| B | 94@1 µM 97@8 µM 100@16 µM | 310 | | 100 | 102 | 0.84 | 0.55 | 43, 61 @ 10 µM | 7020 |
| 3 | | | 33 | | 98 | | | 12 | |
| 4 | | | | | 85 | 1870 | 1220 | 52 @ 30 µM | 17500 |
| 5 | | | | | 96 @ 0.3 µM | 23.4 | 15.3 | 62 @ 30 µM | 20400 |
| Picotamide | | | | 36, 21 @ 0.1 mM | 66 | 5950 | 3880 | 53 at 10 µM | 10100 |

Compound A: (Z)-6-((2R,4R,5S)-2-(2-chlorophenyl)-4-(2-hydroxyphenyl)-1,3-dioxan-5-yl)hex-4-enoic acid (enantiomer 2)

Compound B: (Z)-6-((2S,4S,5R)-2-(2-chlorophenyl)-4-(2-hydroxyphenyl)-1,3-dioxan-5-yl)hex-4-enoic acid (enantiomer 1)

Compound 3: (Z)-6-(-2-(2-chlorophenyl)-4-(2-methoxyphenyl)-1,3-dioxan-5-yl)hex-4-enoic acid Compound 4: (Z)-6-((2R,4R,5S)-2-(2-chlorophenyl)-4-(2-methoxyphenyl)-1,3-dioxan-5-yl)hex-4-enoic acid Compound 5: (Z)-6-((2S,4S,5R)-2-(2-chlorophenyl)-4-(2-methoxyphenyl)-1,3-dioxan-5-yl)hex-4-enoic acid.

Example 36

Figure 16:
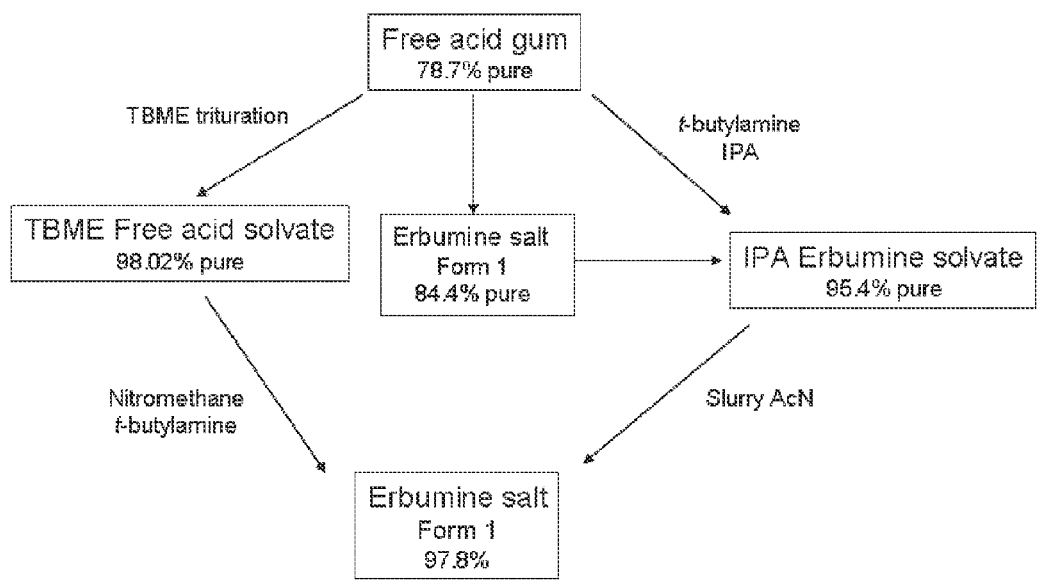
FIG. 16 illustrates the conversion of (Z)-6-((2S,4S,5R)-2-(2-chlorophenyl)-4-(2-hydroxyphenl)-1,3-dioxan-5-yl)hex-4-enoic acid gum into various solid salts and solvates.

Preparation of Solvates and Salts of (Z)-6-((2S,4S,5R)-2-(2-chlorophenyl)-4-(2-hydroxyphenyl)-1,3-dioxan-5-yl)hex-4-enoic Acid (Z)-6-((2S,4S,5R)-2-(2-chlorophenyl)-4-(2-hydroxyphenyl)-1,3-dioxan-5-yl)hex-4-enoic acid (SN1 in Table II), is gum like oil. The acid can be converted into various solid salts and solvates as illustrated in FIG. 16.

Figure 11:
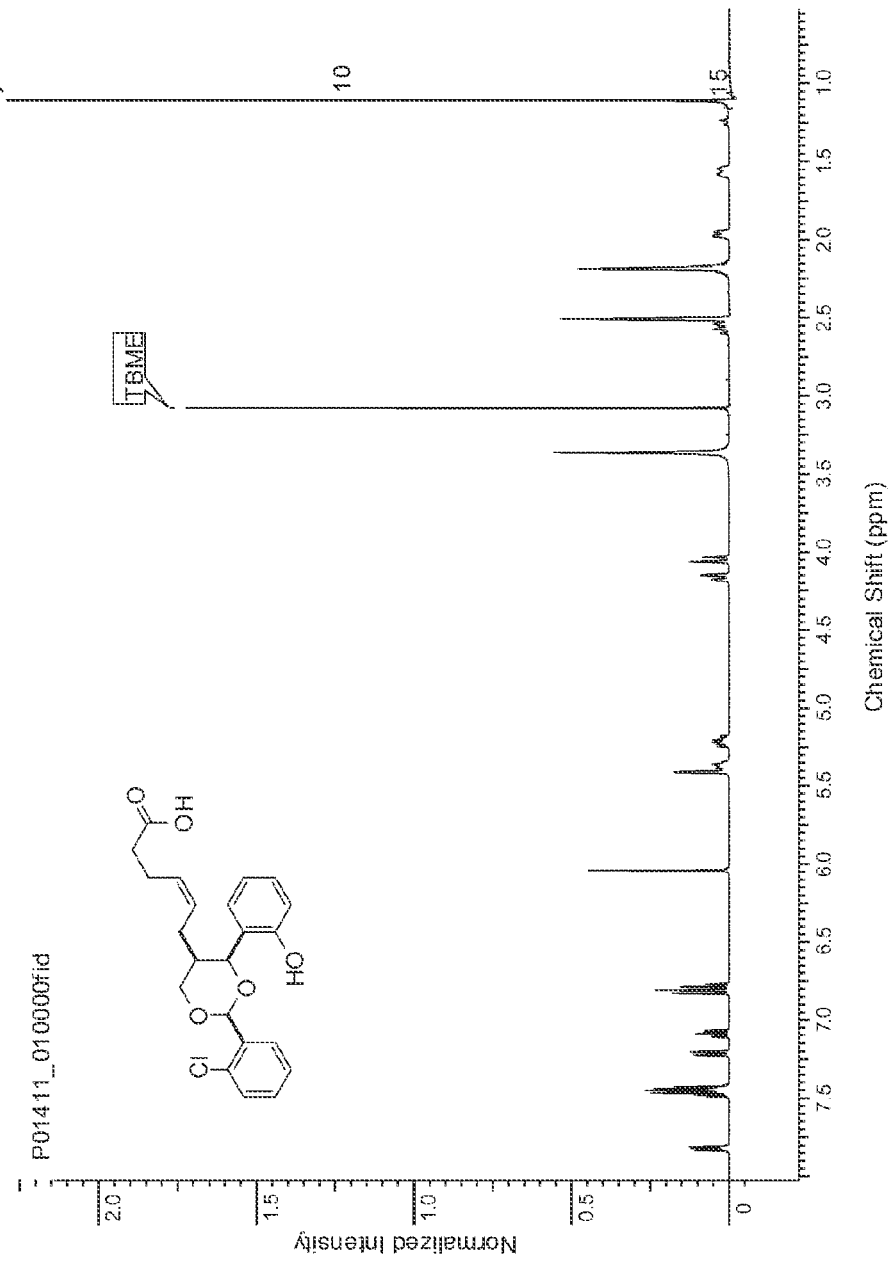
FIG. 11 illustrates the $^1$H NMR of TBME solvate of (Z)-6-(2-(2-chlorophenyl)-4-(2-hydroxyphenyl-1,3-dioxan-cis-5-yl)hex-4-enoic acid.
Figure 12:
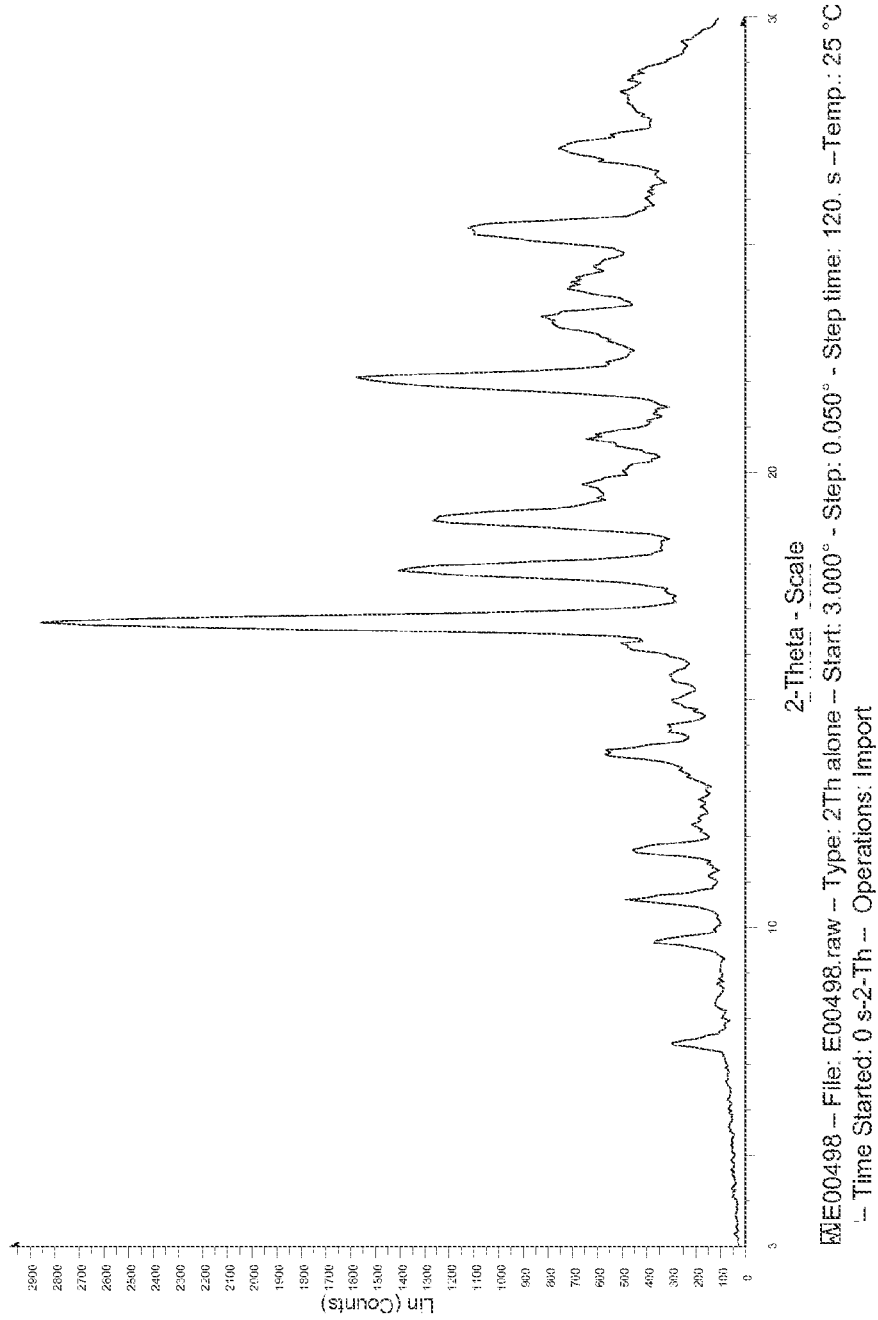
FIG. 12 illustrates the XRPD diffractogram of TBME solvate of (Z)-6-(2-(2-chlorophenyl)-4-(2-hydroxyphenyl-1,3-dioxan-cis-5-yl)hex-4-enoic acid.

The acid (14.08 g) was triturated in tert-butyl methyl ether (TBME, 32 mL, 2.25 vol). The solution was stirred for 30 min. at room temperature and for 30 min. in an ice bath. The precipitate thus obtained was collected by filtration, washed with ice-cold TBME (2×15 mL) and dried in vacuo to give a solid (8.17 g, 58%). The solid obtained was characterized using a Bruker 400 MHz NMR instrument and X-Ray Powder Diffraction patterns were collected on a Bruker AXS C2 GADDS diffractometer using Cu Kα radiation (40 kV, 40 mA), and thermogravimetric analysis (TGA) was performed using TA Instruments Q500 TGA. The NMR and XPRD data are shown in FIGS. 11 and 12 respectively.

The $^1$H NMR spectrum and TGA trace are consistent with 0.72 mol of TBME present. The TGA and DSC traces suggest that there are two desolvation steps involved. The first desolvation endotherm has an onset of 55° C., and the second desolvation endotherm occurs at 75° C. There is no evidence of a melting endotherm. The purity of the compound was determined to be 98.0% by HPLC.

Variable temperature XRPD shows that the material is the same crystalline form until a temperature of 70° C. At higher temperature the material becomes a gum and gives an amorphous pattern. On cool down to 30° C. the material remains a gum with an amorphous XRPD pattern.

Conversion of TBME Solvate to Erbumine Salt

Figure 13:
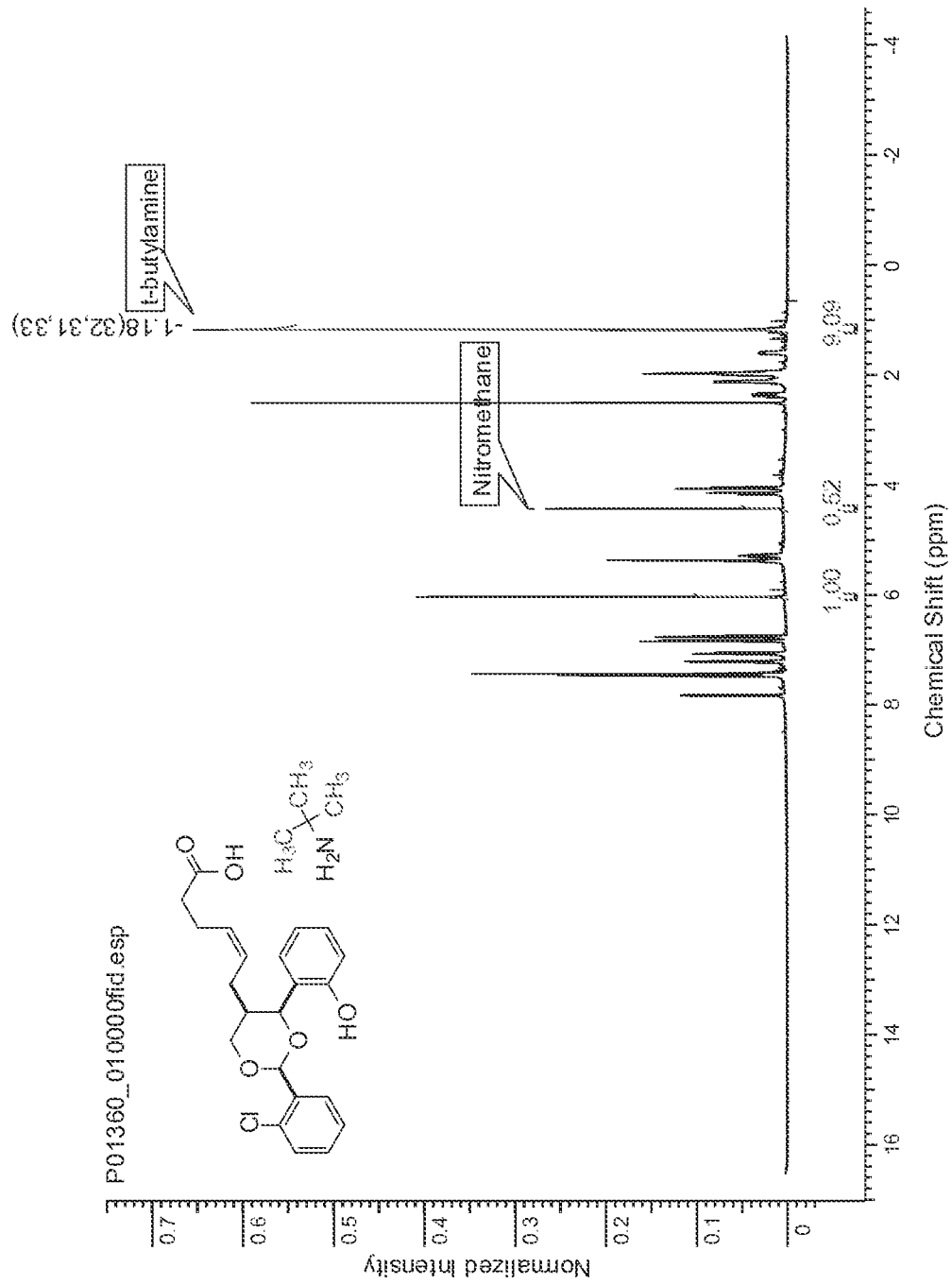
FIG. 13 illustrates the $^1$H NMR of erbumine salt of (Z)-6-(2-(2-chlorophenyl)-4-(2-hydroxyphenyl-1,3-dioxan-cis-5-yl)hex-4-enoic acid.
Figure 14:
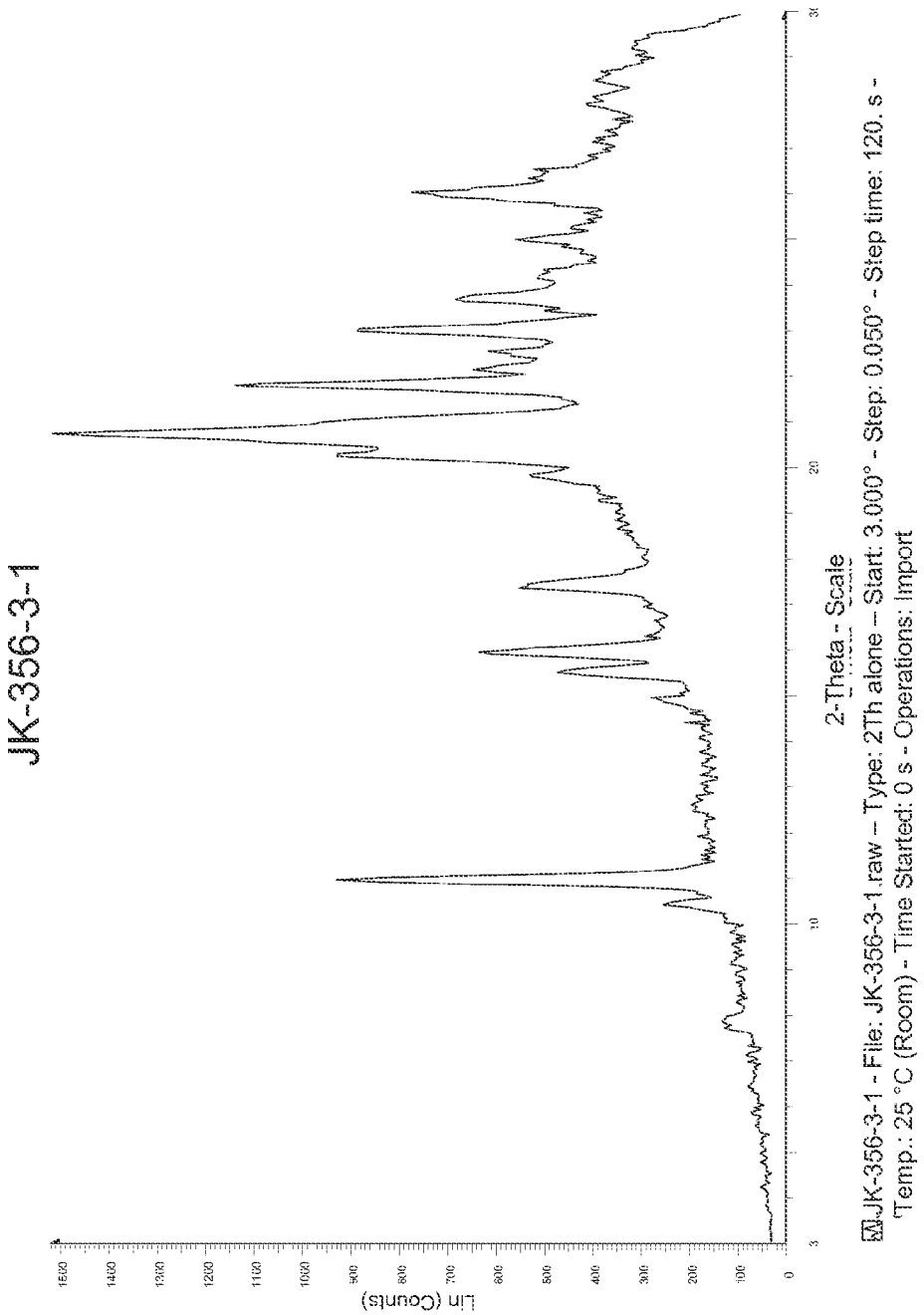
FIG. 14 illustrates the XRPD diffractogram of erbumine salt of (Z)-6-(2-(2-chlorophenyl)-4-(2-hydroxyphenyl-1,3-dioxan-cis-5-yl)hex-4-enoic acid.

The resulting TBME free acid solvate (8.07 g, 20.0 mmol) was dissolved in nitromethane (16 mL). t-butylamine (2.5 mL, 1.2 eq) was added at room temperature with constant stirring and the resulting residue was then stirred over ice for a further 30 min. to afford a gum like solid. The gum was triturated with acetonitrile (20 mL) and the resulting precipitate was collected by filtration. The solid was made into uniform particle size and dried in vaccuo at RT for 48 hours and then at 40° C. for a further 72 hours to yield 7.46 g (78.5%) of a white solid material. The $^1$H NMR and XPRD diffractogram are shown in FIGS. 13 and 14 respectively. The $^1$H NMR shows that 0.17 mol of nitromethane and 1 mol t-butylamine are present in the solid that was found to be 97.8% pure by HPLC. Amount of nitromethane is further decreased by drying. The data from TGA show a gradual weight loss onset ~100° C., consistent with the loss of t-butylamine and the DSC shows endotherm onset at 130° C., also consistent with the loss of t-butylamine.

In another method, the acid (452.23 mg, 1.12 mmol) was dissolved in IPA (2 mL) at room temperature. The solution was heated to 50° C. and t-butylamine added. A crystalline material precipitated after 1 hour. The volume of IPA was increased to 23 mL and the material redissolved with heating and cooled to room temperature over 48 hours. A crystalline white material was obtained in 34% yield. Characterisation of this material identified it as an IPA solvate with a chemical purity of 95.4%. The diffractogram (FIG. 15) shows the formation of the erbumine salt of the compound as an IPA solvate.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

The invention claimed is:

1. A compound which is (Z)-6-(2S,4S,5R)-2-(2-chlorophenyl)-4-(2-hydroxyphenyl)-1,3-dioxan-5-yl)hex-4-enoic acid tert-butylamine salt.

2. A method of treating insulin resistance or diabetes, comprising administering to a patient in need thereof a therapeutically effective amount of the compound of claim 1.

3. A crystalline compound represented by the formula:

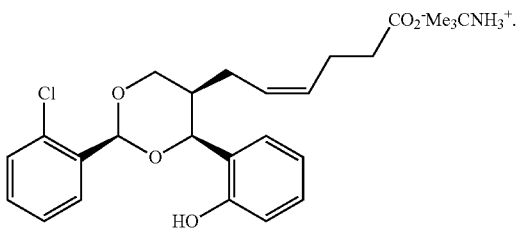

4. A method of treating a clinical condition that is a PPAR-mediated disease or condition in an individual in need thereof, comprising administering to said individual a therapeutically effective amount of the compound of claim 1.

5. The method according to claim 4, wherein said clinical condition is selected from the group consisting of diabetes, cancer; inflammation, AIDS, metabolic syndrome, obesity, pre-diabetes, hypertension and dyslipidemia.

6. A method of treating a clinical condition associated with TP in an individual in need thereof, said method comprising a therapeutically effective amount of a compound of claim 1.

7. The method according to claim 6, wherein said clinical condition is selected from the group consisting of myocardial infarction, thrombosis, thrombotic disorders, pulmonary hypertension, atherosclerosis, diabetic nephropathy, retinopathy, peripheral arterial disease, lower limb circulation, pulmonary embolism, thrombus formation, stent-triggered thrombus formation, stent-triggered hyperplasia, stent-induced restenosis, hyperplasia, septic shock, preeclampsia, asthma, rhinitis, allergic rhinitis, tumour angiogenesis and metastasis.

8. A compound according to claim 1 which is a crystalline form of (Z)-6-((2S,4S,5R)-2-(2-chlorophenyl)-4-(2-hydroxyphenyl)-1,3-dioxan-5-yl)hex-4-enoic acid tert-butylamine salt having an X-ray powder diffraction pattern as shown in FIG. 14.

9. A compound according to claim 1, which is a crystalline form of (Z)-6-((2S,4S,5R)-2-(2-chlorophenyl)-4-(2-hydroxyphenyl)-1,3-dioxan-5-yl)hex-4-enoic acid tert-butylamine salt having an X-ray powder diffraction pattern with peaks at about 15.9, 20.3, and 21.9 degrees 2θ.

10. A compound according to claim 1, which is a crystalline form of (Z)-6-((2S,4S,5R)-2-(2-chlorophenyl)-4-(2-hydroxyphenyl)-1,3-dioxan-5-yl)hex-4-enoic acid tert-butylamine salt having an X-ray powder diffraction pattern with peaks at about 10.9, 15.9, 20.3, 20.7, and 21.9 degrees 2θ.

Figure 15:
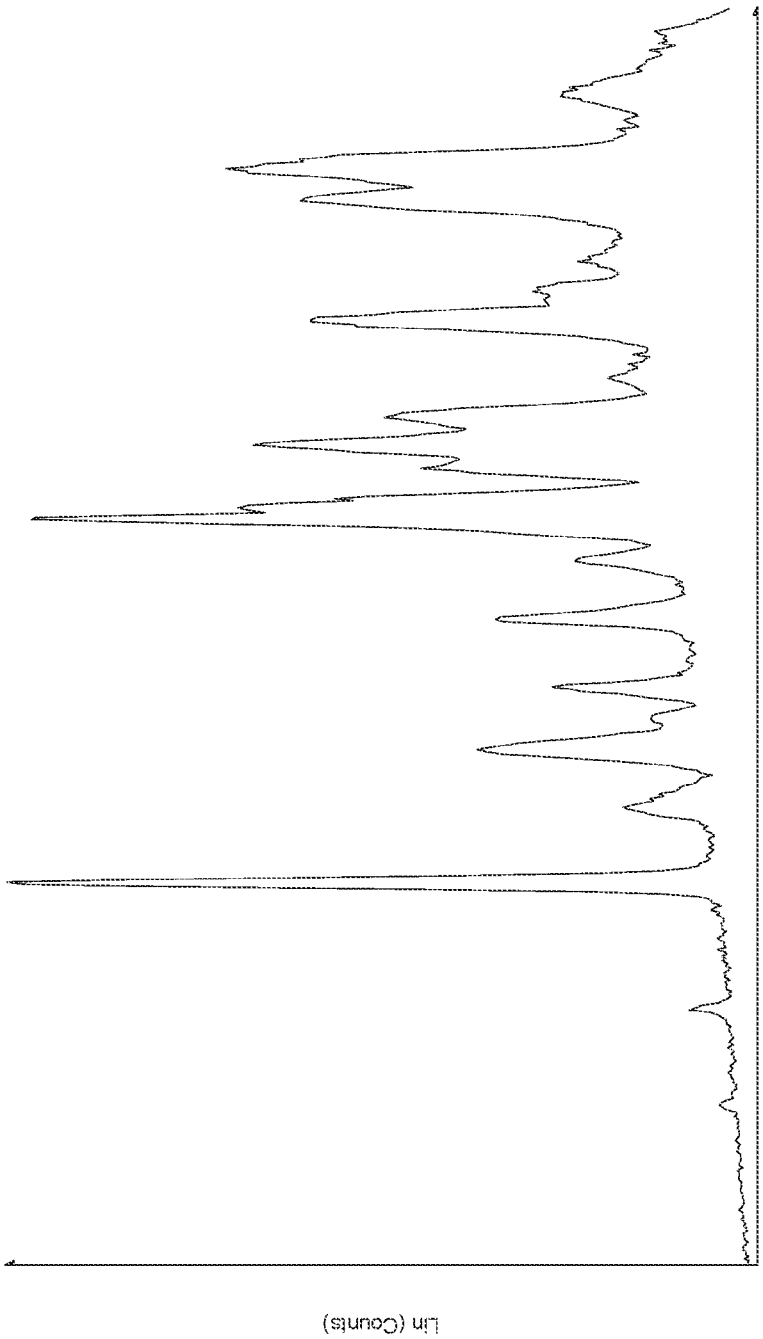
FIG. 15 illustrates the XRPD diffractogram of IPA solvate of erbumine salt of (Z)-6-(2-(2-chlorophenyl)-4-(2-hydroxyphenyl-1,3-dioxan-cis-5-yl)hex-4-enoic acid.

11. A compound which is a crystalline form of an isopropyl alcohol solvate of (Z)-6-((2S,4S,5R)-2-(2-chlorophenyl)-4-(2-hydroxyphenyl)-1,3-dioxan-5-yl)hex-4-enoic acid tert-butylamine salt having an x-ray powder diffraction pattern as shown in FIG. 15.

12. A compound which is a crystalline form of an isopropyl alcohol solvate of (Z)-6-((2S,4S,5R)-2-(2-chlorophenyl)-4-(2-hydroxyphenyl)-1,3-dioxan-5-yl)hex-4-enoic acid tert-butylamine salt having an x-ray powder diffraction pattern with peaks at about 16.8, 17.9, and 25.4 degrees 2θ.

13. A compound according to claim 12, wherein the solvate has an X-Ray Powder Diffraction pattern with peaks at about 10.6, 16.8, 17.9, 22.0, and 25.4 degrees 2θ.

14. A compound which is a crystalline form of a tert-butyl methyl ether solvate of (Z)-6-((2S,4S,5R)-2-(2-chlorophenyl)-4-(2-hydroxyphenyl)-1,3-dioxan-5-yl)hex-4-enoic acid having an X-ray powder diffraction pattern as shown in FIG. 12.

15. A pharmaceutical composition comprising a therapeutically effective amount of the compound of claim 1 and a pharmaceutically acceptable vehicle.

16. A pharmaceutical composition comprising a therapeutically effective amount of the compound of claim 8 and a pharmaceutically acceptable vehicle.

17. A pharmaceutical composition comprising a therapeutically effective amount of the compound of claim 9 and a pharmaceutically acceptable vehicle.

18. A method of treating infection in a patient comprising administering to the patient a compound according to claim 1.

19. A method of treating cancer in a patient in need thereof comprising administering to the patient a compound according to claim 1.

* * * * *

UNITED STATES PATENT AND TRADEMARK OFFICE
CERTIFICATE OF CORRECTION

| | |
|---|---|
| PATENT NO. | : 8,536,196 B2 |
| APPLICATION NO. | : 12/523843 |
| DATED | : September 17, 2013 |
| INVENTOR(S) | : Sorensen et al. |

It is certified that error appears in the above-identified patent and that said Letters Patent is hereby corrected as shown below:

Title page, column 1 Item [60] (Related U.S. Application Data), after "provisional application No. 60/989,808, filed on Nov. 21, 2007" insert -- , international application No. PCT/IB2007/002542, filed on January 18, 2007 --.

Signed and Sealed this
Seventeenth Day of December, 2013

Margaret A. Focarino
*Commissioner for Patents of the United States Patent and Trademark Office*